(12) United States Patent
Perera et al.

(10) Patent No.: US 6,596,925 B1
(45) Date of Patent: Jul. 22, 2003

(54) COMPOSITIONS AND METHODS FOR THE MODIFICATION OF GENE EXPRESSION

(75) Inventors: J. Ranjan Perera, Auckland (NZ); Clare Eagleton, Auckland (NZ); Stephen J. Rice, Auckland (NZ)

(73) Assignees: Genesis Research & Development Corp. Ltd., Parnell (NZ); Rubicon Forests Holdings Ltd., Auckland (NZ)

( * ) Notice: Subject to any disclaimer, the term of this patent is extended or adjusted under 35 U.S.C. 154(b) by 0 days.

(21) Appl. No.: 09/598,401

(22) Filed: Jun. 20, 2000

Related U.S. Application Data

(63) Continuation-in-part of application No. 09/276,599, filed on Mar. 25, 1999, now Pat. No. 6,380,459
(60) Provisional application No. 60/146,591, filed on Jul. 30, 1999.

(51) Int. Cl.$^7$ ............................ C12N 15/09; C12N 15/29; C12N 15/82; A01H 5/00
(52) U.S. Cl. ........................ 800/278; 800/287; 800/298; 800/295; 435/69.1; 435/419; 435/468; 435/320.1; 536/23.1; 536/24.5; 536/23.6
(58) Field of Search .............................. 800/287, 278, 800/298, 295; 536/23.1, 23.6, 24.1, 24.5; 435/69.1, 419, 468, 320.1

(56) References Cited

U.S. PATENT DOCUMENTS

| | | |
|---|---|---|
| 5,510,474 A | 4/1996 | Quail et al. |
| 5,639,952 A | 6/1997 | Quail et al. .................. 800/205 |
| 5,656,496 A | 8/1997 | Quail et al. .................. 435/320 |
| 5,750,385 A | 5/1998 | Shewmaker et al. |

FOREIGN PATENT DOCUMENTS

| | | | |
|---|---|---|---|
| WO | 9747756 | 12/1997 | ........... C12N/15/82 |
| WO | 0058474 | 10/2000 | ........... C12N/15/29 |

OTHER PUBLICATIONS

GenBank Accession No. AJ012552 (VFA012552), submitted Nov. 13, 1998.
GenBank Accession No. L41658 (SCFPOLY), submitted Nov. 28, 1995.
GenPept Accession No. AAB21993, submitted May 7, 1993.
Christensen, Allen H. et al., "Maize polyubiquitin genes: structure, thermal perturbation of expression and transcript splicing, and promoter activity following transfer to protoplasts by electroporation", *Plant Molecular Biology*, vol. 18, pp. 675–689 (1992).
GenPept Accession No. AAA68878, submitted Jun. 23, 1995.
Callis, Judy et al., "Structure and Evolution of Genes Encoding Polyubiquitin and Ubiquitin–Like Proteins in *Arabidosis thaliana* Ecotype Columbia", *Genetics*, vol. 139, pp. 921–939 (1995).

EMBL Accession No. D10851 (ATHCDC2BG), submitted Apr. 14, 2000.
Imajuku, Yoshiro et al., "Exon–intron organization of the *Arabidopsis thaliana* protein kinase genes CDC2a and CDC2b", *FEBS Letters*, vol. 304, No. 1, pp. 73–77 (1992).
EMBL Accession No. U12012 (PTU12012), submitted Mar. 23, 1996.
Voo, Kui Shin et al., "4–Coumarate:Coenzyme A Ligase from Loblolly Pine Xylem. Isolation, Characterization, and Complementary DNA Cloning", *Plant Physiology*, vol. 108, pp. 85–97 (1995).
GenBank Accession No. AF139445, submitted Jun. 1, 1999.
Asamizu, Erika et al., "Structural Analysis of *Arabidopsis thaliana* Chromosome 5.VIII. Sequence Features of the Regions of 1,081,958 bp Covered by Seventeen Physically assigned P1 and TAC Clones", *DNA Research*, vol. 5, pp. 379–391 (1998).
GenBank Accession No. AB016885, submitted Dec. 27, 2000.
SWISS–PROT Accession No. O24493 (MC1_PINRA), submitted Jul. 15, 1999.
GenBank Accession No. AF075270, submitted Sep. 24, 1998.
GenBank Accession No. U53418 (GMU53418), submitted May 28, 1997.
Tenhaken, Raimund et al., "Cloning of an Enzyme That Synthesizes a Key Nucleotide–Sugar Precursor of Hemicellulose Biosynthesis from Soybean: UDP–Glucose Dehydrogenase", *Plant Physiology*, vol. 112, pp. 1127–1134 (1996).
GenBank Accession No. Z14990 (ATUBC9), submitted May 18, 1993.
Girod, Pierre–Alain et al., "Homologs of the essential ubiquitin conjugating enzymes UBC1, 4 and 5 in yeast are encoded by a multigene family in *Arabidopsis thaliana*", *Plant Journal*, vol. 3, No. 4, pp. 545–552 (1993).
Walden, Adrian R. et al., "Genes Expressed in *Pinus radiata* Male Cones Include Homologs to Anther–Specific and Pathogenesis Response Genes", *Plant Physiology*, vol. 121, pp. 1103–1116 (1999).
GenBank Accession No. U90350 (PRU90350), submitted Oct. 10, 1997.
EMBL Accession No. D63396 (NTBY2A, TOBBY2A), submitted Feb. 13, 1999.

(List continued on next page.)

*Primary Examiner*—Elizabeth F. McElwain
*Assistant Examiner*—Medina A. Ibrahim
(74) *Attorney, Agent, or Firm*—Susan J. Friedman; Ann W. Speckman; Janet Sleath

(57) ABSTRACT

Novel isolated plant polynucleotide promoter sequences are provided, together with genetic constructs comprising such polynucleotides. Methods for using such constructs in modulating the transcription of DNA sequences of interest are also disclosed, together with transgenic plants comprising such constructs.

14 Claims, 3 Drawing Sheets

OTHER PUBLICATIONS

Kumagai, F. et al., "The Involvement of Protein Synthesis Elongation Factor 1α in the Organization of Microtubules on the Perinuclear Region during the Cell Cycle Transition from M Phase to $G_1$ Phase in Tobacco BY–2 Cells", *Bot. Acta.*, vol. 108, pp. 467–473 (1995).

GenPept Accession No. AAD56019 (AF181491_1), submitted Sep. 22, 1999.

GenBank Accession No. X74814 (EGOMTRN), submitted Sep. 22, 1994.

Poeydomenge, Odile et al., "A cDNA Encoding S–Adenosyl–L–Methionine:Caffeic Acid 3–O–Methyltransferase from Eucalyptus", *Plant Physiology*, vol. 105, pp. 749–750 (1994).

GenBank Accession No. X53043 (LEEF1A), submitted May 9, 1995.

Curie, Catherine et al., "The activation process of *Arabidopsis thaliana* A1 gene encoding the translation elongation factor EF–1α is conserved among angiosperms", *Plant Molecular Biology*, vol. 18, pp. 1083–1089 (1992).

Belknap, William R. and Garbarino, Joan E. "The Role of ubiquitin in plant senescence and stress responses," *Trends in Plant Science* vol. 1, No. 10:331–335, Oct. 1996.

Scharf, Klaus–Dieter, Materna, Tilo, Trueter, Eckardt, and Nover, Lutz. "Heat Stress Promoters and Transcription Factors," *Results Probl Cell Differ* 20:125–62, 1994.

Callis, Judy et al., "Ubiquitin Extension Proteins of *Arabidopsis thaliana*", *JBC*, vol. 265, pp. 12486–12493 (1990).

GenPept Assession No. CAA63531; submitted Nov. 9, 1995 by Ruiter, R.K.

GenPept Assession No. CAA10056; submitted Nov. 12, 1998 by Fruehling, M.

GenBank Assession No. M55147 X51434; Liaud, M. and Cerff, R., *Proc. Nat'l Acad. Sci.*, vol. 87, No. 22, pp. 8918–8922 (1990).

GenBank Assession No. X74814; submitted Aug. 27, 1993 by Poeyudomenge, O., et al.

GenBank Assession No. AF077743; submitted Jul. 13, 1998 by Rehli, M., et al.

GenBank Assession No. U73588; submitted Oct. 7, 1996 by Pere–Grau, L., et al.

GenBank Assession No. U90350; submitted Feb. 24, 1997 by Walden, A.R., et al.

GenBank Assession No. AF041463; submitted Jan. 6, 1998 by Suhandono, et al.

SEQUENCE LISTING

```
<160> NUMBER OF SEQ ID NOS: 120

<210> SEQ ID NO 1
<211> LENGTH: 3083
<212> TYPE: DNA
<213> ORGANISM: Pinus radiata
<220> FEATURE:
<221> NAME/KEY: 5'UTR
<222> LOCATION: (1)...(2064)
<220> FEATURE:
<221> NAME/KEY: intron
<222> LOCATION: (1196)...(2033)
<220> FEATURE:
<221> NAME/KEY: CDS
<222> LOCATION: (2065)...(2751)
<220> FEATURE:
<221> NAME/KEY: 3'UTR
<222> LOCATION: (2755)...(3083)

<400> SEQUENCE: 1 aaaccccto acaaatacat aaaaaaaatt ctttatttaa ttatcaaact ctccactacc      60
tttcccacca accgttacaa tcctgaatgt tggaaaaaac taactacatt gatataaaaa    120
aactacatta cttcctaaat catatcaaaa ttgtataaat atatccactc aaaggagtct    180
agaagatcca cttggacaaa ttgcccatag ttggaaagat gttcaccaag tcaacaagat    240
ttatcaatgg aaaaatccat ctaccaaact tactttcaag aaaatccaag gattatagag    300
taaaaaatct atgtattatt aagtcaaaaa gaaaaccaaa gtgaacaaat attgatgtac    360
aagtttgaga ggataagaca ttggaatcgt ctaaccagga ggcggaggaa ttccctagac    420
agttaaaagt ggccggaatc ccggtaaaaa agattaaaat tttttgtag agggagtgct    480 tgaatcatgt tttttatgat ggaaatagat tcagcaccat caaaaacatt caggacacct    540
aaaattttga agtttaacaa aaataacttg gatctacaaa aatccgtatc ggattttctc    600
taaatataac tagaattttc ataactttca aagcaactcc tcccctaacc gtaaaacttt    660
tcctacttca ccgttaatta cattccttaa gagtagataa agaaataaag taaataaaag    720
tattcacaaa ccaacaattt atttctttta tttacttaaa aaaacaaaaa gtttatttat    780
tttacttaaa tggcataatg acatatcgga gatccctcga acgagaatct tttatctccc    840
tggttttgta ttaaaaagta atttattgtg gggtccacgc ggagttggaa tcctacagac    900
gcgctttaca tacgtctcga gaagcgtgac ggatgtgcga ccggatgacc ctgtataacc    960
caccgacaca gccagcgcac agtatacacg tgtcatttct ctattggaaa atgtcgttgt   1020
tatccccgct ggtacgcaac caccgatggt gacaggtcgt ctgttgtcgt gtcgcgtagc   1080
```

```
gggagaaggg tctcatccaa cgctattaaa tactcgcctt caccgcgtta cttctcatct   1140
tttctcttgc gttgtataat cagtgcgata ttctcagaga gcttttcatt caaaggtatg   1200
gagttttgaa gggctttact cttaacattt gttttcttt gtaaattgtt aatggtggtt    1260
tctgtggggg aagaatcttt tgccaggtcc ttttgggttt cgcatgttta tttgggttat   1320
ttttctcgac tatggctgac attactaggg ctttcgtgct ttcatctgtg ttttcttccc   1380
ttaataggtc tgtctctctg gaatatttaa ttttcgtatg taagttatga gtagtcgctg   1440
tttgtaatag gctcttgtct gtaaaggttt cagcaggtgt ttgcgtttta ttgcgtcatg   1500
tgtttcagaa ggcctttgca gattattgcg ttgtacttta atattttgtc tccaaccttg   1560
ttatagtttc cctcctttga tctcacagga acctttctt ctttgagcat tttcttgtgg    1620
cgttctgtag taatatttta attttgggcc cgggttctga gggtaggtga ttattccagt   1680
gatgtgcttt ccctataagg tcctctatgt gtaagctgtt agggtttgtg cgttactatt   1740
gacatgtcac atgtcacata ttttcttcct cttatccttc gaactgatgg ttcttttct    1800 aattcgtgga ttgctggtgc catatttat ttctattgca actgtatttt agggtgtctc    1860 tttcttttg atttcttgtt aatatttgtg ttcaggttgt aactatgggt tgctagggtg    1920
tctgccctct tcttttgtgc ttctttcgca gaatctgtcc gttggtctgt atttgggtga   1980
tgaattattt attccttgaa gtatctgtct aattagcttg tgatgatgtg caggtatatt   2040
cgttagtcat atttcaattt caag atg cag atc ttt gtc aag act ctc acc      2091
                          Met Gln Ile Phe Val Lys Thr Leu Thr
                           1               5 ggt aag acc atc act ctc gag gtc gag agc tct gac acc att gac aat     2139
Gly Lys Thr Ile Thr Leu Glu Val Glu Ser Ser Asp Thr Ile Asp Asn
 10              15                  20                  25 gtt aaa gct aag atc cag gac aag gaa ggg att ccc ccc gac cag cag     2187
Val Lys Ala Lys Ile Gln Asp Lys Glu Gly Ile Pro Pro Asp Gln Gln
             30                  35                  40 cgt ctg atc ttc gca gga aag cag ctt gag gac ggc cga acc ctt gcc     2235
Arg Leu Ile Phe Ala Gly Lys Gln Leu Glu Asp Gly Arg Thr Leu Ala
                 45                  50                  55 gat tac aac atc cag aaa gaa tct acc ctc cac ctt gtt ctc cgt ttg     2283
Asp Tyr Asn Ile Gln Lys Glu Ser Thr Leu His Leu Val Leu Arg Leu
         60                  65                  70 agg ggt ggc atg caa atc ttt gta aaa aca cta act gga aag aca att     2331
Arg Gly Gly Met Gln Ile Phe Val Lys Thr Leu Thr Gly Lys Thr Ile
 75                  80                  85 aca ttg gaa gtt gag agc tcg gac acc att gac aac gtc aag gcc aag     2379
Thr Leu Glu Val Glu Ser Ser Asp Thr Ile Asp Asn Val Lys Ala Lys
     90                  95                 100                 105 atc cag gac aag gaa gga att ccc cct gac cag cag agg ctt atc ttc     2427
Ile Gln Asp Lys Glu Gly Ile Pro Pro Asp Gln Gln Arg Leu Ile Phe
                110                 115                 120 gct ggt aag cag ctg gag gat ggc agg acc ttg gct gat tac aat att     2475
Ala Gly Lys Gln Leu Glu Asp Gly Arg Thr Leu Ala Asp Tyr Asn Ile
            125                 130                 135 caa aag gaa tcg acc ctg cat ttg gtg ctt cgt cta aga gga ggc atg     2523
Gln Lys Glu Ser Thr Leu His Leu Val Leu Arg Leu Arg Gly Gly Met
        140                 145                 150 caa atc ttt gtg aaa acc ctt aca ggt aaa acc att act ctg gaa gtg     2571
Gln Ile Phe Val Lys Thr Leu Thr Gly Lys Thr Ile Thr Leu Glu Val
    155                 160                 165 gaa agc tcg gac acc att gac aat gtg aag gct aag atc cag gac aag     2619
Glu Ser Ser Asp Thr Ile Asp Asn Val Lys Ala Lys Ile Gln Asp Lys
```

-continued

| | | | | | | | | | | | | | | | | |
|---|---|---|---|---|---|---|---|---|---|---|---|---|---|---|---|---|
| | 170 | | | | 175 | | | | 180 | | | | 185 | | | |
| gag | gga | att | cca | cct | gac | cag | cag | agg | ttg | atc | ttt | gcc | ggt | aag | cag | 2667 |
| Glu | Gly | Ile | Pro | Pro | Asp | Gln | Gln | Arg | Leu | Ile | Phe | Ala | Gly | Lys | Gln | |
| | | | | 190 | | | | | 195 | | | | | 200 | | |
| ctg | gaa | gat | ggt | cgt | act | ctc | gcc | gat | tac | aat | att | cag | aag | gaa | tcg | 2715 |
| Leu | Glu | Asp | Gly | Arg | Thr | Leu | Ala | Asp | Tyr | Asn | Ile | Gln | Lys | Glu | Ser | |
| | | | 205 | | | | | 210 | | | | | 215 | | | |
| acc | ctt | cac | ctg | gtg | ctc | cgt | ctc | cgc | ggt | ggc | ttt | taggtttggg | | | | 2761 |
| Thr | Leu | His | Leu | Val | Leu | Arg | Leu | Arg | Gly | Gly | Phe | | | | | |
| | | | 220 | | | | | 225 | | | | | | | | | tgttatttgt ggataataaa ttcgggtgat gttcagtgtt tgtcgtattt ctcacgaata 2821 aattgtgttt atgtatgtgt tagtgttgtt tgtctgtttc agaccctctt atgttatatt 2881 tttcttttcg tcggtcagtt gaagccaata ctggtgtcct ggccggcact gcaataccat 2941 ttcgtttaat ataaagactc tgttatccgt tatgtaattc catgttatgt ggtgaaatgt 3001 ggatgaaatt cttagaaatt attattgtaa tttgaaactt ccttcgtcaa taatctgcac 3061 aacacattta ccaaaaaaaa aa 3083

<210> SEQ ID NO 2
<211> LENGTH: 2064
<212> TYPE: DNA
<213> ORGANISM: Pinus radiata
<220> FEATURE:
<221> NAME/KEY: 5'UTR
<222> LOCATION: (1)...(2064)
<220> FEATURE:
<221> NAME/KEY: intron
<222> LOCATION: (1196)...(2033)

<400> SEQUENCE: 2
aaaacccctc acaaatacat aaaaaaaatt ctttatttaa ttatcaaact ctccactacc    60
tttcccacca accgttacaa tcctgaatgt tggaaaaaac taactacatt gatataaaaa   120
aactacatta cttcctaaat catatcaaaa ttgtataaat atatccactc aaaggagtct   180
agaagatcca cttggacaaa ttgcccatag ttggaaagat gttcaccaag tcaacaagat   240
ttatcaatgg aaaaatccat ctaccaaact tactttcaag aaaatccaag gattatagag   300
taaaaaatct atgtattatt aagtcaaaaa gaaaaccaaa gtgaacaaat attgatgtac   360
aagtttgaga ggataagaca ttggaatcgt ctaaccagga ggcggaggaa ttccctagac   420
agttaaaagt ggccggaatc ccgtaaaaa agattaaaat ttttttgtag agggagtgct   480
tgaatcatgt ttttatgat ggaaatagat tcagcaccat caaaaacatt caggacacct   540
aaaattttga agtttaacaa aaataacttg gatctacaaa aatccgtatc ggattttctc   600
taaatataac tagaattttc ataactttca aagcaactcc tcccctaacc gtaaaacttt   660
tcctacttca ccgttaatta cattccttaa gagtagataa agaaataaag taaataaaag   720
tattcacaaa ccaacaattt atttctttta tttacttaaa aaaacaaaaa gtttatttat   780
tttacttaaa tggcataatg acatatcgga gatccctcga acgagaatct tttatctccc   840 tggtttgta ttaaaaagta atttattgtg gggtccacgc ggagttggaa tcctacagac   900
gcgctttaca tacgtctcga gaagcgtgac ggatgtgcga ccggatgacc ctgtataacc   960
caccgacaca gccagcgcac agtatacacg tgtcatttct ctattggaaa atgtcgttgt  1020
tatccccgct ggtacgcaac caccgatggt gacaggtcgt ctgttgtcgt gtcgcgtagc  1080
gggagaaggg tctcatccaa cgctattaaa tactcgcctt caccgcgtta cttctcatct  1140
tttctcttgc gttgtataat cagtgcgata ttctcagaga gcttttcatt caaggtatg   1200

-continued

```
gagttttgaa gggctttact cttaacattt gttttctttt gtaaattgtt aatggtggtt    1260 tctgtgggg aagaatcttt tgccaggtcc ttttgggttt cgcatgttta tttgggttat     1320
ttttctcgac tatggctgac attactaggg ctttcgtgct ttcatctgtg ttttcttccc    1380
ttaataggtc tgtctctctg gaatatttaa ttttcgtatg taagttatga gtagtcgctg    1440
tttgtaatag gctcttgtct gtaaaggttt cagcaggtgt ttgcgttta ttgcgtcatg     1500 tgtttcagaa ggcctttgca gattattgcg ttgtacttta atattttgtc tccaaccttg    1560
ttatagtttc cctcctttga tctcacagga acctttctt ctttgagcat tttcttgtgg     1620
cgttctgtag taatatttta atttgggcc cgggttctga gggtaggtga ttattccagt     1680
gatgtgcttt ccctataagg tcctctatgt gtaagctgtt aggtttgtg cgttactatt     1740 gacatgtcac atgtcacata ttttcttcct cttatccttc gaactgatgg ttcttttct    1800 aattcgtgga ttgctggtgc catatttat ttctattgca actgtatttt agggtgtctc     1860
tttctttttg atttcttgtt aatatttgtg ttcaggttgt aactatgggt tgctagggtg    1920
tctgccctct tcttttgtgc ttctttcgca gaatctgtcc gttggtctgt atttgggtga    1980
tgaattattt attccttgaa gtatctgtct aattagcttg tgatgatgtg caggtatatt    2040
cgttagtcat atttcaattt caag                                           2064
```

<210> SEQ ID NO 3
<211> LENGTH: 1226
<212> TYPE: DNA
<213> ORGANISM: Pinus radiata
<220> FEATURE:
<221> NAME/KEY:
<222> LOCATION:

<400> SEQUENCE: 3

```
aaaccccctc acaaatacat aaaaaaaatt ctttatttaa ttatcaaact ctccactacc    60
tttcccacca accgttacaa tcctgaatgt tggaaaaaac taactacatt gatataaaaa    120
aactacatta cttcctaaat catatcaaaa ttgtataaat atatccactc aaaggagtct   180
agaagatcca cttggacaaa ttgcccatag ttggaaagat gttcaccaag tcaacaagat    240
ttatcaatgg aaaaatccat ctaccaaact tactttcaag aaaatccaag gattatagag    300
taaaaaatct atgtattatt aagtcaaaaa gaaaaccaaa gtgaacaaat attgatgtac    360
aagtttgaga ggataagaca ttggaatcgt ctaaccagga ggcggaggaa ttccctagac    420
agttaaaagt ggccggaatc ccggtaaaaa agattaaaat tttttgtag agggagtgct     480 tgaatcatgt tttttatgat ggaaatagat tcagcaccat caaaaacatt caggacacct    540
aaaattttga agtttaacaa aaataacttg gatctacaaa aatccgtatc ggattttctc    600
taaatataac tagaattttc ataactttca aagcaactcc tccctaacc gtaaaacttt     660 tcctacttca ccgttaatta cattccttaa gagtagataa agaaataaag taaataaaag    720
tattcacaaa ccaacaattt atttctttta tttacttaaa aaaacaaaa gtttatttat    780 tttacttaaa tggcataatg acatatcgga gatccctcga acgagaatct tttatctccc    840
tggttttgta ttaaaaagta atttattgtg gggtccacgc ggagttggaa tcctacagac    900
gcgctttaca tacgtctcga gaagcgtgac ggatgtgcga ccggatgacc ctgtataacc    960
caccgacaca gccagcgcac agtatacacg tgtcatttct ctattggaaa atgtcgttgt   1020
tatccccgct ggtacgcaac caccgatggt gacaggtcgt ctgttgtcgt gtcgcgtagc    1080
gggagaaggg tctcatccaa cgctattaaa tactcgcctt caccgcgtta cttctcatct   1140
```

```
tttctcttgc gttgtataat cagtgcgata ttctcagaga gcttttcatt caaaggtata      1200
ttcgttagtc atatttcaat ttcaag                                           1226

<210> SEQ ID NO 4
<211> LENGTH: 485
<212> TYPE: DNA
<213> ORGANISM: Pinus radiata
<220> FEATURE:
<221> NAME/KEY: 5'UTR
<222> LOCATION: (1)...(431)
<220> FEATURE:
<221> NAME/KEY: TATA_signal
<222> LOCATION: (350)...(356)
<220> FEATURE:
<221> NAME/KEY: CAAT_signal
<222> LOCATION: (326)...(333)

<400> SEQUENCE: 4
agtaaaattg gcccatgtag gactaagtca aaatcaaaat tccatctcta aaagcggaac       60
tttgtcccct gaaaattttg actaatttcc aaccaaaaaa aagtgggga aaatataaaa       120 ctctaactaa taaaacaata atcaccaaaa atctatcacc aaaaatgaaa aaagattttg      180
aatactaggc catatgagct acacaaattt caaaagtatc ttacacttat tacgcacccg     240
gatgtcccca ctttcgaaaa acccgtttca agcctttcac gaaagtccaa cggtcagaaa    300
attcaaaatg actgtttgag gcagagccaa tctaggacca cgctccattt atatatggcc    360
tctgcttctc tcgacccctta gagtcctctg ctctgcgaat cttgttgtta gttactgtgt    420
acgctgtaac aatggatgcc tatgagaagt tggagaaggt gggagaagga acctatggga   480
aggtg                                                                  485

<210> SEQ ID NO 5
<211> LENGTH: 246
<212> TYPE: DNA
<213> ORGANISM: Pinus radiata
<220> FEATURE:
<221> NAME/KEY: 5'UTR
<222> LOCATION: (1)...(167)
<220> FEATURE:
<221> NAME/KEY: TATA_signal
<222> LOCATION: (185)...(191)

<400> SEQUENCE: 5
tgagaacatg ataagctgtg taaattcatg ctagtcacca taactttct cattgctttt       60 catccacact gttgattcat tcattatata agatcagatt cgtatgatat acaggcaacc    120
atagaaacaa ccagcaaagt tactagcagg aaatccaact aggtatcatg aagactacca   180
acgcaggctc gataatgttg gtgctcatta ttttgggtg ctgtttcatt ggggtcatag    240
ctacat                                                                246

<210> SEQ ID NO 6
<211> LENGTH: 600
<212> TYPE: DNA
<213> ORGANISM: Pinus radiata
<220> FEATURE:
<221> NAME/KEY: 5'UTR
<222> LOCATION: (1)...(167)
<220> FEATURE:
<221> NAME/KEY: TATA_signal
<222> LOCATION: (471)...(477)
<220> FEATURE:
<221> NAME/KEY: CAAT_signal
<222> LOCATION: (444)...(451)
```

<400> SEQUENCE: 6

```
caccaattta atgggatttc agatttgtat cccatgctat tggctaagcc attttctta      60
ttgtaatcta accaattcca atttccaccc tggtgtgaac tgactgacaa atgcggcccg     120
aaaacagcga atgaaatgtc tgggtgatcg gtcaaacaag cggtgggcga gagaacgcgg     180
gtgttggcct agccgggatg ggggtaggta acggcgtat taccggcgag ttgtccgaat      240
ggagttttcg gggtaggtag taacgtagac gtcaatggaa aaagtcataa tctccgtcaa     300
aaatccaacc gctccttcac accgcagagt tggtggccac gggaccctcc acccactcac     360
tcaatcgatc gcctgccgtg gttgcccatt attcaaccat acgccacttg actcttcacc     420
aacaattcca ggccggcttt cgagacaatg tactgcacag gaaaatccaa tataaaaggc     480
cggcctccgc ttccttctca gtagccccca gctcattcaa ttcttcccac tgcaggctac     540
atttgtcaga cacgttttcc gccatttttc gcctgtttct gcggagaatt tgatcaggtt     600
```

<210> SEQ ID NO 7
<211> LENGTH: 591
<212> TYPE: DNA
<213> ORGANISM: Eucalyptus grandis
<220> FEATURE:
<221> NAME/KEY: 5'UTR
<222> LOCATION: (1)...(591)
<220> FEATURE:
<221> NAME/KEY: TATA_signal
<222> LOCATION: (432)...(437)

<400> SEQUENCE: 7

```
agtttggaat gtgttgtgtg tgatgtgatg gagagtatca gcattccaaa catgacatgg     60
ttttaactta tctgcaatgg tttctttttt attcagcgaa ctcgatggct gatgctgaga     120
gaaatgaatt gggaagtcga tcgacaatgg cagctcaact caatgatcct caggtataag     180
cattttttg gcagctctgg tcattgtgtc ttcaactttt agatgagagc aaatcaaatt      240
gactctaata ccggttatgt gatgagtgaa tcatttgctt ttagtagctt taatttatgc     300
ccccatctta gttgggtata aaggttcaga gtgcgaagat tacatctatt ttggttcttg     360
caggacacag ggattcatgc tagacacatc agcagtgttt ctacgttgga tagtggtatg     420
tacttagcta ctataaagga aattttgata gatatgtttg atatggtgct tgtacagatc     480
tatttaatgt caatgtattt gaaactatct tgtctcataa cttttcttgaa gaatacaatg    540
atgagactgg gaaccctatc tggaagaata gagtggagag ctggaaggac a             591
```

<210> SEQ ID NO 8
<211> LENGTH: 480
<212> TYPE: DNA
<213> ORGANISM: Eucalyptus grandis
<220> FEATURE:
<221> NAME/KEY: 5'UTR
<222> LOCATION: (1)...(480)

<400> SEQUENCE: 8

```
atgctgagag aaatgaattg ggaagtcgat cgacaatggc agctcaactc aatgatcctc      60
aggtataagc attttttttgg cagctctggt cattgtgtct tcaactttta gatgagagca     120
aatcaaattg actctaatac cagttatgtg atgagtgaat catttgcttt tagtagcttt      180
aatttatgcc cccatcttag ttgggtataa aggttcagag tgcgaagatt acatctattt      240
tggttcttgc aggacacagg gattcatgct agacacatca gcagtgtttc tacgttggat      300
agtggtatgt acttagctac tataaaggaa attttgatag atatgtttga tatggtgctt      360
```

```
gtacagatct atttaatgcc aatgtatttg aaactatctt gtctcataac tttcttgaag      420
aatacaatga tgagactggg aaccctatct ggaagaatag agtggagagc tggaaggaca      480
```

```
<210> SEQ ID NO 9
<211> LENGTH: 308
<212> TYPE: DNA
<213> ORGANISM: Eucalyptus grandis
<220> FEATURE:
<221> NAME/KEY: 5'UTR
<222> LOCATION: (1)...(259)

<400> SEQUENCE: 9
```

```
gcccatctca ggtgcaacgg tttaactgat gtttactaca cgcaagggg aggtatccgg       60 aaagcttgca aatcgggtaa aaacgaaaat gggcgacgtg gactcagcct gcccatgttt     120
tcggtctctc tcctggactt ccatgcccga taagggccgc caactctctc tctctctctc     180
tttttctctc acatctctct gcctgttcat gtcgcctgca agtgaagatt cgtcggagca     240
agaaggacga accgggcaca tggcggggtc ggcggtcgcg acggttctaa agggtctctt     300
cctggtgt                                                              308
```

```
<210> SEQ ID NO 10
<211> LENGTH: 300
<212> TYPE: DNA
<213> ORGANISM: Eucalyptus grandis
<220> FEATURE:
<221> NAME/KEY: 5'UTR
<222> LOCATION: (1)...(251)

<400> SEQUENCE: 10
```

```
gcccatctca ggtgcaacgg tttaactgat gtttactaca cgcaagggg aggtatccgg       60 aaagcttgca aatcgggtaa aaacgaaaat gggcgacgtg gactcagcct gcccatgttt     120
tcggtccctc tcctggactt ccatgcccga taaaggccgc caactctctc tcttttctc     180 tcacatctct ctgcctgttc atgtcgcctg caagtgaaga ttcgtcggag caagaaggac     240
gaactgggca tatggcgggg tcggcggtcg cgacggttct aaagggtctc ttcctggtgt     300
```

```
<210> SEQ ID NO 11
<211> LENGTH: 297
<212> TYPE: DNA
<213> ORGANISM: Eucalyptus grandis

<400> SEQUENCE: 11
```

```
gtgcaacggt ttaactgatg tttactacac gcaaggggga ggtatccgga aagcttgcaa      60
atcgggtaaa aacgaaaatg ggcgacgtgg actcagcctg cccatgtttt cggtctctct     120
cctggacttc catgcccgat aagggccgcc aactctctct ctctctctct ttttctctca     180
catctctctg cctgttcatg tcgcctgcaa gtgaagattc gtcggagcaa gaaggacgaa     240
ctgggcatat ggcggggtcg gcggtcgcga cggttctaaa gggtctcttc ctggtgt       297
```

```
<210> SEQ ID NO 12
<211> LENGTH: 661
<212> TYPE: DNA
<213> ORGANISM: Eucalyptus grandis

<400> SEQUENCE: 12
```

```
ctgagccatt taattcgaga gcacatcgcc caaaattatt cttcttgctg ccataactgt       60
cgaatttcct cttttaggta agtaaccaat gatgcatcat gttgacaaaa aggctgatta     120
gtatgatctt ggagttgttg gtgcaaattt gcaagctgac gatggcccct cagggaaatt     180
```

```
aaggcgccaa cccagattgc aaagagcaca aagagcacga tccaaccttt ccttaacaag      240
atcatcacca gatcggccag taagggtaat attaatttaa caaatagctc ttgtaccggg      300
aactccgtat ttctctcact tccataaacc cctgattaat ttggtgggaa agcgacagcc      360
aacccacaaa aggtcagatg tcatcccacg agagagagag agagagagag agagagagag      420
agagttttct ctctatattc tggttcaccg gttggagtca atggcatgcg tgacgaatgt      480
acatattggt gtagggtcca atattttgcg ggagggttgg tgaaccgcaa agttcctata      540
tatcgaacct ccaccaccat acctcacttc aatccccacc atttatccgt tttatttcct      600
ctgctttcct tgctcgagt ctcgcggaag agagagaaga gaggagagga gagaatgggt      660
t                                                                     661

<210> SEQ ID NO 13
<211> LENGTH: 336
<212> TYPE: DNA
<213> ORGANISM: Pinus radiata

<400> SEQUENCE: 13
actagtgatt tgttgagaat gagtaggcat tgctacaccc atcatcacaa gcatcatcat       60
gaggagaaga agatccattt ctcactctat tactcgaact tccttcagat taggctgtgt      120
atttctcact ctaccactcc aacttccttc aaatgctgtg agttttttgtt gtaattgccc      180 cgtctattta atcgcagc agcactcgta atataaagac ccgtgtgtgt gaacaacaac      240
caagtgattt gaattggaaa tgaagagcga gaatggcggt gtcatgaccg ggagcaacca      300
gcccgggccg tcgaccacgc gtgccctata gtaatc                                336

<210> SEQ ID NO 14
<211> LENGTH: 763
<212> TYPE: DNA
<213> ORGANISM: Pinus radiata

<400> SEQUENCE: 14
actagtgatt tgttgagaat gagtaggcat tgctacaccc atcatcacaa gcatcaacat       60
gaagagaaga agacgatcca tttctcactc tatcactcca acttccttca gattaggctg      120
tgtatttctc actctaccac tccaactacc actccaactt attgccgcaa aagagagagg      180
ttcccaaact ctgtcggaat ctcccactc aaagcattaa aggaaagatc taattgctgc      240
aaaaaagaga gattcccaat atatttctca actcccttca aatgatttct cactctacca      300
ctccaactcc cttcaaatga tttctcactc taccactcca acttccttca aatgctgtga      360 gttttttgttg taattgcccc gtctatttat aatcgcagca gcactcgtca tataaagacc      420
cgtgcgtgtg aacaacaatg gcggtgtctt gactgggagc aaccgcataa agaaagtggg      480
cttcatacat taaaaaaatc tgtaaatttt acggatttgg aaaaaggaag agcaggaggg      540
acctcccgac ttgacccgag aatggcggtg tcttgaccgc gtaaagaaag tggtcttctg      600
tacccgactt gacccgaaaa aagaggaaac gttgaacgag acaatctctg ggaacttcat      660
cgaaatgaac ctcacgactt gactctttcg attgtactgt tttcattgtt cccgcgtaaa      720
acgaccagcc cggccgtcg accacgcgtg ccctatagta atc                         763

<210> SEQ ID NO 15
<211> LENGTH: 40
<212> TYPE: DNA
<213> ORGANISM: Artificial Sequence
<220> FEATURE:
```

<223> OTHER INFORMATION: Made in a lab

<400> SEQUENCE: 15
acggataaca gagtctttat attaaacgaa atggtattgc                              40

<210> SEQ ID NO 16
<211> LENGTH: 51
<212> TYPE: DNA
<213> ORGANISM: Artificial Sequence
<220> FEATURE:
<223> OTHER INFORMATION: Made in a lab

<400> SEQUENCE: 16
tgacgcggcc gcgaccgacg aaagaaaaa tataacataa gagagtctga a                  51

<210> SEQ ID NO 17
<211> LENGTH: 27
<212> TYPE: DNA
<213> ORGANISM: Artificial Sequence
<220> FEATURE:
<223> OTHER INFORMATION: Made in a lab

<400> SEQUENCE: 17
tatagcggcc gcgggggggg gggggggg                                          27

<210> SEQ ID NO 18
<211> LENGTH: 30
<212> TYPE: DNA
<213> ORGANISM: Artificial Sequence
<220> FEATURE:
<223> OTHER INFORMATION: Made in a lab

<400> SEQUENCE: 18
cggagaacaa ggtggagggt agattctttc                                        30

<210> SEQ ID NO 19
<211> LENGTH: 31
<212> TYPE: DNA
<213> ORGANISM: Artificial Sequence
<220> FEATURE:
<223> OTHER INFORMATION: Made in a lab

<400> SEQUENCE: 19
tctgcatctt gaaattgaaa tatgactaac g                                      31

<210> SEQ ID NO 20
<211> LENGTH: 363
<212> TYPE: DNA
<213> ORGANISM: Eucalyptus grandis

<400> SEQUENCE: 20
aatcgggtga aaatagggcc gccctaaatt agaattgaca acatttcttg ggcaaagtta        60
atgtaagtta catgaaaaaa aaaaaaaagg atagtttgtt ggaagtaatg gagcatttgt       120
attgtgaaat tcacgataga gctaacaaaa ataaaggtag ttggtgggtt aacccagtta       180 aaaagaaca ataatttgaa gagaggagag agagagagag gaggggagga gcatttcgat        240
aaattcacta gaaaaaatgc gtgttttagt ataaatgaga gtggaaatag gccatctag        300 ggaacgatcg atcgcccctg cacccggcca tctggagagt ctgtttatac ttctctccgg       360
ctt                                                                    363

<210> SEQ ID NO 21
<211> LENGTH: 839

<212> TYPE: DNA
<213> ORGANISM: Pinus radiata
<220> FEATURE:
<221> NAME/KEY: misc_feature
<222> LOCATION: (1)...(839)
<223> OTHER INFORMATION: n = A,T,C or G

<400> SEQUENCE: 21

| | | | | | |
|---|---|---|---|---|---|
| gtatggagtt | ttgaagggct | ttactcttaa | catttgtttt | tctttgtaaa | ttgttaatgg | 60 |
| tggtttctgt | gggggaagaa | tcttttgcca | ggtccttttg | ggtttcgcat | gtttatttgg | 120 |
| gttatttttc | tcgactatgg | ctgacattac | tagggctttc | gtgctttcat | ctgtgttttc | 180 |
| ttcccttaat | aggtctgtct | ctctggaata | tttaattttc | gtatgtaagt | tatgagtagt | 240 |
| cgctgtttgt | aataggctct | tgtctgtaaa | ggtttcagca | ggtgtttgcg | ttttattgcg | 300 |
| tcatgtgttt | cagaaggcct | ttgcagatta | ttgcgttgta | ctttaatatt | ttgtctccaa | 360 |
| ccttgttata | gttccctcc | tttgatctca | caggaaccct | ttcttctttg | agcattttct | 420 |
| tgtggcgttc | tgtagtaata | ttttaatttt | gggcccgggt | tctgagggta | ggtgattatt | 480 |
| cncagtgatg | tgctttccct | ataaggtcct | ctatgtgtaa | gctgttaggg | tttgtgcgtt | 540 |
| actattgaca | tgtcacatgt | cacatatttt | cttcctctta | tccttcgaac | tgatggttct | 600 |
| ttttctaatt | cgtggattgc | tggtgccata | ttttatttct | attgcaactg | tattttaggg | 660 |
| tgtctctttc | tttttgattt | cttgttaata | tttgtgttca | ggttgtaact | atgggttgct | 720 |
| agggtgtctg | ccctcttctt | ttgtgcttct | ttcgcagaat | ctgtccgttg | gtctgtatttt | 780 |
| gggtgatgaa | ttatttattc | cttgaagtat | ctgtctaatt | agcttgtgat | gatgtgcag | 839 |

<210> SEQ ID NO 22
<211> LENGTH: 881
<212> TYPE: DNA
<213> ORGANISM: Eucalyptus grandis

<400> SEQUENCE: 22

| | | | | | |
|---|---|---|---|---|---|
| acgtgacgat | gctcgagtct | cgcgttctcc | tctctcttgt | tctgcaaaac | agaaaagaga | 60 |
| gaatggaggt | tggcctctct | caattacgtg | gacgccaatg | agataactca | ggtgggcgac | 120 |
| aaaacaaacg | cctcttgatt | tcctcaaacc | ccaaaccgaa | tccctcgtca | aggggcaagg | 180 |
| cttttggtcc | cgcggcccca | cggatcgctc | gttcccgtct | cgccacgtcg | cgtcgcagcg | 240 |
| tgtcgagcaa | acagaggggt | ccgagcgact | ataaaatccc | gacgccatcg | acaccacagt | 300 |
| ccatcgaaaa | ccttgttcaa | ttcccaagtg | aaagtgagta | actgtgaacg | aagagttgaa | 360 |
| cttttgcatct | cggcgtgtgg | attcaagagg | aagcagcaaa | gtggaaatgg | acaactccaa | 420 |
| gatgggcttc | aatgcaggc | aggccaaggg | ccagactcag | gagaagagca | accagatgat | 480 |
| ggataaggca | tccaacactg | ctcaatctgc | aagggattcc | atgcaagaga | ctggtcagca | 540 |
| gatgaaggcc | aaagcccagg | gtgctgctga | tgcagtgaag | aatgccaccg | ggatgaacaa | 600 |
| atgaagagct | caagacatga | atgaataaat | aattaagctc | tggttatcat | ttgcttttcc | 660 |
| ggtcgtttgt | tgtcctgttt | ttccttgtca | agagcttatt | atgagggtcc | ttttgctctt | 720 |
| tccttagttc | tttttgtttc | ttggttgttc | catgaagaga | gcaactctct | gtgtttgaga | 780 |
| gtactcatct | cgcttcataa | ggtctcagta | tgtagttgcc | tttcgagaat | gttatgttct | 840 |
| ctctcataat | gctattctga | ttttataaaa | aaaaaaaaa | a | | 881 |

<210> SEQ ID NO 23
<211> LENGTH: 350
<212> TYPE: DNA

<210> SEQ ID NO 23
<211> LENGTH: 350
<212> TYPE: DNA
<213> ORGANISM: Eucalyptus grandis

<400> SEQUENCE: 23

```
ctatagggca cgcgtggtcg acggcccggg ctggtccttt cttacaaaaa gcaaaattct      60
tataatttt tttgatataa taaaaatgat ccataaactt ttgcttaatg tgcaacgtaa     120
accataatat attcaacgtg atgcttaaac tttaatcgag tatgcaatgt agtccataat    180
atattcaata tgatccttca atccaattga agtgtgcaat gtggtcgcta gatttttta     240
tgtattcaac ttagtcttta agctaccaac cttccaataa tttatgtttt agaaataata    300
tcgaacatct tttatattat tcaaggaata aaacgaacat gcatcaaaag                350
```

<210> SEQ ID NO 24
<211> LENGTH: 49
<212> TYPE: DNA
<213> ORGANISM: Eucalyptus grandis

<400> SEQUENCE: 24

```
actatagggc acgcgtggtc gacggcccgg gctggtactt tttttttct                 49
```

<210> SEQ ID NO 25
<211> LENGTH: 909
<212> TYPE: DNA
<213> ORGANISM: Eucalyptus grandis

<400> SEQUENCE: 25

```
cagggtaaag aaaatggaat atttgcttgg ccccccagct ttgaaagttg ctgtaagaac      60
acactcacct tgcatttata cgatggttgt gagcagtgca ggctggtggt gctgcaaatt    120
tatgatgctg atgtgatagg cagatgaatg gcagttgagc taagttaaag ccctcataca    180
tagatcagag caggaggagt agtatatata ggcatcttgg caagtcccta aaagagcggc    240
ttcgtgtatt cccacatatt cctctctcgt tagaacgttc agaaatgggt ggcccttga     300
ctcttgatgc agaggttgag gttaagtctc ctgcagacaa gttctgggtg agcgtgagag    360
actccaccaa actgttccca agatcttccc ggaccagta caagaatatt gaagtccttg     420
agggagatgg gaaggctcct ggctcagttc gcctcttcac gtatggtgaa ggttctccac    480
ttgttaaagt atcaaaggag aagattgatg gtgtggacga agcagacaag gtcgtgacct    540
acagcgttat agacggtgat ctcctgaagt actacaagaa tttcaatggc agcatcaagg    600
taattcctaa aggagacgga agcttggtga atggtcgtg tgggtttgag aaggcaagcg     660
atgaaattcc tgatccccac gtaatcaagg acttcgcaat ccagaatttc aaagagcttg    720
atgagttcat cctcaaggca tagatgccgc caatcgtcta tccggatttg cactaaatat    780
caataaaata atgcggagct ggactccgca cttctatatg catctagtat gagagtcccc    840
tgctgtctct gtttgtattc acttgaaggg ttttctatta agctctcttt actgcctccg    900
aaaaaaaaa                                                            909
```

<210> SEQ ID NO 26
<211> LENGTH: 430
<212> TYPE: DNA
<213> ORGANISM: Eucalyptus grandis

<400> SEQUENCE: 26

```
tggagcttga gatagatcga ccagagagatc ccagcggaaa tagaagattt cctgatacca    60
tcgatccttc ttctccaatg gctgcgaatt tcgtcattcc gaccaaaatg aaggcttggg    120
tgtaccgtga gcacggaaac gtcgccgacg tattgggatt ggacccggaa ctcaaggtcc    180
```

```
ctgaattgca agaaggccaa gtgctggtta agttcttgc cgcagcgctc aatccagtcg      240
acgccgcgag aatgaagggg gttatcaagc tcccgggctt ttctctaccg gccgtgccag      300
gttacgatct cgccggcgtt gtggtaaagg tgggccgcga agtgaaggag ctcaagatcg      360
gggacgaggt atatggattt atgtttcacg ccaagaaaga cgggacgctg gctgagtacg      420
cagccgtgga                                                              430

<210> SEQ ID NO 27
<211> LENGTH: 1253
<212> TYPE: DNA
<213> ORGANISM: Eucalyptus grandis

<400> SEQUENCE: 27
gcttgagata gatcgactga gagatcctag tggaaataga agatttcctg ataccatcga       60
tccattcttc tccaatggct gcgaatttcg tcattccaac caaatgaag gcttgggtgt      120 accgtgagca cggagacgtc gccaacgtat tgggattgga cccggaactc aaggtccctg      180
aattgcaaga aggccaagtg ctggttaaag ttcttgccgc ggcgctcaat ccaatcgaca      240
ccgcgagagt gaagggggtt atcaagctcc cgggcttttc tctaccggcc gtgccaggtt      300
acgatctcgc cggcgttgtg gtgaaggtgg gccgcgaagt gaaggagctc aaggtcgggg      360
acgaggtata tggatttatg tttcacgcca agaaagacgg gacgctggct gagtacgcag      420
ccgtggaaga gtcgttcttg gctttgaagc ccaagaagct gcgtttcggg gaggctgctt      480
ctctgccggt ggtcattcag accgcctatg gaggccttga agagctggc ctctctcatg      540 gcaagtccct cctcgtctta ggtggtgctg gtggcgtcgg cacactcata atacagctag      600
ctaaggaagt ttttggtgca tcaagagtag cagctacatc cagcactggg aagctagagt      660
tgttgaagag cttgggtgct gatctggcca ttgactacac caaagtcaac tttgaagacc      720
tcccagaaaa gtttgatgtt gtctacgata cagttgggga aattgagcgg gcagcgaagg      780
ctgtgaagcc aggagggagc atcgtgacga tcgtaaaaca aaacaagaca ttaccccccgc      840 ctgctttctt ttttgcagta acttcgaacc gttcgacctt ggagaagttg aagcccttct      900
tggagagcgg gaaggtgaag ccggtgatcg accccaagag cccgttccca ttttcgcaag      960
ccattgaggc cttctcgtat cttcaaaccc gccgggcaac tggaaaactc gtgattcacc     1020
ccgtcccatg atacacaaac gagaaagaaa taaagcgtcc acatggatct gccttaatca     1080
cgagtcctta attagtagtc gatggtgctt gctgtttgtc tccgtacatt cagcttctct     1140
ttgcatagta gtttctacat agtgcgtgta gagaagcaag tggatgtaca agtaaaataa     1200
ttactttttc tataaacaat attacaaact caaaaaaaaa aaaaaaaaa aaa              1253

<210> SEQ ID NO 28
<211> LENGTH: 99
<212> TYPE: DNA
<213> ORGANISM: Eucalyptus grandis

<400> SEQUENCE: 28
gatagatcga ccgagagatc ccagcggaaa tagaagattt cctgatacca tcgatccatt       60
cttctccaat ggctgcgaat ttcgtcattc cgaccaaaa                               99

<210> SEQ ID NO 29
<211> LENGTH: 927
<212> TYPE: DNA
<213> ORGANISM: Eucalyptus grandis
```

<400> SEQUENCE: 29

```
cgacgtcgca tgctcccggc cgccatgcgg ccgcgggaat tcgattacta tagggcacgc      60
gtggtcgacg gcccgggctg gtactctcac taattcttta gttttccaat ttagccccctt   120
ctgtaattgc tcatcttctt taccaaattc tctaatttgg ccggcgaagg gctgacaagg    180
gattggtcat gtcaccctca ccaaaggttg ccgaaggtcc ggtgacctca gctgacggcc    240
acctacacca aatctagctc actagcagcc taagcccttc atcaactcta gtgaaaggtt    300
ttgagtattt tttaataaaa aatatttaaa aaatatatag cgagagctca ttacaaaaaa    360
atttaaaaa aaaatctaaa cattacttga actcaaagtg actttataaa gagttttttac    420
caaaggatct tggtttcatc atttgcacta cacccaaaac ccaatttcta agttaaatca    480
aacccactgt ctaatagaga taaggtaaat gttataaacc aaattccaaa attccgaagc    540
actaaatata tttgctgatc ttataatcgc caattgagag ggtctcattc tccaagggat    600
tgtgacatat tagtaattga tagggtctca tccgtaggac tccgactcag ccgcgccacg    660
tgactggatc gctgaacggc gcggaaccag aggagcgtga ttacctaata tttttctccta   720
ccttggcctt gagattgaat tcagaaaaaa gaaaagaaaa aaggaacaac ttcgccgact    780
gttctataaa atgcatgcgc caccccgacc cccacccacg catcacatcc atccagcctc    840
cacgacagac gcataaacac aacacacgtc ggttagagag agagagagag agagagagag    900
agagagagag atgcttggac agttgtc                                        927
```

<210> SEQ ID NO 30
<211> LENGTH: 411
<212> TYPE: DNA
<213> ORGANISM: Eucalyptus grandis

<400> SEQUENCE: 30

```
actatagggc acgcgtggtc gacggcccgg gctggtctga aactgtcgct cggcgatgca      60
taccaaaggc tgaaggtatc agaatctaat gcagcttatg taaaagcgcg atcaatttat   120
tgaccccgac gaccttgact ccatacttca cgcctcagct ttgtgttgga tggtcttgac    180
ctctctcacc ctaaaaggta gctcaaaaga atgagacttt ccgtcatact tataaaccga    240
ccaccagcct cttttcacaac cgacatggga caacctcaaa tagaattttt aacaacaccc   300
ttgcacgctc tttctatcca ctttattatg ccatcacatg agcgttttcc acgcgtaaat    360
cggctaccac ccactttcac acggcggcga aacgagaaaa aggtcctacc t             411
```

<210> SEQ ID NO 31
<211> LENGTH: 178
<212> TYPE: DNA
<213> ORGANISM: Eucalyptus grandis

<400> SEQUENCE: 31

```
cgagtcagca gaaacccagt tacactccgc ccaaacggaa gctaaacctg atgggccata      60
cgatttcttt cactgagcct cttgcttttc ctccggaatc tcacggcacc ggaatgccgg    120
aggaacttgg gaagaaccaa tgatgcctgg tcactgagtg atcgatgaat gcaatagt      178
```

<210> SEQ ID NO 32
<211> LENGTH: 178
<212> TYPE: DNA
<213> ORGANISM: Eucalyptus grandis

<400> SEQUENCE: 32

```
gtccaatgtc ctgtcaaagg aggaaagatg actatggccc cggcgccggc ggggactgca      60
```

-continued

```
tgggatttag tatgttgatt gagtacccgt cgccaccacc ttcaagtaaa tcaggagtca      120
gcagaaaccc agtacactcg ccaaacggag ctaaacctga tggccatacg atttcttt       178
```

<210> SEQ ID NO 33
<211> LENGTH: 178
<212> TYPE: DNA
<213> ORGANISM: Eucalyptus grandis

<400> SEQUENCE: 33

```
gcatgggatt tagtatgttg attgagtacc cgtcgccacc accttcaagt aaatcaggag      60
tcagcagaaa cccagtacac tcgccaaacg gagctaaacc tgatggccat acgatttctt     120
tcactgagcc tcttgctttt cctccggaat ctcacggcac cggaatgccg gaggcaac       178
```

<210> SEQ ID NO 34
<211> LENGTH: 1274
<212> TYPE: DNA
<213> ORGANISM: Eucalyptus grandis

<400> SEQUENCE: 34

```
ctatagggca cgcgtggtcg acggcccggg ctggtccttt cttacaaaaa gcaaaattct      60
tataattttt tttgatataa taaaaatgat ccataaactt ttgcttaatg tgcaacgtaa     120
accataatat attcaacgtg atgcttaaac tttaatcgag tatgcaatgt agtccataat     180
atattcaata tgatccttca atttaattg aatgtgcaat gtggtcgcta gattttttta     240
tgtattcaac ttagtcttta agctaccaac cttccaataa tttatgttta gaaataatat     300
cgaacatctt ttatattatt caaggaataa aacgaacatg catcaaaagt ttaaatatat     360
caaataaaat aaaattttaa gaattatatt acatattaaa attaaagttc atgattaaat     420
tgaaataaaa taaaaattta aaaatcacgt tgtatgttgt gccgaaacaa aattcagtga     480
cttgtggtgt caattttctt aggtggagct ccacaagcat tgagatggag tgttccttcc     540
gccgaggttt tcattgcgtg gctcaaaacg gtggcgcgtt ttgcacgaca cgagatgcct     600
cgattgccgc atcgtgtagg cgacgcaacg gaaaaacgcg ttgccgtggc gtctatccgg     660
ggtttcgtct ccgatgcggc acgtagccta taaatgcgca cgatctcccg gtctgccaat     720
tcgctatcga ttgcagaaga aaactcaaac cctaggcgct ctctctccgt tcgacctctc     780
gaagttctcc tctcttcgcg tcaagatgca aatctttgtg aaaacccta ctggcaagac     840 aatcaccctc gaggtggaaa gctcggacac agtcgataat gtgaaagcaa aaatccagga     900
caaggaaggg atccctccgg accagcagag gcttatcttt gctggcaagc agctggaaga     960
tggccgaacc ttggccgatt ataacattca gaaggagtcc accctccact tggtgctccg    1020
tctcagggga ggcatgcaaa tttttgtgaa gactcttact ggcaagacaa tcaccctcga    1080
ggtggaaagc tccgacacag ttgataatgt gaaagcaaaa atccaggaca aggaagggat    1140
ccctccggac cagcagaggc ttatctttgc tggcaagcag ctggaagatg ccgaaccttt    1200
ggccgattat aacattcaga aggagtccac cctccacttg gtgctccgtc taagggagg     1260 catgcaaatc tttg                                                      1274
```

<210> SEQ ID NO 35
<211> LENGTH: 795
<212> TYPE: DNA
<213> ORGANISM: Eucalyptus grandis

<400> SEQUENCE: 35

-continued

| | |
|---|---|
| aaaaatacag gctttcgaaa gctagtgcgg tataaataac ctgggaaaag caagccgctt | 60 |
| gagctttagt ttcagtcagc catggccact cacgcagctc ttgctccctc aaccctcccc | 120 |
| gccaatgcca agttctctag caagagctcc tctcactcct tccccactca atgcttctct | 180 |
| aagaggctcg aggtggcgga attctcaggc cttcgtgctg gatcgtgtgt gacttatgcg | 240 |
| aagaatgccg gggagggatc cttcttcgat gctgtggctg ctcagctcac tcccaagact | 300 |
| tcagcaccag ctccagctaa gggagagact gtcgctaaac tgaaggtggc aatcaatggt | 360 |
| ttcggtcgca ttggtcggaa cttccttaga tgctggcacg ggagaaagaa ctcgcccctt | 420 |
| gatgtcattg ttgtcaatga cagcggtggt gtcaaaaatg cttcacattt gctgaagtat | 480 |
| gattccatgc tggggacttt caaagctgat gtgaaaattg tggacaatga gaccatcagc | 540 |
| gtcgatggga agcccgttaa ggtcgtctct aaccgggacc ctctcaagct ccctgggct | 600 |
| gagctcggca tcgacattgt cattgaggga actggagtct tcgtggatgg ccctggtgct | 660 |
| ggaaaacata ttcaagctgg tgccaagaaa gttatcatca ctgcaccagc aaaaggcgct | 720 |
| gatatacca cctacgtcta tggtgtgaat gagacagatt attcgcatga agttgctaac | 780 |
| ataatcagca atgct | 795 |

<210> SEQ ID NO 36
<211> LENGTH: 1200
<212> TYPE: DNA
<213> ORGANISM: Eucalyptus grandis

<400> SEQUENCE: 36

| | |
|---|---|
| aaaatatcca tcgacagcat caccccgctt agagaacggt gtctcggctt ctcacaatgt | 60 |
| ctatagccga atgtacaaaa tcggcataat gttctataat atagcggact ttacagatga | 120 |
| gcattcaaat acgtacgccg tactcgattc ccattcgatt gttcattcat ccgcatgcaa | 180 |
| atttcataga gataatatct gtgcacgtcc ttagattaag acaaccaaa gagtatctgg | 240 |
| tggaagtttg aagcatgacc accgaagtca gatggaacaa acaaggtggg tggtggggat | 300 |
| atagtggaca aaggaacgag aggtgaatag gaaaaggaga aggcaagatg cgggagatag | 360 |
| gatttacgtg gcgagcggcg attgcacgca tggtccaccc caccctcaac ctcaaacttt | 420 |
| cgaaaatgca acgggcatca gggtggcgat gaaggagacg atggagatat tgttgctttc | 480 |
| tccccccaaa aaacatcatc caatccatcc ccattcctca tcttcaccac aaggagtctg | 540 |
| aagctctcct tcaccggtcc gtcgctttct ctcttatctt cttcttctcc ctcctcttct | 600 |
| cgttcttcct tcgaccgttc tctcggtatc gtgaatttat tgcggggtgg ttcgcatgct | 660 |
| ataaattcca cagcaacgag ggccccttgc cacaatgtcg acgtctccgg ttagcagctg | 720 |
| gtgcgccacc tccttctccc ctgcccattc ctcgctcaag agagccgccg gcctacggcc | 780 |
| ctctctctcc gcccgcctcg gcccttcctc tcctcctcc tccgtctctc ctccgaccct | 840 |
| catccgtaac gagcccgttt cgccgcccc cgcccctgtc atcaacccca cttggacaga | 900 |
| agagatgggc aaggactatg acgaggccat tgaggctctc aagaaactcc tcagtgagaa | 960 |
| gggggacctg aaagccacag cagccgcaaa agtggagcaa ataactgcgg agttgcaaac | 1020 |
| tgcttcccca gacatcaagc catccagctc cgttgacaga atcaaaactg gcttcacctt | 1080 |
| cttcaagaag gagaaatacg acaagaaccc tgctttatat ggtgaactgg caaagcagag | 1140 |
| tccaaagttc atggtgtttg cttgctcgga ctcgagagtg tgcccatctc atgtgctgga | 1200 |

<210> SEQ ID NO 37
<211> LENGTH: 648

<212> TYPE: DNA
<213> ORGANISM: Eucalyptus grandis

<400> SEQUENCE: 37

```
cgacggactc ctttcacgat atcgaaacga ggaaacggag gagaagcaga agaaagaaga      60
tgaagaaagg cagatggttg gtgatggatg aaactgtcgg gaagctggga gcttcaggga     120
gttctattta tggggcgaaa cagggagggg gaaaccgaat ttaccaagat gcccttcttg     180
gtgggattgg acatggagct gcacgaccgt cgtcccatca cgaagagtct tgctcttcgg     240
tacacatgca atcgtcggcg aaccgacctt atccgaccgg ttccaagctt gtcctggtaa     300
aaggtttcga accttggaaa aggcttaaga gatgtatcgg tgccttaacc attattccat     360
gttcacataa tatttggccc ggttttcagg tcaattttgg agtagcccgg ttcggttcta     420
gtcccgctcc cgattcaaaa attcattggg aacaaatttt gacactgtct ggtatttttg     480
gtctaagacc ctacccaatt ttagaactgt acacccttgc tttatcccaa aataaaattg     540
tcaattagtc aacttttcac acttgatgat cgattaagta gatggatgac atggtctttt     600
accagcccgg gccgtcgacc acgcgtgccc tatagtgagt cgtattac                  648
```

<210> SEQ ID NO 38
<211> LENGTH: 288
<212> TYPE: DNA
<213> ORGANISM: Eucalyptus grandis

<400> SEQUENCE: 38

```
gattgtaata cgactcacta tagggcacgc gtggtcgacg gcccgggctg gtatcgtgaa      60
agaagtccgt cgacgacaat ggccgagaag agcaaggtcc tgatcatcgg agagaagagc     120
aaggtcctga tcatcggaga agagcaag gtcctgatca tcggagagaa gagcagggtc     180
cttatcatcg gagaatcgaa ttcccgcggc cgccatggcg gccgggagca tgcgacgtcg     240
ggcccaattc gccctatagt gagtcgtatt acaattcact ggccgtcg                  288
```

<210> SEQ ID NO 39
<211> LENGTH: 382
<212> TYPE: DNA
<213> ORGANISM: Eucalyptus grandis

<400> SEQUENCE: 39

```
acagcaatct catctgatga ttcttcagtt cggagctcag aggatacatc atctatagct      60
gaattgagct gtgcaatctt ctcggcaagc accttcctcg tttttctgaaa atcatcagat    120
tttaaggtga atccatattt cgcagatggc catgttactg ctacactctc ttcacagcat     180
acatgaagga ggtcacatag caagcataca taggacctca tatacaaata tgacagcaga     240
ccagcccggg ccgtcgacca cgcgtgccct atagtagtag tggggaagga gtgagaggag     300
ctcttgatga ggaatgtcgg cttttcttcc atcagttgat gttccgggtt cctagtcatt     360
atgccgatgg tggccactcc ag                                              382
```

<210> SEQ ID NO 40
<211> LENGTH: 986
<212> TYPE: DNA
<213> ORGANISM: Eucalyptus grandis

<400> SEQUENCE: 40

```
aaatacaaac tggtttaata ttcaactcag ataattacat gacaccacct aaataatgga      60
aagtcaagca aatagacata ttatccccac acataatcaa ctatattcat gactggagag     120
```

-continued

```
gtgctagatg gtatagagtc cctagttatt atttatttt ttgggcccga gaagatcctg      180
atggatctat gctgtttgat actttcagat ttgttttgtc tacagctcaa ataaattagt      240
gcttgggttt tgatatatta tctaatctga tacaagtctt tgtcctggcc aattttttgca     300 gagtttcctg caaaacagtg cactaaagct tccagaggac ctcatgccat gcccaagggc      360
accacctatg atggaacgga gaatcaaacc acagactgaa caggcgttga atgccccag       420 atgtgattct acaaacacaa aattctgtta ctataacaac tacaatcttt cacaacctcg      480
ccatttctgc aagacctgca ggcgatactg gaccaaagga ggtgccttac gtaacgttcc      540
tgttggtggg ggttgcagaa agaataaacg agccaagcga gcagtagacc atcctgtctc      600
tgctcagaat gaagcatcca cctctgcagc cccaggcaac gaagtacctg accggtctcc      660
ctttgagcca ccatcttcaa aatccattta ctatggggga gaaaacatga acttaaccgg      720 tctcccctttt agcagaattc agcaggaccg agctgcattg gcccactgca actcttcttc     780 cttttctagga atgtcatgtg gcacccaatc ggcctctctg gaaccacatc tttcggcttt     840
aaatacattt aattcattca gtctaacaa tcctggtctg gatttttccta gcttaagcac      900 agaccagaat tcactgtttg agaccagcca gccacaactg tcaagagcaa tggcatctgc      960 cctttttct atgccaatgg ctcctg                                            986
```

<210> SEQ ID NO 41
<211> LENGTH: 313
<212> TYPE: DNA
<213> ORGANISM: Pinus radiata

<400> SEQUENCE: 41

```
aaaggaaaat tcaaagatct ttagccaatt tttgttgttg tgaccttgaa tttctaaaaa       60
atttaatgga ttcgttttct aaattcctga ttcgtcaaag gctgaagggc acgatagtaa      120
tagaaaatgg acggcagttt atcctttcat ggctggacac acagaatttg tggagggact      180
ctccattctg gtttatccgc cgttagttct ctctgtactc caccccttagt tctctttgta     240 ctcgagacct ttaatgatta gccctgctta tgctgtcatt actgaactca cttccagagc     300
cccaaaaatc tct                                                         313
```

<210> SEQ ID NO 42
<211> LENGTH: 713
<212> TYPE: DNA
<213> ORGANISM: Pinus radiata

<400> SEQUENCE: 42

```
taattcacaa gtagaaaatg agattttgc aattttgtaa ctaacatttc ccggtctcct        60
ctgtatgttt tcacccctta atgtaattga aatttgcacc cgggttagat tcaaagcgga     120
gaataacatc ggggccttgt tctagacaga gattttttcac aaataacagg ttcgaaggta    180
tgtgtagaca tctgggtagt tgtagaataa agacggagcc cattaggtga tccaatcgaa     240
gagctcagat gggaaaacag ataaaaatta tcgggtggac cttccttcac atgttaatta    300
tatatcaagt gtcgccaatc cttatgtgaa acatttagta aagcttcgcc agagcacttc     360
ttataggcat tctgtgggct ctgttgttgt ggttggaagt actcctttaa gggaggtatc    420
tgaatatttg caacagaagt cagttaaaca agtggttgac tgtctgtttg tacaagatgt     480
tactggcata cctgtgggct tgatagagac ttccaggcgc attgtgcatg taaatcattt    540
ggtgatgcag aagctagccg gagtagagtc tatagagccc actgaagcaa ttggtgtaat    600
caagcttcct agcagcttct acaacttgga atctcttgaa attcactcta gttcccagat     660
```

-continued

```
atggtgctcg tcgccacatc gtctgcttgt acttgatggc attcaggatc ctg        713
```

<210> SEQ ID NO 43
<211> LENGTH: 28
<212> TYPE: DNA
<213> ORGANISM: Pinus radiata

<400> SEQUENCE: 43

```
ccacctcaca tcaataaatt ttatacga                                     28
```

<210> SEQ ID NO 44
<211> LENGTH: 35
<212> TYPE: DNA
<213> ORGANISM: Pinus radiata

<400> SEQUENCE: 44

```
gctgtttcat tggggtcata gctacgtggt gctga                             35
```

<210> SEQ ID NO 45
<211> LENGTH: 1729
<212> TYPE: DNA
<213> ORGANISM: Pinus radiata

<400> SEQUENCE: 45

```
cttattgaca tataaaagca aagttggatc catctgttat tttgggtccc ctccagaagc   60
cttactaaat gcggacaaaa atccacgta aagaacttct gaatttaccg tcatctgggc  120
tctgtaatta cgaatttagg gtttcctctg tcaatatctg gtagtgacaa acaaggttta  180
atggcagcct tagcaacaac tgaagtttgt gatacatatc cacgccttgt ggagaatggt  240
gagcttcgtg tcttgcaacc aatttttccag atatatggtc gacgtcgagc tttctctgga  300
cctatagtta cactgaaggt ctttgaggac aatgtccttt tgcgggaatt ccttgaggag  360
agaggtaatg gaagagtttt ggtagttgat ggaggaggaa gccttagatg tgccatactg  420
gggggcaatg tagttgtatc tgcccaaaac aatggttggt ctggaataat tgtcactggc  480
tgcataaggg acgttgatga aataaacaga tgtgacattg gtataagagc actgacatct  540
aacccactga aggccaacaa gaagggtgtg ggtgaaaaac atgcgcctat ttacattgct  600
ggtacccgca ttcttccggg ggaatggtgt tatgctgaca gtgatggtat tcttgtttca  660
cagcaagagt tatcactgtg agataataaa attcataagt ttcagattgt gactttcatg  720
tcctgtggaa catatatttg actcgagtta gattctaata ggattaattg atagattctg  780
aaaattgagg aatatctctg gtcatgaaaa tcttcttctc atgtgatctt ttatgctcag  840
cttttgagtac aggatgataa gaagtttgtg catgtttgtc taaaggttta gcaagtatta  900
tcggaccatc ataagagata gattatggaa ctcagggact tgctattttt aatccaaaat  960
aacatttatt ctttgtgttt ttgccaaatt aactttttatt tcccttggca ccactagtga 1020
tttgcaatat ccagttgctg agaacataga agtgggcaac ggtgagagtt gcaacagtat 1080
ctagcataga tttaacaagt attgttggat cattataaga aaataaacta cagaaccaag 1140
ggaatctagt tgacaacata gttaaagtag gcatggtgct actgtatcga tacatcttca 1200
taaacagaaa aatatgaaca agctctaatg atgggagaaa ctccagcttg gtgtttgat  1260
taagcatcca tattcacacc taaaggtta caagttccaa ataaaaatt ccaatgaatt 1320
tagccaatct aatcagacct tataagaaat acactaggca tctggggatc aaaatccagt 1380
agtttagaaa gtagttgtaa ataacccaga gacaaaaatc tcaatgatag cttgcttggg 1440
```

-continued

| | | | |
|---|---|---|---|
| tcataggttt | gataataatt | gaaaacatag | ttgaaaggag aatcctagca atggctagct | 1500 |
| tgaataatag | atgtacagca | aaattacagt | agttgagaac aaagatggaa ggataatccc | 1560 |
| aacgatagct | agcttggaca | gtaggatgat | tacatcaaaa tcatagcagt tgagaacata | 1620 |
| gttggaagga | gaatccttat | gatggctacg | ttggataata ggcgtgatta tcgtaggtag | 1680 |
| attagagcac | aagatcaaac | taatagctgg | cgcagctatc gactatttt | 1729 |

<210> SEQ ID NO 46
<211> LENGTH: 1038
<212> TYPE: DNA
<213> ORGANISM: Pinus radiata

<400> SEQUENCE: 46

| | | | | |
|---|---|---|---|---|
| tgattactat | agggcacgcg | tggtcgacgg | cccgggctgg | taaatgagaa catgataagc | 60 |
| tgtgtaaatt | catgctagtc | accataactt | ttctcattgc | ttttcatcca cactgttgat | 120 |
| tcattcatta | tataagatca | gattcgtatg | atatacaggg | aaccatagaa acaaccagca | 180 |
| aagttactag | caggaaatcc | aactaggtat | catgaagact | accaacgcag gctcgataat | 240 |
| gttggtgctc | attattttg | ggtgctgttt | cattgggtc | atagctacat cttttgattt | 300 |
| ctattacttc | gttcaacagt | ggcctggttc | atactgcgat | actcgtagag gatgctgtta | 360 |
| ccctcgcacg | ggaaggcctg | cttccgaatt | ttccattcat | ggcctctggc ccaactacaa | 420 |
| gaccggtaaa | tggccacagt | tctgtggttc | ctccgaagaa | ttcgactact caaagatctc | 480 |
| agatctggag | gaggagctga | acaggtattg | ggttcgtta | agctgtccaa gcagcgatgg | 540 |
| acaggaattt | tggggacacg | agtgggagaa | acatggcact | tgctctctca atcttgatga | 600 |
| gcattcatac | tttgagaagg | ctctctcctt | gagacaaaat | atagacattc ttggggctct | 660 |
| taaaactgca | ggtattaaac | ccgatggaag | ccaatacagt | ttgagcgata tcaaggaagc | 720 |
| cattaaacaa | aacactgggc | agctcccagg | aatcgattgc | aacacgagcg cagagggaga | 780 |
| gcatcaacta | tatcaggtgt | atgtgtgtgt | tgataaatcc | gatgcttcca ctgttattga | 840 |
| atgccccatt | tatccacaca | gcaattgccc | atccatggtt | gtgtttcctc cttttgggga | 900 |
| ggatcaggag | gaccgagatg | gttacacaga | aggaatgtac | gagctgtaga tctggacaaa | 960 |
| cagcatttct | tctctccgca | tttgattttt | atcaatgaaa | tttccgattc caacattttg | 1020 |
| taaaaaaaaa | aaaaaaaa | | | 1038 |

<210> SEQ ID NO 47
<211> LENGTH: 91
<212> TYPE: DNA
<213> ORGANISM: Pinus radiata

<400> SEQUENCE: 47

| | | | |
|---|---|---|---|
| aattttccat | tcatgcctct | gcccaactac | aagaccggta aatggccaca gttctgtggt | 60 |
| tcctccgaag | aattcgatat | caagcttatc | g | 91 |

<210> SEQ ID NO 48
<211> LENGTH: 91
<212> TYPE: DNA
<213> ORGANISM: Pinus radiata

<400> SEQUENCE: 48

| | | | |
|---|---|---|---|
| gcttttcatc | cacactggtg | cctcattcat | tatataagat cagattcgtg tgatatacag | 60 |
| gcaaccatag | aaacaaccgg | caaagttact | a | 91 |

<210> SEQ ID NO 49
<211> LENGTH: 809
<212> TYPE: DNA
<213> ORGANISM: Pinus radiata

<400> SEQUENCE: 49

| | | | | | |
|---|---|---|---|---|---|
| tgatatatat | aacttctagc | agaatgacac | gcgacttgta | tatcttttca | ttttttaacc | 60 |
| catgaaaacc | gattagggta | ttgcaaatta | gggcattgcc | attcaaataa | ttctcagatg | 120 |
| aaagattctc | tctaacaatt | acaaatgatt | attttttttcc | atgagtgttg | catgttcgaa | 180 |
| cggtctgccc | agtctgtgag | agagcataga | gaaccctccc | tgcccaattt | gttagagcat | 240 |
| agagaaccct | actgcatgag | tagtaagaaa | aatattcggt | ctcaattcgg | caaagaccac | 300 |
| ctcgaatgga | tgacttcaac | gacaatctca | tgatagtgtt | ctgatcagca | ccagttcacc | 360 |
| tatatatttt | atctagggtt | tagtttgcat | gtatcaatcc | tctggtgcac | taggtaattc | 420 |
| tttcccagta | tcatatatcc | ttaatactgt | tttgtctttt | aatccatggc | taccatcaga | 480 |
| acaagctcaa | agcagaataa | gggagcatca | gccatcctct | tgcttatcgc | gattgcaggg | 540 |
| ttagtaaatg | cgtgcaacgc | tgtgggtatt | gagccaatgt | gcgacactgt | ggtgtcgagt | 600 |
| cttctgaggc | ttctgccatg | caggacggct | gttgatccct | caattgccgc | cattccactt | 660 |
| ccaagctgct | gcaacgcggt | tgagtcagct | gggcttcaat | gcctctgtct | cgtcgttaac | 720 |
| ggccctcctt | ttccagggt | cgaccgcggc | ctcgcaatgc | agctgcctgc | caaatgccat | 780 |
| ctcacccttc | ctccctgtaa | cagttagtt | | | | 809 |

<210> SEQ ID NO 50
<211> LENGTH: 428
<212> TYPE: DNA
<213> ORGANISM: Eucalyptus grandis

<400> SEQUENCE: 50

| | | | | | |
|---|---|---|---|---|---|
| tttcttgtga | ctattcattt | tcctcctgat | tatccattca | agccccgaa | ggttgcattt | 60 |
| aggactaaag | ttttccaccc | aaatataaat | aacaatggaa | gtatctgcct | tgacatcttg | 120 |
| aaggaacagt | ggagtcctgc | tttgacaatc | tccaaggttt | tgctctcaat | ttgctctttg | 180 |
| ttgacggatc | caaacccaga | tgatcctctt | gtaccagaga | ttgctcatat | gtacaagact | 240 |
| gataggggca | aatatgagtc | cactgcacgg | agttggactc | agaaatatgc | aatgggttaa | 300 |
| ctttaaaaac | tatatatcag | tgatggaact | ttatccctaa | gttggaatct | cttcgaatca | 360 |
| atgacttgtt | tgcttgtaag | aaatgtttcc | ttaagataag | tggctttcct | caaaacttga | 420 |
| ttgaagtg | | | | | | 428 |

<210> SEQ ID NO 51
<211> LENGTH: 525
<212> TYPE: DNA
<213> ORGANISM: Pinus radiata

<400> SEQUENCE: 51

| | | | | | |
|---|---|---|---|---|---|
| cccttctttg | ccttcaacta | atcctgctca | tcctctcctg | ccccccattcc | caaagatggc | 60 |
| tgcacccaga | tcatccgcta | aattgggtgc | acttttggca | atactgctca | tagttgcggc | 120 |
| agcgcaggct | caagattgct | caaatgccat | ggacaaattg | gctccatgca | cttcagcagt | 180 |
| gggactgtct | agcaatggag | tgaagccctc | atctgagtgc | tgtgatgccc | tcaaaggaac | 240 |
| cagtactggc | tgcgtctgca | agtctgtgag | agcagtgata | tcacttcctg | ctaagtgcaa | 300 |
| tctcccagcc | ataacctgct | ctggatctcg | ctgaaggctc | tctgttatgg | cgattctcag | 360 |

| atcgtggatc tctttaagat tttcagcaag caagtgatag aataaattct cagattttga | 420 |
| gatatctata tagcgatttt cagtatcaga ttgtctatag tactcatata tttaagtgat | 480 |
| tgaatagcat tctccgattc cgagttggaa acacagacac aatga | 525 |

<210> SEQ ID NO 52
<211> LENGTH: 1126
<212> TYPE: DNA
<213> ORGANISM: Pinus radiata

<400> SEQUENCE: 52

| actagtgatt actatagggc acgcgtggtc gacggcccgg gctggtaaat acccaactta | 60 |
| atttaattgt tattgagcca gagagatgcg tagtcgctca tgtcacttgt gtttaccaaa | 120 |
| aagacataca taaacacctg cacctaaaag ttataatgat aacatgcata caaccctaca | 180 |
| acgtacgtag tcacatgcgg ctagaactta accccctacc acaaacatag ccacctgcac | 240 |
| ccagaagtta taataataac atacatagaa cccttacaat aaaaaaagtt atctccaatg | 300 |
| attattaatc tactgcaggc cagccatact cagcttgaac gtgaaaattc gcattgtaag | 360 |
| catggcgcca cattaaaata acctcggcaa tattttcatg tccaagtggc cggccagcca | 420 |
| cgctcctcgc actctgagaa tactctattc atccacttgt ctctgccccg caactcatat | 480 |
| aaatgtggcc aacccaagca ccatatccat gttcattaat cccctctttg ccttcaacta | 540 |
| atcctgctca tcccctcttg ccccaattcc caaagatggc tgcacccaga tcatccgcta | 600 |
| aatcggctgc acttttcgca atactgctca tagttgcggc agtacaggct gaagattgct | 660 |
| caaatgccat ggacaaattg ctccatgca cttcagcagt gggactgtct agcaatggag | 720 |
| tgaagccctc atctgagtgc tgtgatgccc tcaaaggaac cagtactggc tgcgtctgca | 780 |
| aatctgtgag agcagtgata tcacttcctg ctaagtgcaa tctcccagcc ttaacctgct | 840 |
| ctggatctcg ctgaaggctc tctgttatgg cgattctcag atcgtggatc tctttaagat | 900 |
| tttcaggaag caagtgatag aataaattct cagatgttga gatatctata tagcgatttt | 960 |
| cagtatcaga ttgtctacag taccaatata tttaagtgat tgaatggaat tctcggattc | 1020 |
| tgagatagaa atataggcac agaatgtggc cggaggaatg ttcgaattcg agaatgataa | 1080 |
| taaataataa atgattgatt tctctctgca aaaaaaaaa aaaaaa | 1126 |

<210> SEQ ID NO 53
<211> LENGTH: 454
<212> TYPE: DNA
<213> ORGANISM: Pinus radiata

<400> SEQUENCE: 53

| atcctgctca tcctctcctg cccccattcc caaagatggc tgcacccaga tcatccgcta | 60 |
| aattgggtgc acttttggca atactgctca tagttgcggc agcgcaggct caagattgct | 120 |
| caaatgccat ggacaaattg ctccatgca cttcagcagt gggactgtct agcaatggag | 180 |
| tgaagccctc atctgagtgc tgtgatgccc tcaaaggaac cagtactggc tgcgtctgca | 240 |
| agtctgtgag agcagtgata tcacttcctg ctaagtgcaa tctcccagcc ataacctgct | 300 |
| ctggatctcg ctgaaggctc tctgttatgg cgattctcag atcgtggata tctttaagat | 360 |
| tttcagcaag tgatagaata aattctcaga ttttgagata tctatatagc gattttcagt | 420 |
| atcagattgt ctatagtact catatattta agtg | 454 |

<210> SEQ ID NO 54
<211> LENGTH: 335

```
<212> TYPE: DNA
<213> ORGANISM: Pinus radiata

<400> SEQUENCE: 54
agaagcacct gttaaaaagg aggcctgctc tttgttcatg agcttataga taagccctag      60
tctgcaagga ttattgccct gtagttattt ggaagtagat cattttcaca ggcccagatg     120
cattatattc taatgcagtt gtttgttaat tgaagtgcaa atagttccaa aatgtttaca     180
tgaatcaata gtgaacaaat ccctctgttt tatatcatat tgatggatta ttcgattttt     240
tggtgacgtg gcgcgaaact gcttttcgaa ctcatgaaaa tagtaattgt tataatccat     300
aggcatgaga ttcttgttaa tcgtgcacaa ggttt                                335

<210> SEQ ID NO 55
<211> LENGTH: 336
<212> TYPE: DNA
<213> ORGANISM: Pinus radiata

<400> SEQUENCE: 55
aaaccttgtg cacgattaac aagaatctca tgcctatgga ttataacaat tactatttcc      60
atgagttcga aaagcagttt cgcgccacgt caccaaaaaa tcgaataatc catcaatatg     120
atataaaaca gagggatttg ttcactattg attcatgtaa acattttgga actatttgca     180
cttcaattaa caaacaactg cattagaata taatgcatct ggtgcctgtg aaaatgatct     240
acttccaaat aactacaggg caataatcct tgcagactag gcttatcta taagctcatg      300 aacaaagagc aggcctcctt tttaacaggt gcttct                                336

<210> SEQ ID NO 56
<211> LENGTH: 532
<212> TYPE: DNA
<213> ORGANISM: Pinus radiata

<400> SEQUENCE: 56
cgttcgttcc cttcccttc cattgttgcg tttaagccct ccaatttcct tttggcgtcc      60
cgttttgggg gctcccttga agatctcctc ttcatttcgg gatttcctgc cttcgccgcg     120
ccatttgaag ttcttttct gagagaagaa tttagacatg gctgatcgca tgttgactcg     180
aagccacagc cttcgcgagc gtttggacga gaccctctct gctcaccgca acgatattgt     240
ggccttcctt tcaagggttg aagccaaggg caaaggcatc ttgcagcgcc accagatttt     300
tgctgagttt gaggccatct ctgaggagag cagagcaaag cttcttgatg gggccttggg     360
tgaagtcctc aaatccactc aggaagcgat tgtgtcgcct ccatggggttg ctcttgctgt     420 tcgtccaagg ccgggcgtgt gggagcacat ccgtgtgaac gtccatgcgc ttgttcttga     480
gcaattggag gttgctgagt atctgcactt caaagaagag cttgctgatg ga             532

<210> SEQ ID NO 57
<211> LENGTH: 3103
<212> TYPE: DNA
<213> ORGANISM: Eucalyptus grandis

<400> SEQUENCE: 57
gggtgaaaac aattaatgag atcatttgaa ttaaggaaag tggaaaggcg gttttctgat      60
tggtacactg aaacaacagg aaggtggtgg aggccgcaat gatggaattt atccactta     120 atcattttat gaaatcgata cactaacctt tgtttctcct aaacccaaag gcattaatcc     180
ctgtcctcct cactcgatct cgaaggccag aaggggggagg ccgagcctct tgctttttt     240
```

| | |
|---|---|
| cgtgtataaa agggcctccc ccattcctca tttttcacca tcctccgttc gttcgttccc | 300 |
| ttcccttttcc attgttgcgt ttaagccctc caattttctt ttggcgtccc gttttttgggg | 360 |
| ctcccttgaa gatctcctct tcatttcggg atttcctgcc ttcgccgcgc catttgaagt | 420 |
| tcttttctg agagaagaat ttagacatgg ctgatcgcat gttgactcga agccacagcc | 480 |
| ttcgcgagcg tttggacgag accctctctg ctcaccgcaa cgatattgtg gccttccttt | 540 |
| caagggttga agccaagggc aaaggcatct gcagcgcca ccagattttt gctgagtttg | 600 |
| aggccatctc tgaggagagc agagcaaagc ttccttgatgg ggcctttggt gaagtcctca | 660 |
| aatccactca ggaagcgatt gtgtcgcctc catgggttgc tcttgctgtt cgtccaaggc | 720 |
| cgggcgtgtg ggagcacatc cgtgtgaacg tccatgcgct tgttcttgag caattggagg | 780 |
| ttgctgagta tctgcacttc aaagaagagc ttgctgatgg aagcttgaat ggtaactttg | 840 |
| tgcttgagct tgactttgag ccattcactg cctcttttcc gcgcccgact cttttccaagt | 900 |
| ctattggcaa tggcgtcgag tttctcaatc gccatctctc cgctaagctc ttccatgaca | 960 |
| aggaaagctt gcaccctctg cttgaattcc tccaagtcca ctgctacaag gggaagaaca | 1020 |
| tgatggtgaa tgccagaatc cagaatgtgt tctcctcca acatgtcctg aggaaggcgg | 1080 |
| aggagtatct gacctcgctc aaacccgaga ccccgtactc ccagttcgag cacaagttcc | 1140 |
| aggagatcgg gctcgagcgg gggtggggtg acacggctga gcgcgtcctc gagatgatcc | 1200 |
| agctcctgtt ggatctcctt gaggctcccg acccgtgcac tctcgagaag ttcttggata | 1260 |
| gggttcccat ggtcttcaac gtcgtgatca tgtctccca cggatacttt gctcaggacg | 1320 |
| acgtccttgg ttatccggat accggtggcc aggttgttta catcctggat caagttcgtg | 1380 |
| ccctagagga agaaatgctt caccgcatta agcaacaagg actggatatt actcctcgga | 1440 |
| ttctcattat cactcggctt cttccagacg cggttggaac cacctgtggc cagcgccttg | 1500 |
| agaaagtttt tgggaccgag tactcccaca ttcttcgcgt ccccttcaga aatgagaagg | 1560 |
| gagtcgtccg caagtggatt tcccggttcg aggtgtggcc ctatttggaa agatacactg | 1620 |
| aggatgtcgc gagcgaactt gctggagagt tgcagggcaa gcctgatctg atcatcggaa | 1680 |
| actacagtga tggaaacatt gttgcttcct tgttagcaca taaattaggt gttacacagt | 1740 |
| gtacaatagc ccatgccctc gagaagacga agtacccaga gtcagacata tactggaaga | 1800 |
| aatttgagga aaagtaccac ttctcttgcc agttcactgc tgatctcatc gccatgaacc | 1860 |
| acaccgactt cattatcacc agcaccttcc aagaaattgc tggaagcaag gatacagtgg | 1920 |
| ggcagtatga gagtcacatg aacttcactc ttcctggact ctaccgagtt gtccacggga | 1980 |
| tcgacgtctt cgacccgaag ttcaacattg tttcaccagg tgctgacatg agcatctact | 2040 |
| ttgcttacac cgaacaggag cggcggttga atccttcca ccctgagatc gaggaactcc | 2100 |
| tcttcagcga tgttgagaac aaggaacact tgtgtgtgtt gaaagataag aagaagccta | 2160 |
| ttattttcac catggcaagg ctggaccgtg tcaagaactt gacagggctt gttgagtggt | 2220 |
| atggcaagaa ctccaagttg agggaactcg ccaacttggt cgtggttgga ggtgacagga | 2280 |
| ggaaggattc gaaggacttg gaagagcagt ctgagatgaa gaaaatgtac gacctcatcg | 2340 |
| aaaagtacaa gctgaatggc cagttcaggt ggatttcctc ccagatgaac cgggtgagga | 2400 |
| atggagagct ctaccgctac atctgtgaca cgaagggagt cttcgttcaa ccggctatct | 2460 |
| atgaagcttt cggggttgacc gtggttgagg ccatgacttg tggattgcca acctttgcca | 2520 |
| cttgcaatgg tggaccagct gagatcattg tgcatggcaa atcgggctac acattgatc | 2580 |
| cttaccatgg tgaccaggcg gccgagcttc ttgtagactt cttcaacaag tgcaagattg | 2640 |

-continued

```
accagtccca ctgggacgag atctcaaagg gtgccatgca gagaattgaa gagaagtata    2700
catggaaaat atattctgag aggctgttga acctgactgc cgtgtatggc ttctggaagc    2760
atgtgactaa ccttgatcgg cgcgagagtc gccggtacct tgaaatgttc tatgccctca    2820
agtatcgccc actggcacag tctgttcctc cggctgtcga gtaaacaaag agacagattg    2880
ttaccagaag acgaagcat  tggacttttg aagttttcaa ggaataaaca ttggaaattg    2940
tttgaatttg ggattgccaa gagcgatctt tttcgtttcc ttttttttggt ccttttctc    3000 ttctttgttt ccattccgcg aatgtttgca ttttgggggtt tgtacccatc aattcagtaa    3060
atggttcatt ttcttttcaa aaaaaaaaaa aaaaaaaaa aaa                       3103
```

<210> SEQ ID NO 58
<211> LENGTH: 326
<212> TYPE: DNA
<213> ORGANISM: Eucalyptus grandis

<400> SEQUENCE: 58

```
ctcgaaaccg agacgctgac tgtgggttga gctctaacca atgggagtga tgtctctctt     60
acgtgcctgc cgtgggcccc agtgacgggc cccaaaagtg taaacgaagg aagctcccgg    120
ggatctgatt ggccgcgacg tccgcctctg acgtggcacc accgacgatt ttttttttaat    180 atcttggtca agtcctaatt taactatggg gtccagatta gaagcttatc cactatggat    240
taaattaaat caaatgggaa ttaaattaaa ttaaaatcat cgtgcggagg tgcacgagat    300
gcacgagatc cgacggcgca gagcag                                         326
```

<210> SEQ ID NO 59
<211> LENGTH: 311
<212> TYPE: DNA
<213> ORGANISM: Eucalyptus grandis

<400> SEQUENCE: 59

```
attactatag ggcacgcgtg gtcgacggcc cgggctggta ctctcactaa ttctttagtt     60
ttccaattta gcccttctg taattgctca tcttcttac caaattctct aatttggccg     120
gcgaagggct gacaagggat tggtcatgtc accctcacca aaggttgccg aaggtccggt    180
gacctcagct gacggccacc tacaccaaat ctagctcact agcagcctaa gcccttcatc    240
aactctagtg aaaggttttg agtattttttt aataaaaaat atttaaaaaa tatatagcga    300
gagctcatta c                                                         311
```

<210> SEQ ID NO 60
<211> LENGTH: 2096
<212> TYPE: DNA
<213> ORGANISM: Eucalyptus grandis

<400> SEQUENCE: 60

```
gattactata gggcacgcgt ggtcgacggc ccgggctggt ctgagccatt taattcgaga     60
gcacatcgcc caaaattatt cttcttgctg ccataactgt cgaatttttct cttttaggta    120 agtaaccaat gatgcatcat gttgacaaaa aggctgatta gtatgatctt ggagttgttg    180
gtgcaaattt gcaagctgac gatggcccct cagggaaatt aaggcgccaa cccagattgc    240
aaagagcaca agagcacga tccaaccttt ccttaacaag atcatcacca gatcggccag    300
taagggtaat attaatttaa caaatagctc ttgtaccggg aactccgtat ttctctcact    360
tccataaacc cctgattaat ttggtgggaa agcgacagcc aacccacaaa aggtcagatg    420
```

-continued

```
tcatcccacg agagagagag agagagagag agagagagag agagtttttct ctctatattc    480
tggttcaccg gttggagtca atggcatgcg tgacgaatgt acatattggt gtagggtcca    540
atattttgcg ggagggttgg tgaaccgcaa agttcctata tatcgaacct ccaccaccat    600
acctcacttc aatccccacc atttatccgt tttatttcct ctgctttcct ttgctcgagt    660
ctcgcggaag agagagaaga gaggagagga gagaatgggc tcgaccggat ccagacccca    720
gatgaccccg acccaagtct cggacgagga ggcgaacctc ttcgccatgc agctggcgag    780
cgcctccgtg ctccccatgg tcctcaaggc cgccatcgag ctcgacctcc tcgagatcat    840
ggccaaggcc gggccgggcg cgttcctctc cccgggggaa gtcgcggccc agctcccgac    900
ccagaacccc gaggcacccg tcatgctcga ccggatcttc cggctgctgg ccagctactc    960
cgtgctcacg tgcaccctcc gcgacctccc cgatggcaag gtcgagcggc tctacggctt   1020
agcgccggtg tgcaagttct tggtcaagaa cgaggacggg gtctccatcg ccgcactcaa   1080
cttgatgaac caggacaaaa tcctcatgga aagctggtat tacctgaaag atgcggtcct   1140
tgaaggcgga atcccattca acaaggcgta cgggatgacc gcgttcgagt atcatggcac   1200
cgacccgcga ttcaacaaga tctttaaccg gggaatgtct gatcactcca ccattactat   1260
gaagaagata ctggaaacat acaagggctt cgagggcctc gagaccgtgg tcgatgtcgg   1320
aggcggcact ggggccgtgc tcagcatgat cgttgccaaa tacccatcaa tgaaagggat   1380
caacttcgac cgccccaacg gattgaagac gccccacccc ttcctggtgt caagcacgtc   1440
ggaggcgaca tgttcgtcag cgttccaaag ggagatgcca ttttcatgaa gtggatatgc   1500
catgactgga gtgacgacca ttgcgcgaag ttcctcaaga actgctacga tgcgcttccc   1560
aacaatggaa aggtgatcgt tgcagagtgc gtactccctg tgtacccaga cacgagccta   1620
gcgaccaaga atgtgatcca catcgactgc atcatgttgg cccacaaccc aggcgggaaa   1680
gagaggacac agaaggagtt cgaggcattg gccaaggggg ccggatttca gggcttccaa   1740
gtcatgtgct gcgctttcgg cactcacgtc atggagttcc tgaagaccgc ttgatctgct   1800
cctctgtggt gatgttcatg gttcttggat ttgaaaggtc gtgaaggagc cttttctca   1860
cagttggctt cggcatacca agttcttctc ataaaaggaa acaataagaa gcgactgtat   1920
gatggcgcaa gtgaagtta caagatttgt tgttttatgt ctataaagtt ttgagtcttc   1980
tgcatactga tttcacagaa tgtgtaacga aacggcgtat atggatgtgc ctgaatgatg   2040
gaaattgtga tattctgtct tcttttttcag taaatcactt cgaacaaaaa aaaaaa      2096
```

<210> SEQ ID NO 61
<211> LENGTH: 522
<212> TYPE: DNA
<213> ORGANISM: Eucalyptus grandis

<400> SEQUENCE: 61

```
ctaaaacgct aatcctgccc tgcccttccc ttctgctgct gctgctcgtc acctctctct     60
ccctctcgcg gccagctgcg agatctgccg agtttaagcc tcgtacatca aaatgggtaa    120
ggagaagatt cacatcagca ttgtggtcat tggccatgtc gattctggga agtcaaccac    180
aactggccac ttgatataca agctcggagg aatcgacaag cgtgtgattg agagattcga    240
gaaggaagct gctgagatga acaagagatc gttcaagtat gcttgggtgc ttgacaagct    300
caaggccgag cgcgagcgcg gtattaccat tgatattgcc ttgtggaagt tcgagaccac    360
caagtactac tgcactgtca ttgatgctcc tggacatcgt gactttatta agaatatgat    420
tactggaacc tcccaggccg actgtgctgt ccttatcatt gattccacca ctggtggttt    480
```

```
cgaagctggt atttccaagg atggccagac ccgtgaacat gc               522
```

<210> SEQ ID NO 62
<211> LENGTH: 420
<212> TYPE: DNA
<213> ORGANISM: Eucalyptus grandis

<400> SEQUENCE: 62

```
tttgatacgc taacaaacaa aacatgtgaa aagcttaatt atggcaatta tcataaatag    60
aaaaaaatta gaaaaaaga gaggaaatgg gccattattt aaattgcaat cgaaagattg   120
agggcaattc tgtttctcta gtgtaaataa gggtgtattt ataattgag ggatggaaat    180
agcatggtca ctcggtaatt atcaaggaaa gcaagaataa aaatgaaaa aaaaaaaaa    240
aaagcttgaa gaggccaatg tcgaaattat gagcgcgaga tgaggacact cctgggaaac   300
gaaaaatggc attcgcgggg ggtgctatat aaagcctcgt gtaagggtgc gttcctcact   360
ctcaaaccct aatcctgccc ttccttctg ctgctgctgc tcgtcacctc tctcctccct    420
```

<210> SEQ ID NO 63
<211> LENGTH: 65
<212> TYPE: PRT
<213> ORGANISM: Eucalyptus grandis

<400> SEQUENCE: 63

```
Met Asp Asn Ser Lys Met Gly Phe Asn Ala Gly Gln Ala Lys Gly Gln
 1               5                  10                  15

Thr Gln Glu Lys Ser Asn Gln Met Met Asp Lys Ala Ser Asn Thr Ala
            20                  25                  30

Gln Ser Ala Arg Asp Ser Met Gln Glu Thr Gly Gln Gln Met Lys Ala
        35                  40                  45

Lys Ala Gln Gly Ala Ala Asp Ala Val Lys Asn Ala Thr Gly Met Asn
    50                  55                  60

Lys
65
```

<210> SEQ ID NO 64
<211> LENGTH: 152
<212> TYPE: PRT
<213> ORGANISM: Eucalyptus grandis

<400> SEQUENCE: 64

```
Met Gly Gly Pro Leu Thr Leu Asp Ala Glu Val Glu Val Lys Ser Pro
 1               5                  10                  15

Ala Asp Lys Phe Trp Val Ser Val Arg Asp Ser Thr Lys Leu Phe Pro
            20                  25                  30

Lys Ile Phe Pro Asp Gln Tyr Lys Asn Ile Glu Val Leu Glu Gly Asp
        35                  40                  45

Gly Lys Ala Pro Gly Ser Val Arg Leu Phe Thr Tyr Gly Glu Gly Ser
    50                  55                  60

Pro Leu Val Lys Val Ser Lys Glu Lys Ile Asp Gly Val Asp Glu Ala
65                  70                  75                  80

Asp Lys Val Val Thr Tyr Ser Val Ile Asp Gly Asp Leu Leu Lys Tyr
                85                  90                  95

Tyr Lys Asn Phe Asn Gly Ser Ile Lys Val Ile Pro Lys Gly Asp Gly
                100                 105                 110

Ser Leu Val Lys Trp Ser Cys Gly Phe Glu Lys Ala Ser Asp Glu Ile
            115                 120                 125
```

```
Pro Asp Pro His Val Ile Lys Asp Phe Ala Ile Gln Asn Phe Lys Glu
        130                 135                 140

Leu Asp Glu Phe Ile Leu Lys Ala
145                 150

<210> SEQ ID NO 65
<211> LENGTH: 117
<212> TYPE: PRT
<213> ORGANISM: Eucalyptus grandis

<400> SEQUENCE: 65

Met Ala Ala Asn Phe Val Ile Pro Thr Lys Met Lys Ala Trp Val Tyr
1               5                   10                  15

Arg Glu His Gly Asn Val Ala Asp Val Leu Gly Leu Asp Pro Glu Leu
                20                  25                  30

Lys Val Pro Glu Leu Gln Glu Gly Gln Val Leu Val Lys Val Leu Ala
            35                  40                  45

Ala Ala Leu Asn Pro Val Asp Ala Ala Arg Met Lys Gly Val Ile Lys
        50                  55                  60

Leu Pro Gly Phe Ser Leu Pro Ala Val Pro Gly Tyr Asp Leu Ala Gly
65                  70                  75                  80

Val Val Val Lys Val Gly Arg Glu Val Lys Glu Leu Lys Ile Gly Asp
                85                  90                  95

Glu Val Tyr Gly Phe Met Phe His Ala Lys Lys Asp Gly Thr Leu Ala
                100                 105                 110

Glu Tyr Ala Ala Val
        115

<210> SEQ ID NO 66
<211> LENGTH: 318
<212> TYPE: PRT
<213> ORGANISM: Eucalyptus grandis

<400> SEQUENCE: 66

Met Ala Ala Asn Phe Val Ile Pro Thr Lys Met Lys Ala Trp Val Tyr
1               5                   10                  15

Arg Glu His Gly Asp Val Ala Asn Val Leu Gly Leu Asp Pro Glu Leu
                20                  25                  30

Lys Val Pro Glu Leu Gln Glu Gly Gln Val Leu Val Lys Val Leu Ala
            35                  40                  45

Ala Ala Leu Asn Pro Ile Asp Thr Ala Arg Val Lys Gly Val Ile Lys
        50                  55                  60

Leu Pro Gly Phe Ser Leu Pro Ala Val Pro Gly Tyr Asp Leu Ala Gly
65                  70                  75                  80

Val Val Val Lys Val Gly Arg Glu Val Lys Glu Leu Lys Val Gly Asp
                85                  90                  95

Glu Val Tyr Gly Phe Met Phe His Ala Lys Lys Asp Gly Thr Leu Ala
                100                 105                 110

Glu Tyr Ala Ala Val Glu Glu Ser Phe Leu Ala Leu Lys Pro Lys Lys
            115                 120                 125

Leu Arg Phe Gly Glu Ala Ala Ser Leu Pro Val Val Ile Gln Thr Ala
        130                 135                 140

Tyr Gly Gly Leu Glu Arg Ala Gly Leu Ser His Gly Lys Ser Leu Leu
145                 150                 155                 160

Val Leu Gly Gly Ala Gly Gly Val Gly Thr Leu Ile Ile Gln Leu Ala
                165                 170                 175
```

Lys Glu Val Phe Gly Ala Ser Arg Val Ala Ala Thr Ser Ser Thr Gly
            180                 185                 190

Lys Leu Glu Leu Leu Lys Ser Leu Gly Ala Asp Leu Ala Ile Asp Tyr
        195                 200                 205

Thr Lys Val Asn Phe Glu Asp Leu Pro Glu Lys Phe Asp Val Val Tyr
    210                 215                 220

Asp Thr Val Gly Glu Ile Glu Arg Ala Ala Lys Ala Val Lys Pro Gly
225                 230                 235                 240

Gly Ser Ile Val Thr Ile Val Lys Gln Asn Lys Thr Leu Pro Pro Pro
                245                 250                 255

Ala Phe Phe Ala Val Thr Ser Asn Arg Ser Thr Leu Glu Lys Leu
        260                 265                 270

Lys Pro Phe Leu Glu Ser Gly Lys Val Lys Pro Val Ile Asp Pro Lys
        275                 280                 285

Ser Pro Phe Pro Phe Ser Gln Ala Ile Glu Ala Phe Ser Tyr Leu Gln
        290                 295                 300

Thr Arg Arg Ala Thr Gly Lys Leu Val Ile His Pro Val Pro
305                 310                 315

<210> SEQ ID NO 67
<211> LENGTH: 156
<212> TYPE: PRT
<213> ORGANISM: Eucalyptus grandis

<400> SEQUENCE: 67

Met Gln Ile Phe Val Lys Thr Leu Thr Gly Lys Thr Ile Thr Leu Glu
1               5                   10                  15

Val Glu Ser Ser Asp Thr Val Asp Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ala Asp Tyr Asn Ile Gln Lys Glu
    50                  55                  60

Ser Thr Leu His Leu Val Leu Arg Leu Arg Gly Gly Met Gln Ile Phe
65                  70                  75                  80

Val Lys Thr Leu Thr Gly Lys Thr Ile Thr Leu Glu Val Glu Ser Ser
                85                  90                  95

Asp Thr Val Asp Asn Val Lys Ala Lys Ile Gln Asp Lys Glu Gly Ile
            100                 105                 110

Pro Pro Asp Gln Gln Arg Leu Ile Phe Ala Gly Lys Gln Leu Glu Asp
        115                 120                 125

Gly Arg Thr Leu Ala Asp Tyr Asn Ile Gln Lys Glu Ser Thr Leu His
130                 135                 140

Leu Val Leu Arg Leu Lys Gly Gly Met Gln Ile Phe
145                 150                 155

<210> SEQ ID NO 68
<211> LENGTH: 238
<212> TYPE: PRT
<213> ORGANISM: Eucalyptus grandis

<400> SEQUENCE: 68

Met Ala Thr His Ala Ala Leu Ala Pro Ser Thr Leu Pro Ala Asn Ala
1               5                   10                  15

Lys Phe Ser Ser Lys Ser Ser Ser His Ser Phe Pro Thr Gln Cys Phe
            20                  25                  30

```
Ser Lys Arg Leu Glu Val Ala Glu Phe Ser Gly Leu Arg Ala Gly Ser
         35                  40                  45

Cys Val Thr Tyr Ala Lys Asn Ala Gly Glu Gly Ser Phe Phe Asp Ala
 50                      55                  60

Val Ala Ala Gln Leu Thr Pro Lys Thr Ser Ala Pro Ala Pro Ala Lys
 65                  70                  75                  80

Gly Glu Thr Val Ala Lys Leu Lys Val Ala Ile Asn Gly Phe Gly Arg
                 85                  90                  95

Ile Gly Arg Asn Phe Leu Arg Cys Trp His Gly Arg Lys Asn Ser Pro
            100                 105                 110

Leu Asp Val Ile Val Asn Asp Ser Gly Gly Val Lys Asn Ala Ser
            115                 120                 125

His Leu Leu Lys Tyr Asp Ser Met Leu Gly Thr Phe Lys Ala Asp Val
        130                 135                 140

Lys Ile Val Asp Asn Glu Thr Ile Ser Val Asp Gly Lys Pro Val Lys
145                 150                 155                 160

Val Val Ser Asn Arg Asp Pro Leu Lys Leu Pro Trp Ala Glu Leu Gly
                165                 170                 175

Ile Asp Ile Val Ile Glu Gly Thr Gly Val Phe Val Asp Gly Pro Gly
            180                 185                 190

Ala Gly Lys His Ile Gln Ala Gly Ala Lys Lys Val Ile Ile Thr Ala
        195                 200                 205

Pro Ala Lys Gly Ala Asp Ile Pro Thr Tyr Val Tyr Gly Val Asn Glu
    210                 215                 220

Thr Asp Tyr Ser His Glu Val Ala Asn Ile Ile Ser Asn Ala
225                 230                 235

<210> SEQ ID NO 69
<211> LENGTH: 168
<212> TYPE: PRT
<213> ORGANISM: Eucalyptus grandis

<400> SEQUENCE: 69

Met Ser Thr Ser Pro Val Ser Ser Trp Cys Ala Thr Ser Phe Ser Pro
 1               5                  10                  15

Ala His Ser Ser Leu Lys Arg Ala Ala Gly Leu Arg Pro Ser Leu Ser
                 20                  25                  30

Ala Arg Leu Gly Pro Ser Ser Ser Ser Ser Val Ser Pro Pro Thr
         35                  40                  45

Leu Ile Arg Asn Glu Pro Val Phe Ala Ala Pro Ala Pro Val Ile Asn
 50                      55                  60

Pro Thr Trp Thr Glu Glu Met Gly Lys Asp Tyr Asp Glu Ala Ile Glu
 65                  70                  75                  80

Ala Leu Lys Lys Leu Leu Ser Glu Lys Gly Asp Leu Lys Ala Thr Ala
                 85                  90                  95

Ala Ala Lys Val Glu Gln Ile Thr Ala Glu Leu Gln Thr Ala Ser Pro
            100                 105                 110

Asp Ile Lys Pro Ser Ser Ser Val Asp Arg Ile Lys Thr Gly Phe Thr
        115                 120                 125

Phe Phe Lys Lys Glu Lys Tyr Asp Lys Asn Pro Ala Leu Tyr Gly Glu
    130                 135                 140

Leu Ala Lys Gln Ser Pro Lys Phe Met Val Phe Ala Cys Ser Asp Ser
145                 150                 155                 160

Arg Val Cys Pro Ser His Val Leu
```

-continued

```
                165

<210> SEQ ID NO 70
<211> LENGTH: 214
<212> TYPE: PRT
<213> ORGANISM: Eucalyptus grandis

<400> SEQUENCE: 70

Met Pro Cys Pro Arg Ala Pro Pro Met Met Glu Arg Arg Ile Lys Pro
  1               5                  10                  15

Gln Thr Glu Gln Ala Leu Lys Cys Pro Arg Cys Asp Ser Thr Asn Thr
             20                  25                  30

Lys Phe Cys Tyr Tyr Asn Asn Tyr Asn Leu Ser Gln Pro Arg His Phe
         35                  40                  45

Cys Lys Thr Cys Arg Arg Tyr Trp Thr Lys Gly Gly Ala Leu Arg Asn
 50                  55                  60

Val Pro Val Gly Gly Cys Arg Lys Asn Lys Arg Ala Lys Arg Ala
 65                  70                  75                  80

Val Asp His Pro Val Ser Ala Gln Asn Glu Ala Ser Thr Ser Ala Ala
                 85                  90                  95

Pro Gly Asn Glu Val Pro Asp Arg Ser Pro Phe Glu Pro Pro Ser Ser
            100                 105                 110

Lys Ser Ile Tyr Tyr Gly Gly Glu Asn Met Asn Leu Thr Gly Leu Pro
        115                 120                 125

Phe Ser Arg Ile Gln Gln Asp Arg Ala Ala Leu Ala His Cys Asn Ser
    130                 135                 140

Ser Ser Phe Leu Gly Met Ser Cys Gly Thr Gln Ser Ala Ser Leu Glu
145                 150                 155                 160

Pro His Leu Ser Ala Leu Asn Thr Phe Asn Ser Phe Lys Ser Asn Asn
                165                 170                 175

Pro Gly Leu Asp Phe Pro Ser Leu Ser Thr Asp Gln Asn Ser Leu Phe
            180                 185                 190

Glu Thr Ser Gln Pro Gln Leu Ser Arg Ala Met Ala Ser Ala Leu Phe
        195                 200                 205

Ser Met Pro Met Ala Pro
    210

<210> SEQ ID NO 71
<211> LENGTH: 166
<212> TYPE: PRT
<213> ORGANISM: Pinus radiata

<400> SEQUENCE: 71

Met Ala Ala Leu Ala Thr Thr Glu Val Cys Asp Thr Tyr Pro Arg Leu
  1               5                  10                  15

Val Glu Asn Gly Glu Leu Arg Val Leu Gln Pro Ile Phe Gln Ile Tyr
             20                  25                  30

Gly Arg Arg Arg Ala Phe Ser Gly Pro Ile Val Thr Leu Lys Val Phe
         35                  40                  45

Glu Asp Asn Val Leu Leu Arg Glu Phe Leu Glu Glu Arg Gly Asn Gly
 50                  55                  60

Arg Val Leu Val Val Asp Gly Gly Gly Ser Leu Arg Cys Ala Ile Leu
 65                  70                  75                  80

Gly Gly Asn Val Val Val Ser Ala Gln Asn Asn Gly Trp Ser Gly Ile
                 85                  90                  95

Ile Val Thr Gly Cys Ile Arg Asp Val Asp Glu Ile Asn Arg Cys Asp
```

```
                         100                 105                 110
Ile Gly Ile Arg Ala Leu Thr Ser Asn Pro Leu Lys Ala Asn Lys Lys
            115                 120                 125
Gly Val Gly Glu Lys His Ala Pro Ile Tyr Ile Ala Gly Thr Arg Ile
    130                 135                 140
Leu Pro Gly Glu Trp Cys Tyr Ala Asp Ser Asp Gly Ile Leu Val Ser
145                 150                 155                 160
Gln Gln Glu Leu Ser Leu
                165

<210> SEQ ID NO 72
<211> LENGTH: 236
<212> TYPE: PRT
<213> ORGANISM: Pinus radiata

<400> SEQUENCE: 72

Met Leu Val Leu Ile Ile Phe Gly Cys Cys Phe Ile Gly Val Ile Ala
1               5                   10                  15
Thr Ser Phe Asp Phe Tyr Tyr Phe Val Gln Gln Trp Pro Gly Ser Tyr
            20                  25                  30
Cys Asp Thr Arg Arg Gly Cys Cys Tyr Pro Arg Thr Gly Arg Pro Ala
        35                  40                  45
Ser Glu Phe Ser Ile His Gly Leu Trp Pro Asn Tyr Lys Thr Gly Lys
    50                  55                  60
Trp Pro Gln Phe Cys Gly Ser Glu Glu Phe Asp Tyr Ser Lys Ile
65                  70                  75                  80
Ser Asp Leu Glu Glu Glu Leu Asn Arg Tyr Trp Gly Ser Leu Ser Cys
                85                  90                  95
Pro Ser Ser Asp Gly Gln Glu Phe Trp Gly His Glu Trp Glu Lys His
            100                 105                 110
Gly Thr Cys Ser Leu Asn Leu Asp Glu His Ser Tyr Phe Glu Lys Ala
        115                 120                 125
Leu Ser Leu Arg Gln Asn Ile Asp Ile Leu Gly Ala Leu Lys Thr Ala
    130                 135                 140
Gly Ile Lys Pro Asp Gly Ser Gln Tyr Ser Leu Ser Asp Ile Lys Glu
145                 150                 155                 160
Ala Ile Lys Gln Asn Thr Gly Gln Leu Pro Gly Ile Asp Cys Asn Thr
                165                 170                 175
Ser Ala Glu Gly Glu His Gln Leu Tyr Gln Val Tyr Val Cys Val Asp
            180                 185                 190
Lys Ser Asp Ala Ser Thr Val Ile Glu Cys Pro Ile Tyr Pro His Ser
        195                 200                 205
Asn Cys Pro Ser Met Val Val Phe Pro Pro Phe Gly Glu Asp Gln Glu
    210                 215                 220
Asp Arg Asp Gly Tyr Thr Glu Gly Met Tyr Glu Leu
225                 230                 235

<210> SEQ ID NO 73
<211> LENGTH: 92
<212> TYPE: PRT
<213> ORGANISM: Pinus radiata

<400> SEQUENCE: 73

Met Ala Ala Pro Arg Ser Ser Ala Lys Leu Gly Ala Leu Leu Ala Ile
1               5                   10                  15
Leu Leu Ile Val Ala Ala Ala Gln Ala Gln Asp Cys Ser Asn Ala Met
```

-continued

```
                    20                  25                  30

Asp Lys Leu Ala Pro Cys Thr Ser Ala Val Gly Leu Ser Ser Asn Gly
                35                  40                  45

Val Lys Pro Ser Ser Glu Cys Cys Asp Ala Leu Lys Gly Thr Ser Thr
 50                      55                  60

Gly Cys Val Cys Lys Ser Val Arg Ala Val Ile Ser Leu Pro Ala Lys
 65                  70                  75                  80

Cys Asn Leu Pro Ala Ile Thr Cys Ser Gly Ser Arg
                85                  90

<210> SEQ ID NO 74
<211> LENGTH: 92
<212> TYPE: PRT
<213> ORGANISM: Pinus radiata

<400> SEQUENCE: 74

Met Ala Ala Pro Arg Ser Ser Ala Lys Ser Ala Ala Leu Phe Ala Ile
 1               5                  10                  15

Leu Leu Ile Val Ala Ala Val Gln Ala Glu Asp Cys Ser Asn Ala Met
                20                  25                  30

Asp Lys Leu Ala Pro Cys Thr Ser Ala Val Gly Leu Ser Ser Asn Gly
                35                  40                  45

Val Lys Pro Ser Ser Glu Cys Cys Asp Ala Leu Lys Gly Thr Ser Thr
 50                      55                  60

Gly Cys Val Cys Lys Ser Val Arg Ala Val Ile Ser Leu Pro Ala Lys
 65                  70                  75                  80

Cys Asn Leu Pro Ala Leu Thr Cys Ser Gly Ser Arg
                85                  90

<210> SEQ ID NO 75
<211> LENGTH: 92
<212> TYPE: PRT
<213> ORGANISM: Pinus radiata

<400> SEQUENCE: 75

Met Ala Ala Pro Arg Ser Ser Ala Lys Leu Gly Ala Leu Leu Ala Ile
 1               5                  10                  15

Leu Leu Ile Val Ala Ala Gln Ala Gln Asp Cys Ser Asn Ala Met
                20                  25                  30

Asp Lys Leu Ala Pro Cys Thr Ser Ala Val Gly Leu Ser Ser Asn Gly
                35                  40                  45

Val Lys Pro Ser Ser Glu Cys Cys Asp Ala Leu Lys Gly Thr Ser Thr
 50                      55                  60

Gly Cys Val Cys Lys Ser Val Arg Ala Val Ile Ser Leu Pro Ala Lys
 65                  70                  75                  80

Cys Asn Leu Pro Ala Ile Thr Cys Ser Gly Ser Arg
                85                  90

<210> SEQ ID NO 76
<211> LENGTH: 125
<212> TYPE: PRT
<213> ORGANISM: Eucalyptus grandis

<400> SEQUENCE: 76

Met Ala Asp Arg Met Leu Thr Arg Ser His Ser Leu Arg Glu Arg Leu
 1               5                  10                  15

Asp Glu Thr Leu Ser Ala His Arg Asn Asp Ile Val Ala Phe Leu Ser
                20                  25                  30
```

-continued

```
Arg Val Glu Ala Lys Gly Lys Gly Ile Leu Gln Arg His Gln Ile Phe
         35                  40                  45

Ala Glu Phe Glu Ala Ile Ser Glu Ser Arg Ala Lys Leu Leu Asp
     50                  55                  60

Gly Ala Phe Gly Glu Val Leu Lys Ser Thr Gln Glu Ala Ile Val Ser
 65                  70                  75                  80

Pro Pro Trp Val Ala Leu Ala Val Arg Pro Arg Pro Gly Val Trp Glu
                 85                  90                  95

His Ile Arg Val Asn Val His Ala Leu Val Leu Glu Gln Leu Glu Val
                100                 105                 110

Ala Glu Tyr Leu His Phe Lys Glu Glu Leu Ala Asp Gly
        115                 120                 125

<210> SEQ ID NO 77
<211> LENGTH: 805
<212> TYPE: PRT
<213> ORGANISM: Eucalyptus grandis

<400> SEQUENCE: 77

Met Ala Asp Arg Met Leu Thr Arg Ser His Ser Leu Arg Glu Arg Leu
 1               5                  10                  15

Asp Glu Thr Leu Ser Ala His Arg Asn Asp Ile Val Ala Phe Leu Ser
             20                  25                  30

Arg Val Glu Ala Lys Gly Lys Gly Ile Leu Gln Arg His Gln Ile Phe
         35                  40                  45

Ala Glu Phe Glu Ala Ile Ser Glu Ser Arg Ala Lys Leu Leu Asp
     50                  55                  60

Gly Ala Phe Gly Glu Val Leu Lys Ser Thr Gln Glu Ala Ile Val Ser
 65                  70                  75                  80

Pro Pro Trp Val Ala Leu Ala Val Arg Pro Arg Pro Gly Val Trp Glu
                 85                  90                  95

His Ile Arg Val Asn Val His Ala Leu Val Leu Glu Gln Leu Glu Val
                100                 105                 110

Ala Glu Tyr Leu His Phe Lys Glu Glu Leu Ala Asp Gly Ser Leu Asn
        115                 120                 125

Gly Asn Phe Val Leu Glu Leu Asp Phe Glu Pro Phe Thr Ala Ser Phe
    130                 135                 140

Pro Arg Pro Thr Leu Ser Lys Ser Ile Gly Asn Gly Val Glu Phe Leu
145                 150                 155                 160

Asn Arg His Leu Ser Ala Lys Leu Phe His Asp Lys Glu Ser Leu His
                165                 170                 175

Pro Leu Leu Glu Phe Leu Gln Val His Cys Tyr Lys Gly Lys Asn Met
                180                 185                 190

Met Val Asn Ala Arg Ile Gln Asn Val Phe Ser Leu Gln His Val Leu
        195                 200                 205

Arg Lys Ala Glu Glu Tyr Leu Thr Ser Leu Lys Pro Glu Thr Pro Tyr
    210                 215                 220

Ser Gln Phe Glu His Lys Phe Gln Glu Ile Gly Leu Glu Arg Gly Trp
225                 230                 235                 240

Gly Asp Thr Ala Glu Arg Val Leu Glu Met Ile Gln Leu Leu Leu Asp
                245                 250                 255

Leu Leu Glu Ala Pro Asp Pro Cys Thr Leu Glu Lys Phe Leu Asp Arg
            260                 265                 270

Val Pro Met Val Phe Asn Val Val Ile Met Ser Pro His Gly Tyr Phe
```

-continued

```
                275                 280                 285
Ala Gln Asp Asp Val Leu Gly Tyr Pro Asp Thr Gly Gly Gln Val Val
290                 295                 300
Tyr Ile Leu Asp Gln Val Arg Ala Leu Glu Glu Met Leu His Arg
305                 310                 315                 320
Ile Lys Gln Gln Gly Leu Asp Ile Thr Pro Arg Ile Leu Ile Thr
                325                 330                 335
Arg Leu Leu Pro Asp Ala Val Gly Thr Thr Cys Gly Gln Arg Leu Glu
                340                 345                 350
Lys Val Phe Gly Thr Glu Tyr Ser His Ile Leu Arg Val Pro Phe Arg
                355                 360                 365
Asn Glu Lys Gly Val Val Arg Lys Trp Ile Ser Arg Phe Glu Val Trp
370                 375                 380
Pro Tyr Leu Glu Arg Tyr Thr Glu Asp Val Ala Ser Glu Leu Ala Gly
385                 390                 395                 400
Glu Leu Gln Gly Lys Pro Asp Leu Ile Ile Gly Asn Tyr Ser Asp Gly
                405                 410                 415
Asn Ile Val Ala Ser Leu Leu Ala His Lys Leu Gly Val Thr Gln Cys
                420                 425                 430
Thr Ile Ala His Ala Leu Glu Lys Thr Lys Tyr Pro Glu Ser Asp Ile
                435                 440                 445
Tyr Trp Lys Lys Phe Glu Glu Lys Tyr His Phe Ser Cys Gln Phe Thr
450                 455                 460
Ala Asp Leu Ile Ala Met Asn His Thr Asp Phe Ile Ile Thr Ser Thr
465                 470                 475                 480
Phe Gln Glu Ile Ala Gly Ser Lys Asp Thr Val Gly Gln Tyr Glu Ser
                485                 490                 495
His Met Asn Phe Thr Leu Pro Gly Leu Tyr Arg Val Val His Gly Ile
                500                 505                 510
Asp Val Phe Asp Pro Lys Phe Asn Ile Val Ser Pro Gly Ala Asp Met
                515                 520                 525
Ser Ile Tyr Phe Ala Tyr Thr Glu Gln Glu Arg Arg Leu Lys Ser Phe
530                 535                 540
His Pro Glu Ile Glu Glu Leu Leu Phe Ser Asp Val Glu Asn Lys Glu
545                 550                 555                 560
His Leu Cys Val Leu Lys Asp Lys Lys Pro Ile Ile Phe Thr Met
                565                 570                 575
Ala Arg Leu Asp Arg Val Lys Asn Leu Thr Gly Leu Val Glu Trp Tyr
                580                 585                 590
Gly Lys Asn Ser Lys Leu Arg Glu Leu Ala Asn Leu Val Val Val Gly
                595                 600                 605
Gly Asp Arg Arg Lys Asp Ser Lys Asp Leu Glu Glu Gln Ser Glu Met
610                 615                 620
Lys Lys Met Tyr Asp Leu Ile Glu Lys Tyr Lys Leu Asn Gly Gln Phe
625                 630                 635                 640
Arg Trp Ile Ser Ser Gln Met Asn Arg Val Arg Asn Gly Glu Leu Tyr
                645                 650                 655
Arg Tyr Ile Cys Asp Thr Lys Gly Val Phe Val Gln Pro Ala Ile Tyr
                660                 665                 670
Glu Ala Phe Gly Leu Thr Val Val Glu Ala Met Thr Cys Gly Leu Pro
                675                 680                 685
Thr Phe Ala Thr Cys Asn Gly Gly Pro Ala Glu Ile Ile Val His Gly
                690                 695                 700
```

-continued

```
Lys Ser Gly Tyr His Ile Asp Pro Tyr His Gly Asp Gln Ala Ala Glu
705                 710                 715                 720

Leu Leu Val Asp Phe Phe Asn Lys Cys Lys Ile Asp Gln Ser His Trp
            725                 730                 735

Asp Glu Ile Ser Lys Gly Ala Met Gln Arg Ile Glu Glu Lys Tyr Thr
        740                 745                 750

Trp Lys Ile Tyr Ser Glu Arg Leu Leu Asn Leu Thr Ala Val Tyr Gly
    755                 760                 765

Phe Trp Lys His Val Thr Asn Leu Asp Arg Arg Glu Ser Arg Arg Tyr
770                 775                 780

Leu Glu Met Phe Tyr Ala Leu Lys Tyr Arg Pro Leu Ala Gln Ser Val
785                 790                 795                 800

Pro Pro Ala Val Glu
            805

<210> SEQ ID NO 78
<211> LENGTH: 264
<212> TYPE: PRT
<213> ORGANISM: Eucalyptus grandis

<400> SEQUENCE: 78

Met Gly Ser Thr Gly Ser Glu Thr Gln Met Thr Pro Thr Gln Val Ser
1               5                   10                  15

Asp Glu Glu Ala Asn Leu Phe Ala Met Gln Leu Ala Ser Ala Ser Val
            20                  25                  30

Leu Pro Met Val Leu Lys Ala Ala Ile Glu Leu Asp Leu Leu Glu Ile
        35                  40                  45

Met Ala Lys Ala Gly Pro Gly Ala Phe Leu Ser Pro Gly Glu Val Ala
    50                  55                  60

Ala Gln Leu Pro Thr Gln Asn Pro Glu Ala Pro Val Met Leu Asp Arg
65                  70                  75                  80

Ile Phe Arg Leu Leu Ala Ser Tyr Ser Val Leu Thr Cys Thr Leu Arg
                85                  90                  95

Asp Leu Pro Asp Gly Lys Val Glu Arg Leu Tyr Gly Leu Ala Pro Val
            100                 105                 110

Cys Lys Phe Leu Val Lys Asn Glu Asp Gly Val Ser Ile Ala Ala Leu
        115                 120                 125

Asn Leu Met Asn Gln Asp Lys Ile Leu Met Glu Ser Trp Tyr Tyr Leu
    130                 135                 140

Lys Asp Ala Val Leu Glu Gly Gly Ile Pro Phe Asn Lys Ala Tyr Gly
145                 150                 155                 160

Met Thr Ala Phe Glu Tyr His Gly Thr Asp Pro Arg Phe Asn Lys Ile
                165                 170                 175

Phe Asn Arg Gly Met Ser Asp His Ser Thr Ile Thr Met Lys Lys Ile
            180                 185                 190

Leu Glu Thr Tyr Lys Gly Phe Glu Gly Leu Glu Thr Val Val Asp Val
        195                 200                 205

Gly Gly Gly Thr Gly Ala Val Leu Ser Met Ile Val Ala Lys Tyr Pro
    210                 215                 220

Ser Met Lys Gly Ile Asn Phe Asp Arg Pro Asn Gly Leu Lys Thr Pro
225                 230                 235                 240

His Pro Phe Leu Val Ser Ser Thr Ser Glu Ala Thr Cys Ser Ser Ala
                245                 250                 255

Phe Gln Arg Glu Met Pro Phe Ser
```

-continued

```
                    260

<210> SEQ ID NO 79
<211> LENGTH: 136
<212> TYPE: PRT
<213> ORGANISM: Eucalyptus grandis

<400> SEQUENCE: 79

Met Gly Lys Glu Lys Ile His Ile Ser Ile Val Val Ile Gly His Val
1               5                   10                  15

Asp Ser Gly Lys Ser Thr Thr Thr Gly His Leu Ile Tyr Lys Leu Gly
            20                  25                  30

Gly Ile Asp Lys Arg Val Ile Glu Arg Phe Glu Lys Glu Ala Ala Glu
        35                  40                  45

Met Asn Lys Arg Ser Phe Lys Tyr Ala Trp Val Leu Asp Lys Leu Lys
    50                  55                  60

Ala Glu Arg Glu Arg Gly Ile Thr Ile Asp Ile Ala Leu Trp Lys Phe
65                  70                  75                  80

Glu Thr Thr Lys Tyr Tyr Cys Thr Val Ile Asp Ala Pro Gly His Arg
                85                  90                  95

Asp Phe Ile Lys Asn Met Ile Thr Gly Thr Ser Gln Ala Asp Cys Ala
            100                 105                 110

Val Leu Ile Ile Asp Ser Thr Thr Gly Gly Phe Glu Ala Gly Ile Ser
        115                 120                 125

Lys Asp Gly Gln Thr Arg Glu His
    130                 135

<210> SEQ ID NO 80
<211> LENGTH: 229
<212> TYPE: PRT
<213> ORGANISM: Eucalyptus grandis

<400> SEQUENCE: 80

Met Gln Ile Phe Val Lys Thr Leu Thr Gly Lys Thr Ile Thr Leu Glu
1               5                   10                  15

Val Glu Ser Ser Asp Thr Ile Asp Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ala Asp Tyr Asn Ile Gln Lys Glu
    50                  55                  60

Ser Thr Leu His Leu Val Leu Arg Leu Arg Gly Gly Met Gln Ile Phe
65                  70                  75                  80

Val Lys Thr Leu Thr Gly Lys Thr Ile Thr Leu Glu Val Glu Ser Ser
                85                  90                  95

Asp Thr Ile Asp Asn Val Lys Ala Lys Ile Gln Asp Lys Glu Gly Ile
            100                 105                 110

Pro Pro Asp Gln Gln Arg Leu Ile Phe Ala Gly Lys Gln Leu Glu Asp
        115                 120                 125

Gly Arg Thr Leu Ala Asp Tyr Asn Ile Gln Lys Glu Ser Thr Leu His
    130                 135                 140

Leu Val Leu Arg Leu Arg Gly Gly Met Gln Ile Phe Val Lys Thr Leu
145                 150                 155                 160

Thr Gly Lys Thr Ile Thr Leu Glu Val Glu Ser Ser Asp Thr Ile Asp
                165                 170                 175

Asn Val Lys Ala Lys Ile Gln Asp Lys Glu Gly Ile Pro Pro Asp Gln
```

```
              180                 185                 190
Gln Arg Leu Ile Phe Ala Gly Lys Gln Leu Glu Asp Gly Arg Thr Leu
              195                 200                 205

Ala Asp Tyr Asn Ile Gln Lys Glu Ser Thr Leu His Leu Val Leu Arg
    210                 215                 220

Leu Arg Gly Gly Phe
225

<210> SEQ ID NO 81
<211> LENGTH: 345
<212> TYPE: DNA
<213> ORGANISM: Eucalyptus grandis

<400> SEQUENCE: 81
taataaatga tgaatttatt ataaacgtat ccgtttgaga ttttgtggg tcataggtgt      60 atcaatttga atctttgat agtaacaaaa ataattttag gtagtttatg tttttcatga     120
tataaacctt gaaagttaat gctactaaat tgttatatat atattaggca aattacaacc    180
ttaatgcaac agttaatgac gtgatactgt tcagattata gatacaatgg ttatccttga    240
atgaataaga agaagtccta aggcaagtg ctatgagctt gcacgactgc ttttgcgcca     300
tttttgttta ccagcccggg ccgtcgacca cgcgtgccct atagt                    345

<210> SEQ ID NO 82
<211> LENGTH: 72
<212> TYPE: DNA
<213> ORGANISM: Eucalyptus grandis

<400> SEQUENCE: 82
cagtagggga cttgttcccc caagggcacg tgtcgttggt gaagctctgg cggtggatga     60
accgcgtggg cc                                                          72

<210> SEQ ID NO 83
<211> LENGTH: 544
<212> TYPE: DNA
<213> ORGANISM: Eucalyptus grandis

<400> SEQUENCE: 83
actagtgatt tcgtcgtctt cgtcttcttc gtcttctgga acttcgttgc tccgagcttt     60
atcagaaccg gcgatggaaa tgaaaccctc gttctctctc cctcgctcct ctctttcttc    120
tatccaggag cgtttgtaca ctgggagtac agagcttctt gcgataccga aactaccctt    180
ggacgactgg ccttttttgcc tcgcgccccc tctctgagcc ggggcgcaat ttgtcccttt    240
cccagagcga agtgtcgatt tgtccttcc acgaggcttt acctactccc atcgcccgag     300
ccccaagccc aggcccaaat gcctgttcct tgtggccctg ccaacattcc ctttgaaatt    360
aaaaaattaa aaaaaactc tctgccaggc aaaagtaaag attaacacca ccaaaattta     420
taacaaattt atcattcatt aattttcgtt aaatttatt ttcaaattac tgagtcgaat     480
tacatgtata aattcacgga tgtatcggtt cgagatttta tcctctaatt atcattagtg    540
tatg                                                                  544

<210> SEQ ID NO 84
<211> LENGTH: 515
<212> TYPE: DNA
<213> ORGANISM: Eucalyptus grandis

<400> SEQUENCE: 84
```

-continued

| | |
|---|---|
| gattactata gggcacgcgt ggtcgacggc ccgggctggt ctgccttcct ttaactcccc | 60 |
| ttttttgtaa cttttttaaaa tgtagtttta aatttaattt aattactttt tatattaatt | 120 |
| atttaccaca tcagagacaa aacaatgtct tttttgtatt ttctagtcac gtcaacatgc | 180 |
| aaaacaacgc cattttgcac tcaccttgcc ggaaaattgc cacgtcaaca atttggctag | 240 |
| agtggcgctt aagtgatcta ttttgctcca attttggcac ttaagtgtca ttttcctaaa | 300 |
| ttttagcact taaagtattc ctctatgtca agttttgaca cttggggtgt actttgtcca | 360 |
| atcataaacc gtataagttc actttaaaca aaaatggcgc aaaagcagtc gtgcaagctc | 420 |
| atagcacttg cccttaggac ttcttcttat tcattcaagg ataaccattg tatctataat | 480 |
| ctgaacagta tcacgtcatt aactgttgca ttaag | 515 |

<210> SEQ ID NO 85
<211> LENGTH: 515
<212> TYPE: DNA
<213> ORGANISM: Eucalyptus grandis

<400> SEQUENCE: 85

| | |
|---|---|
| actagtgatt tcgtcgtctt cgtcttcttc gtcttctgga acttcgttgc tccgagcttt | 60 |
| atcagaaccg gcgatggaaa tgaaaccctc gtttctctct cctcgctcct ctctttcttc | 120 |
| tatccaggag cgtttgtaca ctgggagtac agagcttctt gcgataccga aactaccctt | 180 |
| ggacgactgg cctttttgcc tcgtgccccc tctctgagcc ggggcgcaat ttgtcccttt | 240 |
| cccagagcga agtgtcgatt tgtccttcc acgaggcttt acctactccc atcgcccgag | 300 |
| ccccaagccc aggcccaaat gcctgttcct tgtggccctg ccaacattcc ctttgaaatt | 360 |
| aaaaaattaa aaaaaaactc tctgccaggc aaaagtaaag attaacacca ccaaaattta | 420 |
| taacaaattt atcattcatt aattttcgtt aaatttttatt ttcaaattac tgagtcgaat | 480 |
| tacatgtata aattcacgga tgtatcggtt cgaga | 515 |

<210> SEQ ID NO 86
<211> LENGTH: 782
<212> TYPE: DNA
<213> ORGANISM: Eucalyptus grandis

<400> SEQUENCE: 86

| | |
|---|---|
| gagggtttca tttccatcgc cggttctgat aaagctcgga gcaacgaagt tccagaagac | 60 |
| gaagaagacg aagacgacga cggcgacatg ccttgcttga acatctccac caacgtcagc | 120 |
| ctcgacggcc tcgacaccctc cgccattctc tccgagacca cctccggcgt cgccaagctc | 180 |
| atcggcaagc ccgaggccta tgtgatgatt gtgttgaagg ggtcagtccc catggctttt | 240 |
| ggtgggactg agcaacctgc tgcctatggc gagttggtgt caatcggcgg tttgaacccc | 300 |
| gatgtgaaca agaagctgag tgctgcaatt gcttcaatcc tcgaaaccaa gctgtccatc | 360 |
| cccaagtcgc ggttcttcct gaaatttat gataccaagg gttccttctt tggatggaat | 420 |
| ggatccacct tctgagctgt tggtcgcatt ctcctcagtg tttaccatgt atttcggccc | 480 |
| taaactctac ttctaggcct gttaaaagtg tcttttttaa ggtaattctg ctattacccc | 540 |
| tcttaagtgc atcttatcag taaacatgga atatcctgaa ctttgattat atgccggctc | 600 |
| gtggctgtgg aagcacttct ttatgttacc accagcttct caggtgaata taagctttgc | 660 |
| ccagtctgtt ctctggggga tttgcttggt gggtagtggc aatcagatgg ttttgtcact | 720 |
| tttgtgcata tttaagtagt aaatgtccac gacagcccaa agagtagcaa tccgggtgca | 780 |
| ct | 782 |

<210> SEQ ID NO 87
<211> LENGTH: 115
<212> TYPE: PRT
<213> ORGANISM: Eucalyptus grandis

<400> SEQUENCE: 87

```
Met Pro Cys Leu Asn Ile Ser Thr Asn Val Ser Leu Asp Gly Leu Asp
 1               5                  10                  15

Thr Ser Ala Ile Leu Ser Glu Thr Thr Ser Gly Val Ala Lys Leu Ile
            20                  25                  30

Gly Lys Pro Glu Ala Tyr Val Met Ile Val Leu Lys Gly Ser Val Pro
        35                  40                  45

Met Ala Phe Gly Gly Thr Glu Gln Pro Ala Ala Tyr Gly Glu Leu Val
    50                  55                  60

Ser Ile Gly Gly Leu Asn Pro Asp Val Asn Lys Lys Leu Ser Ala Ala
65                  70                  75                  80

Ile Ala Ser Ile Leu Glu Thr Lys Leu Ser Ile Pro Lys Ser Arg Phe
                85                  90                  95

Phe Leu Lys Phe Tyr Asp Thr Lys Gly Ser Phe Phe Gly Trp Asn Gly
            100                 105                 110

Ser Thr Phe
        115
```

<210> SEQ ID NO 88
<211> LENGTH: 1521
<212> TYPE: DNA
<213> ORGANISM: Pinus radiata

<400> SEQUENCE: 88

| | | | | |
|---|---|---|---|---|
| ccttcaaaga | caacagagaa | agttatgcaa | tatgctggca | gctagctctt | gggataatct | 60 |
| atttagcgat | gggtttgtcg | agaagttggg | agcatttatt | gtgaagcttc | acagaaaaaa | 120 |
| tgtcgaatac | atcaagcaca | tgaagaagca | atttgtgcca | taggctatct | ttagcctcat | 180 |
| ggatgttaaa | ataatttctt | tctttccttc | cttcttcttt | cttacccacc | aaaacacaaa | 240 |
| ataatagttt | caaattttga | attttcaccc | aatttatga | gaggacaaaa | ttacttagag | 300 |
| tctttcactc | tttaatttat | attctacata | agtacctaaa | gaggctctcc | gacaatcata | 360 |
| tgataccata | aaagtaacct | cgattagaga | gcgcctctcc | atacaatcat | ttgattttcg | 420 |
| agttaaatca | aaattatagg | ctatttccaa | atcaatctat | cgtccaactg | aaaatttcaa | 480 |
| atgaatggaa | ccagcacgga | gtttcgtagg | aaatagaagt | aataggtgaa | agaagcatt | 540 |
| gtcgaatttg | aaagaatacc | ctacgttttc | atttcaaaaa | ccatggtttt | ttgtaagagg | 600 |
| gattaagttg | actcaaggtt | gtagaaggtt | gacataacaa | tagcatgcag | gcacaggatg | 660 |
| catgtagtgc | ccgtaatttg | gaccaaccta | gtaagattgt | cacccgtttc | aaatgactgc | 720 |
| ctacaagtgc | atgcaaaggc | catggaagtt | gatggttagt | gaaaagatcc | ggagagacga | 780 |
| ttattccatc | atgcaatgca | catcgcacgc | ttgctttatt | actcacacga | ccaacgttcc | 840 |
| cttcatccac | ggaattaatt | tctctaatcg | atccaataaa | ccgccttcga | tgtcgatttc | 900 |
| caaatgaatt | aaatcgttac | atgcccaccc | gacttcacac | atgctccctg | cacgtgcaac | 960 |
| caaatccatt | acgcccaccg | ggcccggccc | tgctcacaca | tcttgcatcg | cccaactact | 1020 |
| ctgattttac | atgaatatca | atactattcc | ctccacttat | aaaatggcca | aacgccctgc | 1080 |
| ttagttctca | aagcagatca | gagcctttca | agagcttccg | caaagatttt | ctttgcgagt | 1140 |

```
aatttgatcg agaaggatgt ctgcatcgaa cggaactaat ggtgttgtcg cagtcaagtc    1200
tcgccgacag cacagacctg ggaaaacgac agccatggcg ttcgggaggg cgtttccaga    1260
tcagctggtg atgcaggagt tcctcgtcga tggatatttc cgcaacacga attgccagga    1320
ccccgtcctc cgccagaagc tcgaaaggct ttgcaagacg acgacggtga agacgcgata    1380
cgtggtgatg tcggatgaaa tattggcgca gcatcctgag ctggcagtgg aaggttcggc    1440
caccgtccga cagcgactcg agatctcgaa cgtggccgtg accgacatgg cggtggacgc    1500
gtgccgtgac tgcctcaaag a                                              1521

<210> SEQ ID NO 89
<211> LENGTH: 2590
<212> TYPE: DNA
<213> ORGANISM: Eucalyptus grandis

<400> SEQUENCE: 89
ctgaaactgt cgctcggcga tgcataccaa aggctgaagg tatcagaatc taatgcagct      60
tatgtaaaag cgcgatcaat ttattgaccc cgacgacctt gactccatac ttcacgcctc     120
agctttgtgt tggatggtct tgacctctct caccctaaaa ggtagctcaa aagaatgaga     180
ctttccgtca tacttataaa ccgaccacca gcctctttca caaccgacat gggacaacct     240
caaatagaat ttttaacaac acccttgcac gctctttcta tccactttat tatgccatca     300
catgagcgtt ttccacgcgt aaatcggcta ccacccactt tcacggggcg gcgaaacgag     360
aaaaaggtcc tacctttgac tcccccgcg tcccaaattc tcactcccga ccggtaaccg      420
agctcacaag tttcagcctt tcatcatcat cactcgaagg cagagagaag gacatacact     480
aaagacaacg aaacagtctc tccatcccgc catccgacac gatccacatt acggtacgga     540
acacatcccg cggagcaacc cgacgtccca aactcttcgc tgatcaaaac cagtccggtc     600
gactccgttt cgcgcggacg caacgtgaga gagggagaga gagagagaga gtaccggcga     660
ggggatgatg ctgtgcggaa gcgtcgtcgg gcgctctccc ggcgaacgcg tctctacatt     720
ccggcgacgc cgacgcgac gaaggcgggg aggggaatgc cgcggggttt ctgcaacgac      780
ggaagctcac ggcatttttc agagagagag agagagatgg cacgtcagag cgccattccc     840
ccacgcgacg ttccgccttc cggtattcct tccgggagaa aaagtgggca aattgcaata     900
gacaaaaaaa aaaagaaaaa aaagacggtc acccaaatta tttcttataa cacaaaaaat     960
cgtacctata taatatatct atcactaact tgtgcagtat gacaaattta cacatttacc    1020
tgaaactgtt tttataacat aaaaaattta acattttctc tgtgacaata atgttcaca    1080 caaatataaa actgggattt ttatttcaat tacaaattta gaataaatgc gcaacataaa    1140
tacaaattta tgattttttcg tgttggcaag aaagtttgag ataaatgtat cattgtaggt   1200
aaagtttaga gttttttttt atggctttta accaaaatgc acattttagt tccgagttct    1260
aaaagaaaaa ttactatttt cctttacatt tacttatgta ggtgtgtaat tataaatatt    1320
aattctcttt aggatttgta acaattcttt gagcttttgt tttgccttta ggccattaga    1380
attactaaaa agttaataat ataaacattt tttcgaccac ggtcaccatt catacctaac    1440
ttctaattat tgaaagattc tcgcatttga tcgaaatcca tttactctca taaatttgag    1500
gttttgaacg gtatctacca taagatcatg gtttattaca aaacacttat ggcgggtggc    1560
gcggacctgg cgagaatgtg gctactttaa tgatgaggat ttgagatatt ataccacgat    1620
ccataataat aaaggagcgc ggcaatcata tcttttttca tataaaggac gatttatttt    1680
ctatgctgtg agtatttgct cttggaatta taagatatta gagatcaaac ctatcaccaa    1740
```

```
cggtgatttg aaattaaaga agtccttgta tcacttacaa aaataaatat ataaaaaaag    1800 cttttcattgt gcacttgaat atttaaacat aaattattag tagtagataa ttttttaatt    1860
taactaataa tgagcactca tttttagaaa aatagttttc aaatcattca ttttctactt    1920
aaaaaaacca attgaccaac taaattagta tctctcattc agttggtgaa tgaatgactc    1980
gcactctaac ccttcacttg gcgagtcatt ctgtgtagac cagtctctgc aaatctagcc    2040
atgctcatct agcaactacc ttcaagcgca agtactttgt catgtagacc aaacgttgag    2100
caacacggaa tgaatcctaa cgcacttgga aaacaatcaa tccacgctac gcaagctaat    2160
gctcacacaa gcatcatgat acccgaagcc gaaaatacat gagtcgaaag acatcgaact    2220
ccgccgtcct cgcgaatcat ccgaatcgca tgtcacgccg ctcgacttgg tagcttaacg    2280
agccttccag tacctgctgt ttaaatgctt tgtcaatgtg attcgaatcc tttcaaagat    2340
cctgaaagtg cagcttcaaa aatggcgtcg accaaatggg cttgcgttgc tgcaatctcg    2400
ctcctactga gcctaggatc gagcgctgct cagaggtctc tccttatgag cagcgccaac    2460
tggcaagagg ccggtgagcc gacggatctg gacttacgtg gaggaattgc cggaaccctg    2520
gggtcatcaa gtgagggcgg caccatggcc agctccgaca tgggcggttt tggccaggac    2580
atgcctggtg                                                            2590

<210> SEQ ID NO 90
<211> LENGTH: 1172
<212> TYPE: DNA
<213> ORGANISM: Eucalyptus grandis

<400> SEQUENCE: 90
actctcacta attctttagt tttccaattt agccccttct gtaattgctc atcttcttta      60
ccaaattctc taatttggcc ggcgaagggc tgacaaggga ttggtcatgt caccctcacc     120
aaaggttgcc gaaggtccgg tgacctcagc tgacggccac ctacaccaaa tctagctcac     180
tagcagccta agcccttcat caactctagt gaaaggtttt gagtattttt taataaaaaa     240
tatttaaaaa atatatagcg agagctcatt acaaaaaaat tttaaaaaaa aatctaaaca     300
ttacttgaac tcaaagtgac tttataaaga gtttttacca aaggatcttg gtttcatcat     360
ttgcactaca cccaaaaccc aatttctaag ttaaatcaaa cccactgtct aatagagata     420
aggtaaatgt tataaaccaa attccaaaat tccgaagcac taaatatatt tgctgatctt     480
ataatcgcca attgagaggg tctcattctc caagggattg tgacatatta gtaattgata     540
gggtctcatc cgtaggactc cgactcagcc gcgccacgtg actggatcgc tgaacggcgc     600
ggaaccagag gagcgtgatt acctaatatt ttctcctacc ttggccttga gattgaattt     660
cagaaaaaga aaagaaaaa ggaacaactt cgccgactgt tctataaaat gcatgcgcca     720
ccccgacccc cacccacgca tcacatccat ccagcctcca cgacagacgc ataaacacaa     780
cacacgtcgg ttagagagag agagagagag agagagagag agagagagat gcttggacag     840
ttgtcgcacg agacggaaat gaaggtggga gcaggcaaag catgggagct gtatggcacg     900
ctcaagctgg tcctgctggc caagcaggaa ttctctaata ccatctgcga cgtcttggaa     960
ggtgatggcg gcgttggcac cgtcatcaag ctcaattttg gaagtttatc ctatacagag    1020
aagtacacaa aggtggacca cgagcgccgc gtgaaagaaa cggaggcgat cgaaggtggg    1080
ttcctggaca tgggtctcg ctgtatcgat tgcgattcga agtgataggc aaggacgagg    1140
aggagtcgtt ccgttattaa agccccccccc cc                                 1172
```

<210> SEQ ID NO 91
<211> LENGTH: 446
<212> TYPE: DNA
<213> ORGANISM: Eucalyptus grandis

<400> SEQUENCE: 91

```
gggtgaaaac aattaatgag atcatttgaa ttaaggaaag tggaaaggcg gttttctgat      60
tggtacactg aaacaacagg aaggtggtgg aggccgcaat gatggaattt atccacttta     120
atcattttat gaaatcgata cactaacctt tgtttctcct aaacccaaag gcattaatcc     180
ctgtcctcct cactcgatct cgaaggccag aaggggagg ccgagcctct tgctttttt      240
cgtgtataaa agggcctccc ccattcctca ttttcacca tcctccgttc gttcgttccc     300
ttccctttcc attgttgcgt ttaagccctc caattttctt ttggcgtccc gttttggggg    360
ctcccttgaa gatctcctct tcatttcggg atttcctgcc ttcgccgcgc catttgaagt    420
tcttttctg agagaagaat ttagac                                          446
```

<210> SEQ ID NO 92
<211> LENGTH: 2119
<212> TYPE: DNA
<213> ORGANISM: Pinus radiata

<400> SEQUENCE: 92

```
atcttattcc cacctcacat caataaattt tatacgattt taacatcttt aaaattaaaa      60
gaatcaagaa ggcatccagg tgataaagcc acgtccaata taaatctcc tcggtggatc     120
ctttcaatcc agctacccaa tgcggcgaaa ataacgctga ttggactggg ctacactgta    180
atcacaaatt cccttccgtt tagatttcaa ctcgttgacc tacgagtatt ttatcgattt    240
aaaattatac aaaaaattgt ggaatgtttt acataagcaa aacttaaata atgtaaatag    300
cgatgatgct ttacttgtac ctaaaaattt cttccaaatt aaaccaaata tcaaatccta    360
gattgatgag ttccagtgga gtctgccatt ttatttcttt ctctctttca ttctttgcaa    420
cgaaaggaga aaatccttaa cacaattcga aaacgataat gattctggca aaagagaaaa    480
aaaacgtgaa gattagacac ttgttttgtt ttaaatgagc aatcacatgt gaatagagag    540
ggttttatgg gcctggtttt gtgtgcataa tttcttatga aagcgatgtg cctggagcgt    600
tgaagctcat agaacattgc aacaagagat cgagagtgtg ggttagaaaa ccgcaacaat    660
agtttgtgtc gtgttttct atattcagag gtgttgtgtg gtaaatatct ctggatttat    720
ctcgaatgcg tcacttttac agacacagaa gctcagcgga aaccctcaac gctttaaggg    780
ccataaattt gctcagtttt aaaaattgtt tgatttccca ggtttgaata ttttcttttt    840
gttatcggaa gtggctctgc cttatgagta tcatgttctt ggttttgtgt tgggcgctta    900
ttgattcagg tatgtattat ttctagtcct ttttatcagc ataggtggaa tgttctgtat    960
tttatatttt ggggccatac acatggaacc gttgtcatta ccatgcttta tagataatgt   1020
ctctctgaat ttgttttat aggctttgc ctcctacgca gatttttaaa ggaaaataca    1080
aagatattta gccaattttt gttgttgtga ccttgaattt ctaaaaaatt taatggattc   1140
gttttctaaa ttcctgattc gtcaaaggct gaagggcgcg atagtaatag aaaatggacg   1200
agagtttatc ttttcatggc tggacacaca gaatttgtgg aggggattct ccattctggt   1260
ttatccaccg ttagttctct ctgtactcca cccttagttc tctttgtact cgagaccttt   1320
aatgattaac cctgcttatg ctgtcagtac tgaactcact tccagagccc caaaaatctc   1380
tcccaagttt gccttatttc ttaaaataat tcacaagtag aaaatgagat ttttgcaatt   1440
```

```
ttgtaactaa catttcccgg tctcctctgt atgttttcac cccttaatgt aattgaaatt    1500
tgcacccggg ttagattcaa agcggagaat aacatcgggg ccttgttcta gacagagatt    1560
tttcacaaat aacaggttcg aaggtatgtg tagacatctg ggtagttgta gaataaagac    1620
ggagcccatt aggtggatcc aatcgaagaa ctcagatggg aaaacagata aaattatcg     1680 ggtggacctt cctccacatg ttaattatat atcaagtgtc gccaatcctt atgtgaaaca    1740
tttagtaaag cttcgccaga gcacttctta taggcattct gtgggctctg ttgttgtggt    1800
tggaagtact cctttaaggg aggtatctga atatttgcaa cagaagtcag taaacaagt     1860 ggttgactgt ctgtttgtac aagatgttac tggcatacct gtgggcttga tagagacttc    1920
caggcgcatt gtgcatgtaa atcatttggt gatgcagaag ctagccggag tagagtctat    1980
agagcccact gaagcaattg gtgtaatcaa gcttcctagc agcttctaca acttggaatc    2040
tcttgaaatc actctagttc ccagatatgg tgctcgtcgc cacatcgtct gcttgtactt    2100
gatggcattc aggatcctg                                                 2119

<210> SEQ ID NO 93
<211> LENGTH: 2571
<212> TYPE: DNA
<213> ORGANISM: Eucalyptus grandis

<400> SEQUENCE: 93
aaggtaactg gttcagcaga gcgcagatac caaatacttg ttcttctagt gtagccgtag      60
ttaggccacc acttcaagaa ctctgtagca ccgcctacat acctcgctct gctaatcctg     120
ttaccagtgg ctgctgccag tggcgataag tcgtgtctta ccgggttgga ctcaagacga     180
tagttaccgg ataaggcgca gcggtcgggc tgaacggggg gttcgtgcac acagcccagc     240
ttggagcgaa cgacctacac cgaactgaga tacctacagc gtgagctatg agaaagcgcc     300
acgcttcccg aagggagaaa ggcggacagg tatccggtaa gcggcagggt cggaacagga     360
gagcgcacga gggagcttcc aggggggaaac gcctggtatc tttatagtcc tgtcgggttt     420
cgccacctct gacttgagcg tcgattttg tgatgctcgt caggggggcg gagcctatgg       480
aaaaacgcca gcaacgcggc ctttttacgg ttcctggcct tttgctggcc ttttgctcac     540
atgttctttc ctgcgttatc ccctgattct gtggataacc gtattaccgc ctttgagtga     600
gctgataccg ctcgccgcag ccgaacgacc gagcgcagcg agtcagtgag cgaggaagcg     660
gaagagcgcc caatacgcaa accgcctctc cccgcgcgtt ggccgattca ttaatgcagc     720
tggcacgaca ggtttcccga ctggaaagcg ggcagtgagc gcaacgcaat taatgtgagt     780
tagctcactc attaggcacc ccaggcttta cactttatgc ttccggctcg tatgttgtgt     840
ggaattgtga gcggataaca atttcacaca ggaaacagct atgaccatga ttacgccaag     900
ctatttaggt gacactatag aatactcaag ctatgcatcc aacgcgttgg gagctctccc     960
atatggtcga cctgcaggcg gccgcgaatt cactagtgat tggcccgggc tggtctggag    1020
tggccaccat cggcataatg actaggaacc cggaacatca actgatggaa gaaaagccga    1080
cattcctcat caagagctcc tctcactcct tccccactac tactataggg cacgcgtggt    1140
cgacggcccg ggctggtctg ctgtcatatt tgtatatgag gtcctatgta tgcttgctat    1200
gtgacctcct tcatgtatgc tgtgaagaga gtgtagcagt aacatggcca tctgcgaaat    1260
atggattcac cttaaaatct gatgattttc agaaaacgag gaaggtgctt gccgagaaga    1320
ttgcacagct caattcagct atagatgatg tatcctctga gctccgaact gaagaatcat    1380
```

-continued

```
cagatgagat tgctgttgcc cctgatgaaa ttgaagctgc tgtttgatgg cccaaacctc      1440
ccaggcctac gatcatggtc atcttctgtt ttggtgcaat tggctctacc tttttggtgg      1500
cctccatata acagaataat ggttcatatt gtaaaatctt ctgtttattt ctaaagacca      1560
atgcactcag tttcttttga tatgattgtc tcgattgagg aagtgcatca ttcgtggtat      1620
gattatgcag ataccatttt aactcagcag actttgtacc gtatcatcgc agcttttccc      1680
ttcttgtgta tgcataaatc tagtccttca ttgaaggtga tcgccgttac agtctggata      1740
gtgtgtgcca tcagatggca ctacgattag tgtggttgac atggtgtcaa cttgaaagcc      1800
aattggtgac gatggtactt aatgtaagat tggcagatgg tgagaacgag attttgctcc      1860
agaatggcaa agcaaggcta agttgtagcg aatcaaatga tctacgaacc atcctagctg      1920
gctgtgtgac cacacactga agttctattg aactaagcca gttatggatg atatgggagg      1980
agaaaattga gaaatccatc agatggagtg ttggccgtgt tgggcttttg tcgcaggccg      2040
atacttcgaa ttcaggcgta ttttattcc tgactgccgc ctctcccgga aagggaaggc       2100
ggatattatt ctctgaacga tttccaccat caactccaca tcgatctcca agccagaaat      2160
atacacaccc caattttctt ttaaatatat gggacatata tggtgtaggc tctcgcgcat      2220
gttaacacat aagctctctc aacaaaaatc tggctcgtgc ttttaaccga gaagttcacg      2280
agtcattgaa ggagtggcct ttaggggagg gagagagatg gattggtggt taaaatcagt      2340
ctgtggctca catttatacc gtggagatcc cccaacagca accttatccc attatatatc      2400
cccacaacac catattcacc actcgttcct tctaattggc ttccaaccat aattcacaga      2460
cacacatgta gtgaccaatg agaaaggaag aaaaatacag gctttcgaaa gctagtgcgg      2520
tataaataac ctgggaaaag caagccgctt gagctttagt ttcagtcagc c               2571
```

<210> SEQ ID NO 94
<211> LENGTH: 1406
<212> TYPE: DNA
<213> ORGANISM: Pinus radiata

<400> SEQUENCE: 94

```
aaagaggcgg aggaattgtc tagatggtca aaagtgaccg gaatctaagc aaaaaatttc       60
aaaaaatgtt gtaaaggtag cgtttgaatt gtgttttga tggtggaaat ggattcaacg       120
ccatcaaaaa cgtctaagac acctaaaatt ttgaatttta acaactatat cttggattta      180
caaaaatcct tgccggattt tctctaaact ccttcacctt acgcaaaaga tatatatttt      240
tttgtgtgat gttgtgcatt ataagtttga tagtgaagta atgatatata tcctttatgt      300
gatggatgat tgaataatga atatattaaa tgaaataaat aatgatggga taatgaatat      360
attatatgaa ataaatataa agtaaaatgc tattttttaa tggtgttaat gatgaattag      420
tatcatcctt aaataatttg ttagtgaatt attaaaatga tgagttagca tggtcgttaa      480
ataaattgtt agtgaattat tatatttata tatttcctta ttagaaagtt ttttttttgt      540
aaaagttttc cttgaacttc acccatattt aattatcaat aatttatatt taataaatga      600
tatatataac ttctagcaga atgacacgcg acttgtatat cttttcattt tttaacccat      660
gaaaaccgat tagggtattg caaattaggg cattgccatt caaataattc tcagatgaaa      720
gattctctct aacaattaca aatgattatt tttttccatg agtgttgcat gttcgaacgg      780
tctgcccagt ctgtgagaga gcatagagaa ccctcccctgc ccaatttgtt agagcataga      840
gaaccctact gcatgagtag taagaaaaat attcggtctc aattcggcaa agaccacctc      900
gaatggatga cttcaacgac aatctcatga tagtgttctg atcagcacca gttcacctat      960
```

| | |
|---|---|
| atattttatc tagggtttag tttgcatgta tcaatcctct ggtgcactag gtaattcttt | 1020 |
| cctagtatca tatatcctta atactgtttt gtcttttaat ccatggctac catcagaaca | 1080 |
| agctcaaagc agaaatcggg agcatcagcc atcctcttgc ttatcgcgct tgcagggtta | 1140 |
| gtaaatgcgt gcaacgctgt gggtattgag ccaatgtgcg acactgtggt gtcgagtctt | 1200 |
| ctgaggcttc tgccatgcag gacggctgtt gatccctcaa ttgccgccat tccacttcca | 1260 |
| agctgctgca acgcggttga gtcagctggg cttcaatgcc tctgtctcgt cgttaacggc | 1320 |
| cctccttttc caggggtcga ccgcggcctc gcaatgcagc tgcctgccaa atgccatctc | 1380 |
| acccttcctc cctgtaacag ttagtt | 1406 |

<210> SEQ ID NO 95
<211> LENGTH: 2546
<212> TYPE: DNA
<213> ORGANISM: Pinus radiata

<400> SEQUENCE: 95

| | |
|---|---|
| ctggtagaac aagcagctca aggagcacca aggcacgagc ccactttgca tgttgtagac | 60 |
| taacgaattt tacattagaa taaaatatgt cgacaatatc gaggagatct tctccaaaat | 120 |
| ccaactcatt aatctctatt atgcacaaac gagtgatgtg tcgagactca tctgccaaca | 180 |
| agccatcaac atcaagaagg gaacggaata gagccaaagg gaaccctaga daccctcatc | 240 |
| cacataataa tgaaatattc cacgtgtgtt tttcaaaatt tgaaaatttc atgtattttt | 300 |
| tggttgattg gttgtggtct ggttttttcc aaattcaatc tagttcaagt ttttggagtc | 360 |
| gaccagttgg gtaaccagtc taattctggt aacattgcat tgtacttgat ctcaataaaa | 420 |
| gcatatagga tagaattatc ttctgtcttg atggtttcca tgagaaccaa ctgctatact | 480 |
| atgaaaaata tcaatgttcc acaatatttt tgggacaagg gaacacaaga ttgagtcaac | 540 |
| agttcaggac cccagaaaaa ttattcctga gttcgcagat tattttccta aaagtgaaca | 600 |
| attcaagacc ctagccaaat cattcccaag tccaagttat gtgacactgc gactaacaag | 660 |
| gcaagttgga agaaaccatc aatcaatctc ctagttaatg acagtccttg taagaagttc | 720 |
| aagaagatta acaccagaag aggtcatgct gactgctttt atccaattct ctctgctctt | 780 |
| caccaacaga aatagccaag atggttgtac ccattcccta atctaattta ttatatgaat | 840 |
| ttctctttat ttttctacat ataaaaaaca aaaacttttc ttgatggtca acagaaaaag | 900 |
| gcagttcgat tggatttaaa catccaaata cctcccacag attgagaagg ccaagcccca | 960 |
| atccaacagt ccatgatata atatttattc aatcacactc aagataatgc aatgaaggtg | 1020 |
| caccacgcta ttagattctg cacagaactc agatgactgt aattatcaac tttaaccagg | 1080 |
| agtaatttaa aaactcaatt gtgcttcagc tatgtggaaa actttggca ctggaaatgg | 1140 |
| tataaatgtt gttgaataag caaacatttt tcaagcactg aattcaaagt caagtcaaag | 1200 |
| gaacatctta cttgggctgt acaggaaatc tgaagtacaa aattagcgaa aaacaggag | 1260 |
| aaagagagta gtcattacat gttataacat taccatatag gattttgtaa tacttcttga | 1320 |
| tatttcaact tcccgactga tgaaatgtat gccactacag aacaggtcag tcatgtatgt | 1380 |
| gagcaattag ccaaactagg tcctaaggtt caaccagtgc agacaacgct gtaactgaaa | 1440 |
| caaatttgtg ggacaattaa aaattctcta ccaggatagt tgtaccagta ggtgcccttt | 1500 |
| tcaaaccatg atttaaaaca caagggtggc ttaccacttg accaaatcat ttaataacca | 1560 |
| accccctcgaa catatcaaga aagaaaacat ctgcatataa gtaaattgaa agatgatatt | 1620 |

-continued

| | |
|---|---|
| taagaggcac tgccttaaat tttccatttg gacaaatcca cattgcttga taagcataaa | 1680 |
| accttggtta agagcaagtt tagggaacca tcaaatattt ctacatactt tacaatagtg | 1740 |
| tgtttataaa gctaatcaaa tgcttctatt taaatatata gcaacctaca caagaaattc | 1800 |
| actaggacag caatcacttg gccaatgtga ttaccaatat aaccatactt gaagagcata | 1860 |
| cataaatcac aaataatgat tcaattagaa atatcttaaa gataaactat tattcaatgt | 1920 |
| acatgttaca aagaacctca cctgtccgcc tttgaggagc aagtagacaa ctaaaagcgg | 1980 |
| aggttacatc ctgaactgaa cttgttctcc tctgttccaa gaacttgcat tgtattttga | 2040 |
| gtaacttcac tcgtgccgaa ttcggcacga gaaaacactt tgattgcttc cgcgggtggg | 2100 |
| ttttactttc tctggaatag ttagttccgc cgttttttgga agatttatca gaatggccaa | 2160 |
| aattcaggtg tcaaacggga gcgtcgtggt ggtggcggcg atgatattta tggtggcggt | 2220 |
| ggccatgcaa aaccatcacg tcgccgccca aagtgctgac tgcgcaccac cgcggagttg | 2280 |
| ctgagcccct gcgcctcggc ggtgggaaac aacccgcaga ccccactccc gaatgctgtg | 2340 |
| ctgttctcca gaccgccgat gtcgactgca tctgcgccct cgtcgaatca accataaaat | 2400 |
| tgccttccga atgtggtctt gacaccccc agtgcccaag cgactagatt ctcaagaccg | 2460 |
| tgactgagtg ttggtttcag agccagtaaa cattcattct gctaataaat gagtgtatgg | 2520 |
| agctttaata ttggaaaatg cttcat | 2546 |

<210> SEQ ID NO 96
<211> LENGTH: 4726
<212> TYPE: DNA
<213> ORGANISM: Pinus radiata

<400> SEQUENCE: 96

| | |
|---|---|
| gattactata gggcacgcgt ggtcgacggc cctggctggt cctaggacac cgtaatatat | 60 |
| aacctcgaca tggcttacaa agctttgact tgcattctca ttgggcttac aatggtgctg | 120 |
| ccaaaaatga aaagtacat atgtaccct gttgaaatga gcagtaatag gcttgaacaa | 180 |
| tagtgaattg ctacaaaatt atgaatgcct ttctttgctt gaatgtgggc taaggagaag | 240 |
| tgggatttac atttgacttg caaatcctaa gacttgtcta gagctaagcc tccagaggag | 300 |
| gaaccatctt acatagtctt gagtctagag cggagaagat agccaaattt gaaggaaac | 360 |
| ttttatttat ggggagaagg caaacaactt gagggggaag gatgatcaat aagtagggta | 420 |
| agggaatcca caacagaggg cactaaggaa atggggtgt tagaattggc aactagggcc | 480 |
| aaattccacc ttgggatagc tctctggatg gagatgatga ttgcattaga ttcctctttt | 540 |
| cgagaggacc aagattgata taaagatcat ctcatttgga caagcatagg tatgattttg | 600 |
| aatttatacc cactcatgca caattttttt aggtccgcca catcatcatg taggctcatg | 660 |
| aagcccaacg gacatgactc ttcgccctta tcgtcttgta taaatacaag tgtcctccca | 720 |
| cctcatttgg catcttcatc tcttacagat tctctcttct tccctcattg gttcttgcat | 780 |
| cattgggcat tctctctctc ccacgtgtgg cacaaggagg atgaaattac aagaccgaaa | 840 |
| ataatagaaa ttttgcaatt tgaccagcat tgaccatgac cttccaagca tcattcgact | 900 |
| tcaattttt tgggttattt ttgtctcaac aagccgcata ttttggcaaa aaatcgagg | 960 |
| cattctgggc acttcgacta caaaccaaaa ttgtaggttg actgcaaatt tcaaatagtt | 1020 |
| tgactattga cattgtcact gttttcgatt gactttgacc tcctaattag gccgagtttg | 1080 |
| actaggggag gctgatttgt tttaaggaca tttgattgat gctttgacta gcattgactt | 1140 |
| ttatagttaa ggttgaagtt tgactacagt tgactgcata aatttgcaga gatgttttga | 1200 |

```
ctttgaattg ggcaagtcaa tttgaatttt gtactatctc tctattttga acatttgata   1260
taataataag aagattcgat caaagggttt tccccgcatt gggttttttc cctggcatcc   1320
gccaaatctg gtgttctctt gtctttgctt gtcttatgca ttttgtttca ttttctatct   1380
acttttactg tcaatgtgat tattgtcagt gttattggaa attggaaatt gtgattgggc   1440
tgctaaggaa cattgaagta aattgtgcta acaaagaac ataccattgt taacgaaaat    1500
taacaagggg gaaacacaga ggaatggttg caattgcaag attgtcattg attttgactt   1560
caagtgagga aggtcgcgtg gaggtcgcaa ggggagaggga ataggagaga aggccctatc   1620
aacttgttca aggagagggg caatacaagg aatggaggaa ccctcaccaa tgaataatcc   1680
atgcacaaaa gtaatagaat gaacaaactt accacacgga gagcttcct tgttgccaaa    1740 agccttgcct ccgagacctg aatcctccaa tgcatcaaaa ttattgatca ttgaatcaac   1800
cacgattagg gccacttcct tggctaataa agcaattagt gtagcaaatt ctaaagctaa   1860
cttcaaagaa accttagctt ccaaaaaac aattgaaggg aggcaatgaa gatggcttat    1920
cacactaagc ctaaacatgc cccaccctat ggcatctaaa acatctaaaa gggattcact   1980
agtaatcgat cttttgtact tatgaaaaat tcccatgaac caattcgatc tcttccaaaa   2040
agccatctat gaggtcaacc tcaacctggc tctaatgttg attgagcttg taatcctagc   2100
cctactccaa tcttaagaac caaccaattt tatttccaat tgattcaagg cccctacac    2160 tccaaaagaa gcaagggaag gccaaggaga atggcccaaa cttgagcaga gaataaggat   2220
tctctgtgag ggtcgaaact aacatcccat tcacgtaaaa tcaaaccaga gagacctcaa   2280
ctccaactct tcttaatgat gaagcacaaa tattattttg agtgaaattt gaaaccaaga   2340
aaacctctca ctaatatatg gaagagggc aatattcaac cattggtacc caaatcgcct    2400
caagacactt accaagggag ccaaccaaac aatcttacca caaaaccaac caacagtgtt   2460
tttacccaca agctcttgga tggaatccag gataatgtct tcaccaacaa ccatcttatg   2520
tctatccttg caagcacaaa tgcattgagc tttagatttg gagtgcataa atacaggggg   2580
gtatccaggg gggggagggg gtttgctaga accccagact caccaaggca tgaagacaaa   2640
atgaggagag agggatctag attgggggat gcaagttgat gaagcatgaa aaggcaatcc   2700
atcaccctgc atggcatatt tacgaaggtt gttcagagga atgagaacta atggatgaac   2760
aacagctggt agaacaagca gctcaaggag cgccaaggca cgagcccact ttgcatgttg   2820
tagactaacg aattttacat tagaataaaa tatgtcgaca atatcgagga gatcttctcc   2880
aaaatccaac tcattaatct ctattatgca caaacgagtg atgtgtcgag actcatctgc   2940
caacaagcca tcaacatcaa gaagggaacg gaatagagcc aaagggaacc ctagagaccc   3000
tcatccacat aataatgaaa tattccacgt gtgtttttca aaatttggaa atttcatgta   3060
ttttttggtt gattgttgtg gtctggtttt ttccaaattc aatctagttc aagttttgg    3120 agtcgaccag ttgggtaacc agtctaattc tggtaacatt gcattgtact tgatctcaat   3180
aaaagcatat aggatagaat tatcttctgt cttgatggtt gccatgagaa ccaactgcta   3240
tactatgaaa aatatcaatg ttccacaata ttttgggac aagggaacac aagattgagt    3300
caacagttca ggaccccaga aaattattc ctgagtttgc agattatttt cctaaaagtg    3360
aacaattcaa gaccctagcc aaatcattcc caagtccaag ttatgtgaca ctgcgactaa   3420
caaggcaagt tggaagaaac catcaatcaa tctcctagtt aatgacagtc cttgtaagaa   3480
gttcaagaag attaacacca gaagaggtca tgctgactgc ttttatccaa ttctctctgc   3540
```

-continued

| | |
|---|---|
| tcttcaccaa cagaaatagc caagatggtt gtacccattc cctaatctaa tttattatat | 3600 |
| gaatttctct ttattttct acatataaaa aacaaaaact tttcttgatg gtgaaacaga | 3660 |
| aaaggcagtt cgattggatt taaacatcca aatacctccc acagattgag aaggccaagc | 3720 |
| cccaatccaa cagtccatga tataatattt attcaatcac actcaagata atgcaatgaa | 3780 |
| ggtgcaccac gctattagat tctgcacaga actcagatga ctgtaattat caactttaac | 3840 |
| caggagtaat ttaaaaactc aattgtgctt cagctatgtg gaaaaacttt ggcactggaa | 3900 |
| atggtataaa tgttgttgaa taagcaaaca ttttagaaca tttttcaagc actgaattca | 3960 |
| aagtcaagtc aaaggaacat cttacttggg ctgtacagga aatctgaagt acaaaattag | 4020 |
| tgaaaaaaca ggagaaagag agtagtcatt acatgttata acattaccat ataggatttt | 4080 |
| gtaatacttc ttgatatttc aacttcccga ctgatgaaat gtataccact acagaacagg | 4140 |
| tcagtcatgt atgtgagcaa ttagccaaac taggtcctaa ggttcaacca gtgcagacaa | 4200 |
| cgctgtaact gaaacaaatt tgtgggacaa ttaaaaattc tctaccagga tagttgtgcc | 4260 |
| agtaggtgcc cttttcaaac catgatttaa aacacaaggg tggcttacca cttgaccaaa | 4320 |
| tcatttaata accaacccct cgaacatatc aagaaagaaa acatctgcat ataagtaaat | 4380 |
| tgaaagatga tatttaagag gcactgcctt aaatttttcca tttggcaaat ccacattgct | 4440 |
| tgataagcat aaaaccttgg ttaagagcaa gtttagggaa ccatcaaata tttctacata | 4500 |
| ctttacaata gtgtgtttat aaagctaatc aaatgcttct atttaaatat atagcaacct | 4560 |
| acacaagaaa ttcactagga cagcaatcac ttggccaatg tgattaccaa tataaccata | 4620 |
| cttgaagagc atacataaat cacaaataat gattcaatta gaaatatctt aaagataaac | 4680 |
| tattattcaa tgtacatgtt acaaagaacc tcacctgtcc gcctt | 4726 |

<210> SEQ ID NO 97
<211> LENGTH: 635
<212> TYPE: DNA
<213> ORGANISM: Pinus radiata

<400> SEQUENCE: 97

| | |
|---|---|
| aaattctatg aaaaaaatcc aatcatatta aaagtccaat tgattagcaa ttttatgaga | 60 |
| aaaatccaat tatgttaaaa gtcactgagt gtggccgaaa ttgtgaccga aattgaatgc | 120 |
| aataaccgag ggttttttcaa accaaggtta agcctctcat cattggggtg tgtatgaaaa | 180 |
| tgtaatgggc atcgataacc ttttattaca acttcacgaa aattgcctct attcaatggg | 240 |
| tgtggatgaa aatgtaagtg cgcatcgata atggaaagcg atatgcagca aaatcaataa | 300 |
| acctgacttc ccatgtgagt gatgatttga tcgtacaact gatggtgtga agttactttc | 360 |
| agcttcacct tcgggcataa tcagggaagt agggccaagt ttgcttagta tcactctaat | 420 |
| ccccaacacc gtgattacta tcttcatcaa caatggccac cttcgtcatt actttaactg | 480 |
| gtgggataca gctactttac aactgtaaat ttgttgaggc agcctatcct cagcctatac | 540 |
| atactaatta ttgcagctcg attaggtatc tgctgtgaga atagctgtgt atctctgcgc | 600 |
| tggttgcagg atccaagttc ctctcagagc cctcc | 635 |

<210> SEQ ID NO 98
<211> LENGTH: 468
<212> TYPE: DNA
<213> ORGANISM: Pinus radiata

<400> SEQUENCE: 98

| | |
|---|---|
| ctggtaaatt gagattccaa attattgatg cgaagcttcc tcgtggctgg tcggtgctgc | 60 |

```
tggcatccaa accctaaatg aaaagaaaa aggtgtccgg acggattttt ttagtatttt      120
tttcttattt tttttatgaa ccgtcggatt cgagatcgga cggcgatccg aaactgcaag      180
cgtcggccgt cggatgcagc atcggacggc aaagaaggaa ccctaaaacg cattgcaacg      240
tgcttggtgg gtggagggtc tatgccagt atatgttgat aacaaggag aggaagtagt       300 cctcttcatc tagtgcgagt ctctctgctt ttctacgccg ctgcgaagct gttctgtggt      360
gtttctgatt ctccagactc aggcagtcgt ttttgtaaga gaatttagtt catcatggga      420
aaggagaaaa cccatatcaa cattgtggtt attggccatg tcgactcc                  468
```

<210> SEQ ID NO 99
<211> LENGTH: 222
<212> TYPE: DNA
<213> ORGANISM: Pinus radiata

<400> SEQUENCE: 99

```
atccaaaccc taaatgaaaa agaaaaaggt gtccggacgg attttttag tattttttt        60 tcttattttt tttttatgaa ccgtcggatt cgagatcgga cggcgatccg aaactgcaag      120
cgtcggccgt cggatgcagc atcggacggc aaagaaggaa ccctaaaacg cattgcaacg      180
tgcttggtgg gtggagggtc tatgccaga tatgttgtaa tc                         222
```

<210> SEQ ID NO 100
<211> LENGTH: 597
<212> TYPE: DNA
<213> ORGANISM: Pinus radiata

<400> SEQUENCE: 100

```
aaatgaggca gctaactatt tatttggttt tggcttcact gacttgttcc ttagtgtatt      60
aatgaacaat ctctttagac tcagagatgg tgagaaagat tctatgagaa atattcttgt      120
tattgcttcg actcatatcc cccaaagagt ggatccagct ctaatagctc caaatcgatt      180
agatagatcg atcaatattc gaatgcttgt tatcccacaa cgacaaaggg aatttcctat      240 tctttatgt agcaaaggat tatactcggg aaaatgtccc gatgaatttg gatctataac      300
catagattat gatgcacgag ctctattagc tcaggcctct ctgctgctcc ttggattgca      360
atctcattct ctgatttgcc gtgctgtttg ctctgctcac ttcagcccag atggagacct      420
tcttgttcac atcggagtct gtaaatgagg acacccaga caaactctgt gaccagattt       480
ctgatgcagt gttggatgca tgcctcaccc aggacccga cagcaaggta gcatgcgaga      540
cttgcactaa aacgaacatg gtcatggttt ttggtgaaat caccaccaag gccgatg        597
```

<210> SEQ ID NO 101
<211> LENGTH: 669
<212> TYPE: DNA
<213> ORGANISM: Pinus radiata

<400> SEQUENCE: 101

```
cctggaaatg ctatattaac tcaacaaagg attttcagcc aatcacaatt tgacaggttt      60
gaaatgaaag attacaggca tttccaatgg aacagaatat aattacttta ttccctcaaa      120
gtatcgtata aaataaatct tttgctccac acactttgga aaatacattt tcaacaatgc      180
accgacaaac tttttctacc acgttatgga accatacaag ttaaatttaa acacgaatta      240
cgcgtatatt tctaataaat cgatggttga gattgaatgc cgtgggcgat ctcacgcgt       300 ccgattggga tcactagtcc atcactcatg gtctgcattg cctttaaatt ggcggggcga      360
```

```
ggaaagacca atgcgtcatt ggtgtagacg agctctatta gctcaggcct ctctgctgct      420
ccttggattg caatctcatt ctctgatttg ccgtgctgtt tgctctgctc acttcagccc      480
agatggagac cttcttgttc acatcggagt ctgtaaatga gggacaccca gacaaactct      540
gtgaccagat ttctgatgca gtgttggatg catgcctcac ccaggacccc gacagcaagg      600
tagcatgcga gacttgcact aaaacgaaca tggtcatggt ttttggtgaa atcaccacca      660
aggccgatg                                                             669
```

<210> SEQ ID NO 102
<211> LENGTH: 230
<212> TYPE: DNA
<213> ORGANISM: Pinus radiata

<400> SEQUENCE: 102

```
atccacctcg gaatgaaatc actatgcaca ctccaccttt tttttggctt cttttctcgt       60
tgcctttacc atcagaatca agcacgaaga gtaaatatca cccatgcttt acaagtgggt      120
tggtagcatt agcgattccc ttcaccaaat gaaccctttg ctggtgatga gtggacaacc      180
taaagttgtt tgctggtgat gagtggacaa ccagagtggg ggttggggaa                 230
```

<210> SEQ ID NO 103
<211> LENGTH: 596
<212> TYPE: DNA
<213> ORGANISM: Eucalyptus grandis

<400> SEQUENCE: 103

```
actttgaaag ggtctcgagt caaagtgctc aaattgagag ggagaatttt agaacaaaat       60
cagatttgga gaatacatgc cattttaggg ggattttggg gatttcgcat atggcgtcgc      120
gtcgtcggcg ccttcttctt tacagattgt atcctcccat taaccgcgtg gacctgcact      180 gtaacccega aacggtgggg gccaatttcg tctttccgcc tcctccactc agcttcgtgg      240
aagattaaaa tcctcaccgt ccgtgcaaac gccacgtggc gcgttagttt gcgcgtggaa      300
aggtcctcac gaaccgtaaa gggcaaaaaa aagggaaaat aaaaaaggag gaggaggagg      360
gaggaggaag aattgtccga ttgaaaataa gagtgcggtg gtgtggtgtg ggtagatctt      420
gaattgaacg agctcaatcc gcgtatttaa acccgccccg cttcctcatt cttccttgtc      480
catttcaact ctccctctct ccctctcttc tgcccctcga tcgatccagc gatcttccta      540
tttccggacg cggggagcag ctcctcttgt cgaaggttct aaattagtgt ggagag          596
```

<210> SEQ ID NO 104
<211> LENGTH: 653
<212> TYPE: DNA
<213> ORGANISM: Eucalyptus grandis

<400> SEQUENCE: 104

```
aaaattttcc tttattttct tttcattaaa aagataaata aataaaaaaa aaaagaagg        60 aaaacacatc gaggtgaggc ttaaaggtgc taggcaagga ccaccaagcc tacacaaggg      120
tcggcgaccc tcaccaatgc tggggcgagg gtgagcaacc ctcatccaaa tctggagagg      180
gttgtcactc gagaaagggt cactggccct cccctaaccg ctactaacat cgttggcctt      240
cgtcaccacc gcactaacaa tgggccacta attttatatt tttcgtgata ttaatcctat      300
taaaaatgaa atatctcct taattaatta agcttgtcag gaccgatgta aacaaaatta       360
atgtaaatgg acgcgccttt gacttgccaa caaactcgaa acgacgtttc ctccgtctga      420
taactatctc gcgacctccg acgacatccg acggtgcaga tcgggtcccg gtcaaccatc      480
```

| | |
|---|---|
| cagatccacc cgattttctc ccggccctcg acaactccca ccaccacctc tttcctccct | 540 |
| ctttccttcc ttcctttctc accagatttt cccgagaaaa tcacagagag agaaagaaaa | 600 |
| acctcaccgc ctagagagag aaagagagaa agagggaaga gagagagaga gag | 653 |

<210> SEQ ID NO 105
<211> LENGTH: 342
<212> TYPE: DNA
<213> ORGANISM: Eucalyptus grandis

<400> SEQUENCE: 105

| | |
|---|---|
| agttgggtaa ccagtctaat tctggtaaca ttgcattgta cttgatctca ataaaagcat | 60 |
| ataggataga attatcttct gtcttgatgg tttccatgag aaccaactgc tatactatga | 120 |
| aaaatatcaa tgttccacaa tattttcggg acaagggaac acaagattga gtcaacagtt | 180 |
| caggacccca gaaaaattat tcctgagttc gcagattatt ttcctaaaag tgaacaattc | 240 |
| aagaccctag ccaaatcatt cccaagtcca agttatgtga cactgcgact aacaaggcaa | 300 |
| gttggaagaa accatcaatc aatctcctag ttaatgacag tc | 342 |

<210> SEQ ID NO 106
<211> LENGTH: 342
<212> TYPE: DNA
<213> ORGANISM: Eucalyptus grandis

<400> SEQUENCE: 106

| | |
|---|---|
| ggtctggaag ctcatctctc caatttggtg aagattacag ctataagagg tagctatgat | 60 |
| gtgctggcca aatgcaagtg atgaaatacg tggaccacca agtgcgaagg cattcgaaga | 120 |
| acgagggtcg aatttatagt gggcgaagga tgattaggtg gaatatgaca agaaaatagg | 180 |
| tttgaaagag aaataaatat tatgatagtg aagggtcttc acatggttag tttgatctgt | 240 |
| ccgagggtgt ccacccttgt ctgatccgca attgctcttg gtcgtgctga attttagagt | 300 |
| gtagccaaag taagaatttt cctttcactg tccggacatt tc | 342 |

<210> SEQ ID NO 107
<211> LENGTH: 948
<212> TYPE: DNA
<213> ORGANISM: Eucalyptus grandis

<400> SEQUENCE: 107

| | |
|---|---|
| ctgacaaatg caaatatcta aaaccattgg ttgtttggtg cttgcaagtc tggattaccc | 60 |
| cactttatgt ttcaccttc aataatgaat aacaaggtac tcgggaaaaa aaggaaaggg | 120 |
| aaattcgcac aaccaaagtt gctatgcaga agtcaactca atcctaatca agttgatgag | 180 |
| agtgttgggc cctatttct gcagcaaaca tgaatctcga ttcatctccc tcgcaaaaga | 240 |
| taaggaagct gcaaaagctt tcctcctaag tttgttggca agcaaattga ttttgtacca | 300 |
| gaaataaata caaagtgaaa cccaagcaat cacgcatggc ctgatttgtg ccatgtccat | 360 |
| ttgatctccc tctactattt ttcctgcttt ctcaagcaaa ctagttgctg taacagtgaa | 420 |
| tgatccccg gctctctctc tctctctctc tctctctctc catttattcc atccatgttt | 480 |
| ttgcttttcg cacaacactt atcattgagg tgctaactac tgaattcccc taactaaaaa | 540 |
| ttggaacctc tcacctaatt tcattttctc ccactttgat gagcaccact ctctttccca | 600 |
| gatttcaaat aaattgccac tctctccctc ctctttcctc acacaaccaa agccttctt | 660 |
| caagtaccac ttcttcactg tcctctcttc acaatccccc tcttaccaag agcaaagcaa | 720 |

```
aaaacatgat gaagagactg tcatttctgc tcctactggt cctgctcttc caatgctcta    780
ccaccttggc tcagcctgcg gccgcccag ctccgcctgt gatagcccg gctgcacctg     840 ctacgcctgc cttaggcccg gctcctcctg tcttaggccc agctcctgca ggcccaaccg    900
acatcacgaa ggtcctcaag aaggtgagcc aatttacggt gctgctca              948
```

<210> SEQ ID NO 108
<211> LENGTH: 362
<212> TYPE: DNA
<213> ORGANISM: Eucalyptus grandis

<400> SEQUENCE: 108

```
ccatcactca taatcaacaa ggatatctca tcatgtcttc caaccaaatt aaaccccaga    60
catctctaaa gcagtatgga aagaaaaca gtccggaagt ctctagctca aaaactgtaa    120
ccccgaccta attccggttg tctctgatta catcaattct tatgtcttaa cactccattc    180
gcacctccac aataaataga tcggcccttc atctccccct accatcgaat ccaatcccaa    240
aaacacttgc tcagacacca tcaaatcctt cgcaaagtct ttttcttaca aaaacaaac    300 gaaagcaacc atgaagcacc agttcattgt tctggctctc ttattcctca tcaacacagc    360
cc                                                                  362
```

<210> SEQ ID NO 109
<211> LENGTH: 326
<212> TYPE: DNA
<213> ORGANISM: Eucalyptus grandis

<400> SEQUENCE: 109

```
aaaaattaca atcaatggtt atcaatggat gttacaaagg gaggttacat atagaggtta    60 taaagaggg ttacaaatag atgtctcaaa caattaccaa gcggttagat tgactccact    120
attttgacgg ttctcttgac tttactatct caacgattac tttatttcat catgttgacg    180
gttgcatcca tgattgttga cttcactttt tgtcgattcc ttcaagctgc tgattcttca    240
agttgccaat aattttattc ataaatgacg aaactctagc ctcatccatt aagtttgtta    300
cttgtccaca ataattaaat tcggta                                        326
```

<210> SEQ ID NO 110
<211> LENGTH: 296
<212> TYPE: DNA
<213> ORGANISM: Pinus radiata

<400> SEQUENCE: 110

```
tgctcccggt catgacaccg ccattctcgc tcttcatttc caattcaaat cacttggttg    60
ttgttcacac acacgggtct ttatatgacg agtgctgctg cgattataaa tagacggggc   120
aattacaaca aaactcaca gcatttgaag gaagttggag tggtagagtg agaaatacac    180
agcctaatct gaaggaagtt cgagtaatag agtgagaaat ggatcttctt ctcctcatga    240
tgatgcttgt gatgatgggt gtagcaatgc ctactcattc tcaacaaatc actagt       296
```

<210> SEQ ID NO 111
<211> LENGTH: 723
<212> TYPE: DNA
<213> ORGANISM: Pinus radiata

<400> SEQUENCE: 111

```
cgttttacgc gggaacaatg aaaacagtac aatcgaaaga gtcaagtcgt gaggttcatt    60
tcgatgaagt tcccagagat tgtctcgttc aacgtttcct ctttttttcgg gtcaagtcgg   120
```

```
gtacagaaga ccactttctt tacgcggtca agacaccgcc attctcgggt caagtcggga      180
ggtccctcct gctcttcctt tttccaaatc cgtaaaattt acagattttt ttaatgtatg      240
aagcccactt tctttatgcg gttgctccca gtcaagacac cgccattgtt gttcacacgc      300
acgggtcttt atatgacgag tgctgctgcg attataaata gacggggcaa ttacaacaaa      360
aactcacagc atttgaagga agttggagtg gtagagtgag aaatcatttg aagggagttg      420
gagtggtaga gtgagaaatc atttgaaggg agttgagaaa tatattggga atctctcttt      480
tttgcagcaa ttagatcttt cctttaatgc tttgagtggg agaattccga cagagtttgg      540
gaacctctct cttttgcggc aataagttgg agtggtagtt ggagtggtag agtgagaaat      600
acacagccta atctgaagga agttggagtg atagagtgag aaatggatcg tcttcttctc      660
ttcatgttga tgcttgtgat gatgggtgta gcaatgccta ctcattctca acaaatcact      720
agt                                                                  723

<210> SEQ ID NO 112
<211> LENGTH: 1301
<212> TYPE: DNA
<213> ORGANISM: Pinus radiata

<400> SEQUENCE: 112
actatagggc acgcgtggtc gacggccctg gctggtagcg acagagctgg ttcagtgacc       60
gttcgtgatt agccgcagta aaacaaaacc ctaaccgtaa ccctttcgcg cagattccat      120
ccttccccgt cctaccaaaa cccaaacttc ttgcccgaac tcaccttcta tgtattaatt      180
cttattatta tttaataata ataaatagtt aaacataaat ttataaatta attaattttt      240 atgatttta ttttagttta aaaatgtgac attgttatag attaatgctt atgaacgttt       300
attggccata attaccctaa ttaattataa ttaaaatata tagttataat taaaaaattg      360 tatatttat aaattgaatt aagaatttct gatgatattt catcattcaa ttccatctta       420
tcaaagttag agggaatagt taaccatgta ctagatctat tcatagctaa catttgccaa      480
gttcgtacta ggagacttgg atttttttta aaacataatt ttggcagtaa aaagtgaatt      540
ctattgtttt gaaaacaaaa caaaatacag gaagcgtgat tgtgggggttg ttgttgaact      600 tgcccgggca aaagaagaat gattagcggt agaggagtta gtagttacgt tcaactaaat      660
gcgtgactaa attatttatc ctccgccatg gaagcaggtg attcacacac aacttgctgc      720
acacattgct ctcaaaacctt tcctataaat atccgtagca ggggctgcga tgatacacaa      780
cgcatttaat caaactactt tgattacttt ctgtgggttc tactttcttt gaatagtcag      840
ttctgctgtt tttagaagat ttataagaat ggccaaaatt caggtatcaa acgggaacgt      900
cgtggtggtg gctgcgatgt tatttatggt ggtggtggcc atgcaaaacc atcacgtcgc      960
cgcccaaagt gctgactgcg ccgccaccgc ggagtccctg agccctgcg cctcggcggt     1020 gggaaacaac ccacaggatc ccactcccga atgctgtgct gttcttcaga ccgctaatgt     1080
cgactgcatc tgcgccctcg tccaatcaac catgcaattg ccttccgaat gcggtcttga     1140
gactcctcag tgcccaagcg actagggtct caagaccgtg actgagtgct ggtttcagag     1200
acagtagaca ttctgcctaa taatgattg tatgagagct tttatatatg gaattgctca     1260
tatgctttcc tagatatgaa attattaaat tccatatgct t                        1301

<210> SEQ ID NO 113
<211> LENGTH: 3070
<212> TYPE: DNA
```

-continued

<213> ORGANISM: Eucalyptus grandis

<400> SEQUENCE: 113

```
agcaccatca gcaaaaaata gatgggatag agtgggacac cacctgttca gtttgattcc      60
cttgagatga cctacagtga tagcttgatg aataagatgg gataatagat tcaccagagg     120
gataaaaagg tagggagata ggggatctcc ccgtctgatg cctcgggtag gttgaaaata     180
aggcaaaagt tcgccgttga atttgacagc aaaagacacc gtcgttatgc attgcatgat     240
ccattgtacc catgtagggt gaaatcctag agtgaggaga tagtccttta gaaagtccca     300
ttccacccta tcataggctt tctgcatatc cattttaaga acagcccgga attgacgtct     360
acattttctg actttaaatt gatgtagaac ctcttagact attaaaatat tgtcctgaat     420
ttgacgtcca ctgacaaaag cgctttgctc ctggaaaata agtacaggca ggtagggctt     480
aaggcgattg gcaatcacct tagaaatgat cttatatgcg taattacaaa gactgatggg     540
gcggtattgg tctaattgtt caggatgtgg taccttgggt attagggcta tgatggttcg     600
attgagattc ggtggtatga tgccagaatt aaaaaagtgc tgcactgatg agaatagttc     660
atcctggagt atatcccaat gatgctggta gaagagtcca ttcaagccat ctggaccggg     720
ggccttggta agtcccagtt ggaaagtagc ctctctaact tccttcttgg taacaggagc     780
tattagggac atattcatct cattagtaac aacctaagga cactggttca gaataggcaa     840
gtagtctcga tgtcccactg tctgaaatag atgtgaaaag taacctatcg tcatcatctt     900
caaaatttca ggatcgcgca cccaagcttg attgtcatcc tgcaacatac taatcttgtt     960
tcgttgttgt ctttgtatag ttgttgcatg aaaaaattta gtatttttgt ccccccagct    1020
gagccattta attcgagagc acatcgccca aaattattct tcttgctgcc ataactgtcg    1080
aattttctct tttaggtaag taaccaatga tgcgccatgt tgacaaaaag gctgattagt    1140
atgatcttgg agttgttggt gcaaatttgc aagctgacga tggcccctca gggaaattaa    1200
ggcgccaacc cagattgcaa agagcacaaa gagcacgacc caacctttcc ttaacaagat    1260
catcaccaga tcggccagta aggtaatat taatttaaca aatagctctt gtaccgggaa    1320
ctccgtattt ctctcacttc cataaacccc tgattaattt ggtgggaaag cgacagccaa    1380
cccacaaaag gtcagatgtc atcccacgag agagagagag agagagagag agagagagtt    1440
ttctctctat attctggttc accggttgga gtcaatggca tgcgtgacga atgtacatat    1500
tggtgtaggg tccaatattt tgcgggaggg ttggtgaacc gcaaagttcc tatatatcga    1560
acctccacca ccatacctca cttcaatccc caccatttat ccgttttatt tcctctgctt    1620
tcctttgctc gagtctcgcg gaagagagag aagagaggag aggagagaat gggttcgacc    1680
ggctccgaga cccagatgac cccgacccaa gtctcggacg acgaggcgaa cctcttcgcc    1740
atgcagctgg cgagcgcctc cgtgctcccc atggtcctaa aggccgccat cgagatcgac    1800
ctcctcgaga tcatggccaa ggacgggccg ggcgcgttcc tctccacggg ggaaatcgcg    1860
gcacagctcc cgacccagaa ccccgaggca cccgtcatgc tcgaccggat cttccggctg    1920
ctggccagct actccgtgct cacgtgcacc ctccgcgacc tccccgatgg caaggtcgag    1980
cggctctacg gcttagcgcc ggtgtgcaag ttccttggtca agaacgagga cggggtctcc    2040
atcgccgcac tcaacttgat gaaccaggac aaaatcctca tggaaagctg gtattacctg    2100
aaagatgcgg tccttgaagg cggaatccca ttcaacaagg cgtacgggat gaccgcgttc    2160
gagtatcatg gcaccgaccc gcgattcaac aagatctttta accggggaat gtctgatcac    2220
tccaccatta ctatgaagaa gatactggaa acatacaagg gcttcgaggg cctcgagacc    2280
```

```
gtggtcgatg tcggaggcgg cactggggcc gtgctcagca tgatcgttgc caaatacccca      2340 tcaatgaaag ggatcaactt cgaccgcccc aacggattga agacgcccca ccccttcctg      2400
gtgtcaagca cgtcggaggc gacatgttcg tcagcgttcc aaaggagat gccattttca       2460 tgaagtggat atgccatgac tggagtgacg accattgcgc gaagttcctc aagaactgct     2520
acgatgcgct tcccaacaat ggaaaggtga tcgttgcaga gtgcgtactc cctgtgtacc     2580
cagacacgag cctagcgacc aagaatgtga tccacatcga ctgcatcatg ttggcccaca     2640
acccaggcgg gaaagagagg acacagaagg agttcgaggc attggccaaa ggggccggat     2700
ttcagggctt ccaagtcatg tgctgcgctt tcggcactca cgtcatggag ttcctgaaga     2760
ccgcttgatc tgctcctctg tggtgatgtt catggttctt ggatttgaaa ggtcgtgaag    2820
gagccctttt ctcacagttg gcttcggcat accaagttct tctcataaaa ggaaacaata   2880
agaagcgact gtatgatggc gcaagtggaa gttacaagat ttgttgtttt atgtctataa   2940
agttttgagt cttctgcata ctgatttcac agaatgtgta acgaaacggc gtatatggat   3000
gtgcctgaat gatggaaatt gtgatattct gtcttctttt tcagtaaatc acttcgaaca   3060
aaaaaaaaaa                                                           3070

<210> SEQ ID NO 114
<211> LENGTH: 1227
<212> TYPE: DNA
<213> ORGANISM: Pinus radiata

<400> SEQUENCE: 114
aaatttcaag aggaagagat taattctttt aatttataaa attatataat aaaatattta      60
tatttaattt agatgataag tttatgaggt gtagaataga tagtgatggg tgtattattg     120
agttattccc ctaatgtgga gacaattgat tagaagttct atgagaaaaa tccaatcatg     180
ttaaagtgac ccctaatgtg aagacaattg attagaaatt ctatgaaaaa aatccaatca     240
tattaaaagt ccaattgatt agcaattta tgagaaaaat ccaattatgt taaaagtcac     300
tgagtgtggc cgaaattgtg accgaaattg aatgcaataa ccgagggttt ttcaaaccaa     360
ggttaagcct ctcatcattg gggtgtgtat gaaaatgtaa tgggcatcga taacctttta    420
ttacaacttc acgaaaattg cctctattca atgggtgtgg atgaaaatgt aagtgcgcat    480
cgataatgga aagcgatatg cagcaaaatc aataaacctg acttcccatg tgagtgatga    540
tttgatcgta caactgatgg tgtgaagtta ctttcagctt caccttcggg cataatcagg    600
gaagtagggc caagtttgct tagtatcact ctaatcccca acaccgtgat tactatcttc     660
atcaacaatg gccaccttcg tcattacttt aactggtggg atacagctac tttacaactg   720
taaatttgtt gaggcagcct atcctcagcc tatacatact aattattgca gctcgattag    780
gtatctgctg tgagaatagc tgtgtatctc tgcgctggtt gcaggatcca agttcctctc   840
agagccctcc atggaagcgc agtcagtttc agttgttgag cagcgccccc atgccctact    900
attttcattt ccgttacagg gccacatcaa gcctttcatg aacttggcca agattttgtc   960 cagccgggc ttctatgtca cttttgccag taccgaattt gttgtaaagc gcctcgcaga    1020
atgtggtgaa agtatcgccc atcgtgattc gatggtgtgc agcgagaacg atgatgtatg    1080
taacataaaa tttgaaacag tgcccgacgg actgcctccc caccacgatc gcagtactca    1140
gaatcttgcg gagctcttcc aatccatgga agagaacgct catattcact tccacaagtt    1200
gatggagaag ctccagaatc ttcggga                                         1227
```

<210> SEQ ID NO 115
<211> LENGTH: 1169
<212> TYPE: DNA
<213> ORGANISM: Eucalyptus grandis

<400> SEQUENCE: 115

| | | | | | |
|---|---|---|---|---|---|
| ttcattatat | gattattacg | tcataatgat | cgatttctag | aaatttggag | acatatgtaa | 60 |
| attcaggagg | aatttcaaga | aacgcgcgtt | actttgaaag | ggtctcgagt | caaagtgctc | 120 |
| aaattgagag | ggagaatttt | agaacaaaat | cagatttgga | gaatacatgc | cattttaggg | 180 |
| ggattttggg | gatttcgcat | atggcgtcgc | gtcgtcggcg | ccttcttctt | tacagattgt | 240 |
| atcctcccat | taaccgcgtg | gacctgcata | gggcacgcgt | ggtcgacggc | ccgggctggt | 300 |
| ttcattatat | gattattacg | tcataatgat | cgatttctag | aaatttggag | acatatgtaa | 360 |
| attcaggagg | aatttcaaga | aacgcgcgtt | actttgaaag | ggtctcgagt | caaagtgctc | 420 |
| aaattgagag | ggagaatttt | agaacaaaat | cagatttgga | gaatacatgc | cattttaggg | 480 |
| ggattttggg | gatttcgcat | atggcgtcgc | gtcgtcggcg | ccttcttctt | tacagattgt | 540 |
| atcctcccat | taaccgcgtg | gacctgcact | gtaacccga | aacggtgggg | gccaatttcg | 600 |
| tctttccgcc | tcctccactc | agcttcgtgg | aagattaaaa | tcctcaccgt | ccgtgcaaac | 660 |
| gccacgtggc | gcgttagttt | gcgcgtggaa | aggtcctcac | gaaccgtaaa | gggcaaaaaa | 720 |
| aagggaaaat | aaaaaaggag | gaggaggagg | gaggaggaag | aattgtccga | ttgaaaataa | 780 |
| gagtgcggtg | gtgtggtgtg | ggtagatctt | gaattgaacg | agctcaattc | gcgtatttaa | 840 |
| acccgccccg | cttcctcatt | cttccttgtc | catttcaact | ctccctctct | ccctctcttc | 900 |
| tgcccctcga | tcgatccagc | gatcttccta | tttccggacg | cggggagcag | ctcctcttgt | 960 |
| cgaaggttct | aaattagtgt | ggagagatgg | tgaagatctg | ctgcattggt | gctggctatg | 1020 |
| tcggcgggcc | tactatggcc | gtgattgctc | tcaagtgccc | gtcagtagaa | gttgcggtcg | 1080 |
| ttgatatttc | tgtctctcgc | atacaagcct | ggaacagcga | acagctccct | atctatgaac | 1140 |
| caggccttga | tgcggtggtg | aagcaatgc | | | | 1169 |

<210> SEQ ID NO 116
<211> LENGTH: 947
<212> TYPE: DNA
<213> ORGANISM: Eucalyptus grandis

<400> SEQUENCE: 116

| | | | | | |
|---|---|---|---|---|---|
| ggtctggaag | ctcatctctc | caatttggtg | aagattacag | ctataagagg | tagctatgat | 60 |
| gtgctggcca | aatgcaagtg | atgaaatacg | tggaccacca | agtgcgaagg | cattcgaaga | 120 |
| acgagggtcg | aatttatagt | gggcgaagga | tgattaggtg | gaatatgaca | agaaaatagg | 180 |
| tttgaaagag | aaataaatat | tatgatagtg | aagggtcttc | acatggttag | tttgatctgt | 240 |
| ccgagggtgt | ccacccttgt | ctgatccgca | attgctcttg | gtcgtgctga | attttagagt | 300 |
| gtagccaaag | taagaatttt | cctttcactg | tccggacatt | tcgattgcta | catgaccat | 360 |
| cccgtgtcta | cccattcttg | agaaccttcg | agtggaaagc | atgaataacc | caccttgtac | 420 |
| tatataggtt | gccgaatatg | cctagggcgc | gaccatcatt | gagacggagt | tggggtgctc | 480 |
| cgctcggttc | accaccacca | ccaccaccac | caccaccacc | accaccattg | ggcactgata | 540 |
| tagcgactcc | accactaccc | caaccgaggt | tggcaaactc | tagattgtac | atgggatata | 600 |
| tcggagtagt | tgaacatgat | cagatcaatg | gtagtggtta | agactctaga | aattattgaa | 660 |
| gcaatatgtt | aaatcagata | cgtgtgagaa | agtgacttac | taattgctat | ggctttcatg | 720 |

| | |
|---|---|
| atacttaaac ttcaatgaat tggtaatgtg aagagcaatg tgatctccac aaatactact | 780 |
| agaaggccaa gtccttttct ttatgccgaa gtcctaaagt ttaatatttc aactctacct | 840 |
| atatcaaatt tgtatgcaaa ttgcataatc gcactgattt ctatggtttt attaatctag | 900 |
| ataagaactc tctccaagac attaactaat taagattgac cccattt | 947 |

<210> SEQ ID NO 117
<211> LENGTH: 1766
<212> TYPE: DNA
<213> ORGANISM: Eucalyptus grandis

<400> SEQUENCE: 117

| | |
|---|---|
| atccagatcc ctacgaactg gattcacaca gtcactgctg taagctctgg tttttttag | 60 |
| cttaggaagc aggttatgat caaacatgat taaaccatcg cgtgttcgcc agccatcaga | 120 |
| aatggaaagg caaatgttgt tatagtgatg acagatcat gctgagatga ttgattatga | 180 |
| atcttactga tgactgtcat ttatgttatc gcactctgtg tgtgtgggtg tgtgtaatga | 240 |
| gtaatatcaa attaaccaga cgataggtgt tgaagattag ctgttgggcc accgtggcga | 300 |
| aaggtgtctt atacaagcca tcggcagtga cgcagaactg tagagaaccg ctgtaacaag | 360 |
| tcttcgaatg cattctttta atgtacagca cgacatgaag ggggttcgag tgtagcgaac | 420 |
| agttcgtgcg agaaagatca ttttcaatag cataaaagag tctgctttct gctgcaaaca | 480 |
| tggaaagaac ttacatttca atcattgagg agaagattat aacaaatcct aaatggttga | 540 |
| gattttagtt agtccattcg aactaaagtg gcgaagatgt cagttttca agtggatgat | 600 |
| atttctcatg tatgttccgc agaggcaatc accttgtttg taactagaca tctagagaac | 660 |
| ctaacaagga ttgatggggg tgaggtgaaa tgtctgtttc ctctttaata tggatccagc | 720 |
| gatgccttac agagcggatg gatggcactg gcaagtctta atccttagct cgaatgtttg | 780 |
| attggtaaca gatgcctttt ctttcttttc aatcacagct gacaaatgca aatatctaaa | 840 |
| accattggtt gtttggtgct tgcaagtctg gattacccca ctttatgttt caccttcaa | 900 |
| taatgaataa caaggtactc gggaaaaaa ggaaagggaa attcgcacaa ccaaagttgc | 960 |
| tatgcagaag tcaactcaat cctaatcaag ctgatgagag tgttgggccc tattttctgc | 1020 |
| agcaaacatg aatctcgatt catctccctc gcaaaagata aggaagctgc aaaagctttc | 1080 |
| ctcctaagtt tgttggcaag caaattgatt ttgtaccaga aataaataca agtgaaacc | 1140 |
| caagcaatca cgcatggcct gatttgtgcc atgtccattt gatctccctc tactattttt | 1200 |
| cctgctttct caagcaaact agttgctgta acagtgaatg atccccggc tctccccctc | 1260 |
| tctctctctc tctctctcca tttattccat ccatgttttt gcttttcgca caacacttat | 1320 |
| cattgaggtg ctaactactg aattcccta actaaaaatt ggaacctctc gcctaatttc | 1380 |
| attttctccc actttgatga gcaccactct ctttcccaga tttcaaataa attgccactc | 1440 |
| tctccctcct ctttcctcac acaaccaaaa gccttcttca agtaccactt cttcactgtc | 1500 |
| ctctcttcac aatcccctc ttaccaagag caaagcaaaa aacatgatga agagactgtc | 1560 |
| atttctgctc ctactggtcc tgctcttcca atgctctacc accttggctc agcctgcggc | 1620 |
| cgccccagct ccgcctgtga tagccccggc tgcacctgct acgcctgcct taggcccggc | 1680 |
| tcctcctgtc ttaggcccag ctcctgcagg cccaaccgac atcacgaagg tcctcaagaa | 1740 |
| ggtgagccaa tttacggtgc tgctca | 1766 |

<210> SEQ ID NO 118

<211> LENGTH: 1928
<212> TYPE: DNA
<213> ORGANISM: Eucalyptus grandis

<400> SEQUENCE: 118

| | | | | | |
|---|---|---|---|---|---|
| ctggttccac | gtcaagcacc | tcctggagtg | acaaggaaat | gccaccggaa | aatcaagatt | 60 |
| gctgttttag | gctcactttt | ttcctgagct | aagtgggtcg | catttcaaga | aacagtagaa | 120 |
| gttacgttct | ccatggaaac | tcgaaaggat | aaaaattaag | aaacggaagc | tccatgagaa | 180 |
| cgatgggggt | cagcatcact | cctattgtat | tgtgctctca | ttatctctgg | cctacttgag | 240 |
| aagtgatctg | ggattcgcta | ttagtgaaaa | caatcgcagg | ctaactaaga | tcttttatgc | 300 |
| taatcatatg | gagaaatatc | cctcttaagg | gaagcatatg | agtttttttct | taggatgact | 360 |
| acgcttattc | aaaacctatc | atacacgtca | tgccaataat | acccacttgt | tgttccttta | 420 |
| ctcaggatcc | tcgatagcca | atactaattg | gcaagaacct | tgagtaacaa | gctgaggtat | 480 |
| acataggcct | atcattcatt | tactagactc | gattgcaagc | acacatgatg | cacatttata | 540 |
| tcagcaatca | gcaatcatat | ttccgaaaat | tgtctctcag | agaaaaagag | agagagagag | 600 |
| agtccatagt | atgtcatagc | caaagaaaa | attagcaaca | agatctcgag | gtattgttga | 660 |
| aaggtagggc | aatatcaaga | attccattgt | aattaatgtg | tctagacaac | atctaagaaa | 720 |
| aaaaagtgaa | agaaaagagc | tatatagtta | ataatattta | tacatgttgg | agataaactt | 780 |
| gagttagagg | tttatgacct | cctagattga | ttaaacagac | caaatagtag | taatcagggc | 840 |
| acttcttaaa | tctactaata | tattgttcaa | acatgacttt | taacctatct | tgattagaaa | 900 |
| tgagtgttca | agaaaacta | atcatgcata | tattttgtcg | cccaatcacc | ctagggtgga | 960 |
| aaaaaggcta | tctactcaac | aaatgctaaa | attttacggc | tacacgtggc | cacagttgca | 1020 |
| gtacaattca | tctcaaggaa | ggactaaaac | tgcaaagaga | agaagactac | ataggaaaaa | 1080 |
| ggaaaacaaa | gaagccttga | agtaaagagg | agcataactc | actcaactga | gtgtgttcgc | 1140 |
| caatgtggca | agaaaaagc | ctctaagatc | ctcacaaatg | gccacgtgga | ctcacacggc | 1200 |
| accctataca | agtactacta | ctactacagg | actatgccag | aaggagaagt | gttagcgtga | 1260 |
| gtaccacgtg | cgcacgcaga | atctaagcct | agcaaaaact | atgctgagtc | aagcagctcc | 1320 |
| cccacccatg | aagatagtac | tgtaatgtga | ctcttgacag | cgaaaccaaa | cagtactcca | 1380 |
| agagaaaagc | caaagcagca | aaaatggggc | ccgcagcaag | aacctctgac | tcgacctgga | 1440 |
| cccaccaaga | acaacagcca | gccacaaaat | aacgtaaaga | cttttttgcgg | ccactaactc | 1500 |
| ctcgacaagt | ggcactgctt | ggattcccctt | catcttgcct | tcacttaacc | cccaccctcc | 1560 |
| ctcacactgc | attcacttca | aacactcccc | agtttcagag | tttcattgag | aaatatgttg | 1620 |
| aaggaagaca | cgagtggcag | cggcggcagc | agcggcagcg | gcagcggtgg | taatagctgg | 1680 |
| gcacgtgtgt | gtgacacttg | ccgctcggca | gcatgcaccg | tgtactgccg | tgccgacttg | 1740 |
| gcttacctat | gctccagctg | tgacgctcgt | attcacgcag | ccaccgtgtg | gcctcgcgcc | 1800 |
| atgagcgcgt | gtgggtgtgc | gaagcgtgcg | agcgcgcccc | ggctgccttc | ctctgcaagg | 1860 |
| ctgatgcagc | atcactgtgc | accgcctgcg | atgcagacat | acactcagcc | aacccgcttg | 1920 |
| cgcgccgc | | | | | | 1928 |

<210> SEQ ID NO 119
<211> LENGTH: 602
<212> TYPE: DNA
<213> ORGANISM: Eucalyptus grandis

<400> SEQUENCE: 119

-continued

```
attgggagga agtagagtgt gctgtgtgag attggtcgat gagctggctc ttgtggagat      60
ggcaagtgat tgtggcttct gtgatgcata tatataggca agggacgtga tgcggaggaa     120
gtatgtatca tcagcttata ataatgattg gtcagtttgt aagtgaatat taagggcctc    180
atgggtgttg gttcacggcc caaggcgggg cccactcacc gggggattta tcgtgtaagg     240
atacatccag ggtcagggtg tttggggaca cactttgcca tcttatgtgg gcatgatcag     300
attgagaaga atccgatcct tcttttcct aaaccattga acccaccatg agaatctttg      360
tttgagggga aaataaaaa aatagattga gacgtattct aggagaggat agcaaaagaa     420
tgtgactttg tttgtttgtg tatcggattg atctaaggaa aaaagacact aaccgttcta    480
caattttcat acaactcttt catttaagca ccgtgacttc caaaaatcga tcatccttat    540
acggttggaa atcacacgtg gcattgctgt aaaagaaata gttgatgggt ctcattgaag    600
at                                                                    602
```

<210> SEQ ID NO 120
<211> LENGTH: 1326
<212> TYPE: DNA
<213> ORGANISM: Pinus radiata

<400> SEQUENCE: 120

```
aaaaaaggga acattatac caaatttat gatatctttc aacaacatac tcttctatat      60
atggtgcctc ctctgatgga cccttgtcaa cttctctttt ttatgtgtaa tgcctcaaga    120
gcccccactc acaagataat atcttttcca taatataata tatattccta ttgaagcagt   180
cttttgatgt accgagtaca ctactcatgg tgaaggccgt gtcttgcagc ttttccatg    240 gtttatttg aaagtaatag tactggacct catttgcaac gacacataat attcttactg     300
acgacacttt gtttgatttc ttatagaaaa atgcaaggtg gcacaaaaag atggaaagcc    360
cgacctatca agcatacgaa gggtcatgtt cacaccctct gaaatcttca gagtctcacc    420
ctatgttgga cgctaatcaa tgggatcacg ctgaaacata tcgtaaatga cgaatcaatc    480
aatcaatcat tgaaaaatat accagataac tcctacgatg gagggattaa tttgcgtacc     540
ctccgcgtgg gtgggcacat tgggcaggtc cttttggtaag tcttggagac agagtcacgt   600
ttccataatt gaagtggaca tttatgaatc tttcgaaagt tgtagaactc ttaattttcg    660
acggaatagt ttgacacgtt ttgtacgatc tggttttcc ggggaacgcc aattttggtt     720
tctgaaggac agcatttaca atattgtctg tcgttgacca ggacagctgg ctcggaactc   780
gggtttccga tgcgcaggaa gcgcattgaa atgagaatat aatctagttc tacctgtgga    840
gctatcacaa aatactaaaa ctggtggaca tacctcttgt ctgttctcga aatcggccaa    900
aatgggaaag aagagggtag agctgaaacg cattcaaaac cctagcagtc gacatgctac    960
tttctctaaa cgcaagaatg gattgctaaa aaaggcgttc gagctttctg tcctctgtga   1020
tgctgaagtc gctctcatca ttttctctga aactggcaag atttacgaat ttgcgagcaa   1080
taacgatatg gcagcaattc tgggaaaata ccgagtacac gaagaaggca ctgaaacgtc   1140
cagtccaaca tcgcttcaaa acgtaaagta tcatgaatca gggcttgaga aattgcaaga   1200
gaagttgacc gctttgcaaa agaaggaaaa gaacttgatt ggtgaagact ggaggtatt    1260 aacaatgaaa gaactgcaac ggcttgaaaa acagttacaa attggcataa aaaggttagt   1320
gataga                                                              1326
```

US 6,596,925 B1

COMPOSITIONS AND METHODS FOR THE MODIFICATION OF GENE EXPRESSION

CROSS-REFERENCE TO RELATED APPLICATIONS

This application claims priority to International Patent Application No. PCT/NZ00/00018, filed Feb. 24, 2000, and to U.S. patent application Ser. No. 60/146,591, filed Jul. 30, 1999, and is a continuation-in-part of U.S. patent application Ser. No. 09/276,599, filed Mar. 25, 1999 now U.S. Pat. No. 6,380,459.

TECHNICAL FIELD OF THE INVENTION

This invention relates to the regulation of polynucleotide transcription and/or expression. More specifically, this invention relates to polynucleotide regulatory sequences isolated from plants that are capable of initiating and driving the transcription of polynucleotides, and the use of such regulatory sequences in the modification of transcription of endogenous and/or heterologous polynucleotides and production of polypeptides. Polypeptide sequences are also disclosed.

BACKGROUND OF THE INVENTION

Gene expression is regulated, in part, by the cellular processes involved in transcription. During transcription, a single-stranded RNA complementary to the DNA sequence to be transcribed is formed by the action of RNA polymerases. Initiation of transcription in eucaryotic cells is regulated by complex interactions between cis-acting DNA motifs, located within the gene to be transcribed, and trans-acting protein factors. Among the cis-acting regulatory regions are sequences of DNA, termed promoters, to which RNA polymerase is first bound, either directly or indirectly. As used herein, the term "promoter" refers to the 5' untranslated region of a gene that is associated with transcription and which generally includes a transcription start site. Other cis-acting DNA motifs, such as enhancers, may be situated further up- and/or down-stream from the initiation site.

Both promoters and enhancers are generally composed of several discrete, often redundant elements, each of which may be recognized by one or more trans-acting regulatory proteins, known as transcription factors. Promoters generally comprise both proximal and more distant elements. For example, the so-called TATA box, which is important for the binding of regulatory proteins, is generally found about 25 basepairs upstream from the initiation site. The so-called CAAT box is generally found about 75 basepairs upstream of the initiation site. Promoters generally contain between about 100 and 1000 nucleotides, although longer promoter sequences are possible.

For the development of transgenic plants, constitutive promoters that drive strong transgene expression are preferred. Currently, the only available constitutive plant promoter that is widely used is derived from Cauliflower Mosaic Virus. Furthermore, there exists a need for plant-derived promoters for use in transgenic food plants due to public conceptions regarding the use of viral promoters. Few gymnosperm promoters have been cloned and those derived from angiosperms have been found to function poorly in gymnosperms. There thus remains a need in the art for polynucleotide promoter regions isolated from plants for use in modulating transcription and expression of polynucleotides in transgenic plants.

SUMMARY OF THE INVENTION

Briefly, isolated polynucleotide regulatory sequences from eucalyptus and pine that are involved in the regulation of gene expression are disclosed, together with methods for the use of such polynucleotide regulatory regions in the modification of expression of endogenous and/or heterologous polynucleotides in transgenic plants. In particular, the present invention provides polynucleotide promoter sequences from 5' untranslated, or non-coding, regions of plant genes that initiate and regulate transcription of polynucleotides placed under their control, together with isolated polynucleotides comprising such promoter sequences.

In a first aspect, the present invention provides isolated polynucleotide sequences comprising a polynucleotide selected from the group consisting of: (a) sequences recited in SEQ ID NO: 1–14, 20, 22–62, 81–86 and 88–120; (b) complements of the sequences recited in SEQ ID NO: 1–14, 20, 22–62, 81–86 and 88–120; (c) reverse complements of the sequences recited in SEQ ID NO: 1–14, 20, 22–62, 81–86 and 88–120; (d) reverse sequences of the sequences recited. in SEQ ID NO: 1–14, 20, 22–62, 81–86 and 88–120; (e) sequences having either 40%, 60%, 75or 90% identical nucleotides, as defined herein, to a sequence of (a)–(d); probes and primers corresponding to the sequences set out in SEQ ID NO: 1–14, 20, 22–62, 81–86 and 88–120; polynucleotides comprising at least a specified number of contiguous residues of any of the polynucleotides identified as SEQ ID NO: 1–14, 20, 22–62, 81–86 and 88–120; and extended sequences comprising portions of the sequences set out in SEQ ID NO: 1–14, 20, 22–62, 81–86 and 88–120; all of which are referred to herein as "polynucleotides of the present invention." The present invention also provides isolated polypeptide sequences identified in the attached Sequence Listing as SEQ ID NO: 63–80 and 87; polypeptide variants of those sequences; and polypeptides comprising the isolated polypeptide sequences and variants of those sequences.

In another aspect, the present invention provides genetic constructs comprising a polynucleotide of the present invention, either alone, or in combination with one or more additional polynucleotides of the present invention, or in combination with one or more known polynucleotides, together with cells and target organisms comprising such constructs.

In a related aspect, the present invention provides genetic constructs comprising, in the 5'-3' direction, a polynucleotide promoter sequence of the present invention, a polynucleotide to be transcribed, and a gene termination sequence. The polynucleotide to be transcribed may comprise an open reading frame of a polynucleotide that encodes a polypeptide of interest, or it may be a non-coding, or untranslated, region of a polynucleotide of interest. The open reading frame may be orientated in either a sense or antisense direction. Preferably, the gene termination sequence is functional in a host plant. Most preferably, the gene termination sequence is that of the gene of interest, but others generally used in the art, such as the *Agrobacterium tumefaciens* nopalin synthase terminator may be usefully employed in the present invention. The genetic construct may further include a marker for the identification of transformed cells.

In a further aspect, transgenic plant cells comprising the genetic constructs of the present invention are provided, together with organisms, such as plants, comprising such transgenic cells, and fruits, seeds and other products, derivatives, or progeny of such plants. Propagules of the inventive transgenic plants are included in the present invention. As used herein, the word "propagule" means any part of a plant that may be used in reproduction or propagation, sexual or asexual, including cuttings.

Plant varieties, particularly registerable plant varieties according to Plant Breeders' Rights, may be excluded from the present invention. A plant need not be considered a "plant variety" simply because it contains stably within its genome a transgene, introduced into a cell of the plant or an ancestor thereof.

In yet another aspect, methods for modifying gene expression in a target organism, such as a plant, are provided, such methods including stably incorporating into the genome of the organism a genetic construct of the present invention. In a preferred embodiment, the target organism is a plant, more preferably a woody plant, most preferably selected from the group consisting of eucalyptus and pine species, most preferably from the group consisting of *Eucalyptus grandis* and *Pinus radiata*.

In another aspect, methods for producing a target organism, such as a plant, having modified polypeptide expression are provided, such methods comprising transforming a plant cell with a genetic construct of the present invention to provide a transgenic cell, and cultivating the transgenic cell under conditions conducive to regeneration and mature plant growth.

In other aspects, methods for identifying a gene responsible for a desired function or phenotype are provided, the methods comprising transforming a plant cell with a genetic construct comprising a polynucleotide promoter sequence of the present invention operably linked to a polynucleotide to be tested, cultivating the plant cell under conditions conducive to regeneration and mature plant growth to provide a transgenic plant; and comparing the phenotype of the transgenic plant with the phenotype of non-transformed, or wild-type, plants.

In yet a further aspect, the present invention provides isolated polynucleotides that encode ubiquitin. In specific embodiments, the isolated polynucleotides comprise a polynucleotide selected from the group consisting of: (a) sequences recited in SEQ ID NO: 1 and 34; (b) complements of the sequences recited in SEQ ID NO: 1 and 34; (c) reverse complements of the sequences recited in SEQ ID NO: 1 and 34; (d) reverse sequences of the sequence recited in SEQ ID NO: 1 and 34; and (e) sequences having either 40%, 60%, 75% or 90% identical nucleotides, as defined herein, to a sequence of (a)–(d). Polypeptides encoded by such polynucleotides are also provided, together with genetic constructs comprising such polynucleotides, and host cells and transgenic organisms, for example plants, transformed with such genetic constructs. In specific embodiments, such polypeptides comprise a sequence provided in SEQ ID NO: 80 or 67.

In yet further aspects, the present invention provides isolated polynucleotides comprising the DNA sequence of SEQ ID NO: 21, or a complement, reverse complement or variant of SEQ ID NO: 21, together with genetic constructs comprising such polynucleotides and cells transformed with such sequences. As discussed below, removal of the sequence of SEQ ID NO: 21 from a polynucleotide that comprises the sequence of SEQ ID NO: 21 may enhance expression of the polynucleotide. Conversely, the inclusion of the sequence of SEQ ID NO: 21 in a genetic construct comprising a polynucleotide of interest may decrease expression of the polynucleotide.

The above-mentioned and additional features of the present invention and the manner of obtaining them will become apparent, and the invention will be best understood by reference to the following more detailed description. All references disclosed herein are hereby incorporated by reference in their entirety as if each was incorporated individually.

DETAILED DESCRIPTION OF THE INVENTION

Figure 1:
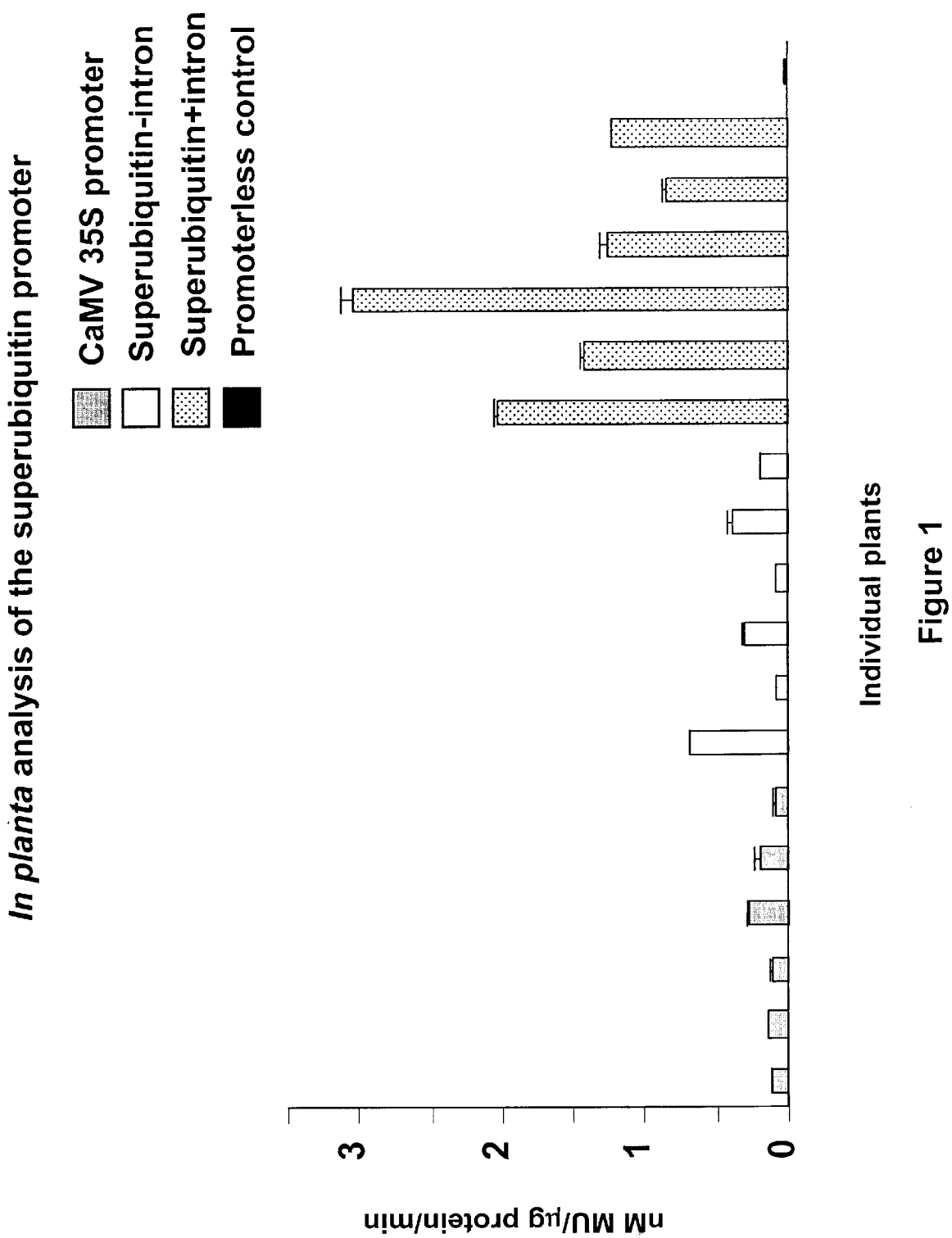
FIG. 1 shows the expression in *A. thaliana* of the GUS gene in promoter reporter constructs containing either the superubiquitin promoter with introns, the superubiquitin promoter without introns, or the CaMV 35S promoter. The GUS expression was measured by fluorimetric determination of 4-methyl-umbelliferone (MU) in protein extracts from these plants.

The present invention provides isolated polynucleotide regulatory regions that may be employed in the manipulation of plant phenotypes, together with isolated polynucleotides comprising such regulatory regions. More specifically, polynucleotide promoter sequences isolated from pine and eucalyptus are disclosed. As discussed above, promoters are components of the cellular "transcription apparatus" and are involved in the regulation of gene expression. Both tissue- and temporal-specific gene expression patterns have been shown to be initiated and controlled by promoters during the natural development of a plant. The isolated polynucleotide promoter sequences of the present invention may thus be employed in the modification of growth and development of plants, and of cellular responses to external stimuli, such as environmental factors and disease pathogens.

Using the methods and materials of the present invention, the amount of a specific polypeptide of interest may be increased or reduced by incorporating additional copies of genes, or coding sequences, encoding the polypeptide, operably linked to an inventive promoter sequence, into the genome of a target organism, such as a plant. Similarly, an increase or decrease in the amount of the polypeptide may be obtained by transforming the target plant with antisense, copies of such genes.

The polynucleotides of the present invention were isolated from forestry plant sources, namely from *Eucalyptus grandis* and *Pinus radiata*, but they may alternatively be synthesized using conventional synthesis techniques. Specifically, isolated polynucleotides of the present invention include polynucleotides comprising a sequence selected from the group consisting of sequences identified as SEQ ID NO: 1–14, 20, 22–62, 81–86 and 88–120; complements of the sequences identified as SEQ ID NO: 1–14, 20, 22–62, 81–86 and 88–120; reverse complements of the sequences identified as SEQ ID NO: 1–14, 20, 22–62, 81–86 and 88–120; at least a specified number of contiguous residues (x-mers) of any of the above-mentioned polynucleotides; extended sequences corresponding to any of the above polynucleotides; antisense sequences corresponding to any of the above polynucleotides; and variants of any of the above polynucleotides, as that term is described in this specification.

In another embodiment, the present invention provides isolated polypeptides encoded by the polynucleotides of SEQ ID NO: 63–80 and 87.

The polynucleotides and polypeptides of the present invention were putatively identified by DNA and polypeptide similarity searches. In the attached Sequence Listing, SEQ ID NOS. 1–14, 20, 22–62, 81–86 and 88–120 are polynucleotide sequences, and SEQ ID NOS. 63–80 and 87 are polypeptide sequences. The polynucleotides and polypeptides of the present invention have demonstrated similarity to promoters that are known to be involved in regulation of transcription and/or expression in plants. The putative identity of each of the inventive polynucleotides is shown below in Table 1, together with the 5' untranslated region (5' UTR) or putative promoter region (identified by residue number).

TABLE 1

| Polynucleotide SEQ ID NO: | Polypeptide SEQ ID NO: | 5' UTR | IDENTITY |
|---|---|---|---|
| 1 | 80 | 1-2064 | Super Ubiquitin coding region and UTR |
| 2 | — | 1-2064 | Super Ubiquitin promoter with intron |
| 3 | — | 1-1226 | Super Ubiquitin promoter without intron |
| 4 | — | 1-431 | Cell division control |
| 5 | — | 1-167 | Xylogenesis - specific |
| 6 | — | 1-600 | 4-Coumarate-CoA Ligase (4CL) |
| 7 | — | 1-591 | Cellulose synthase |
| 8 | — | 1-480 | 3' end, cellulose synthase |
| 20 | — | 1-363 | 5' end, cellulose synthase |
| 9 | — | 1-259 | Leaf specific |
| 10 | — | 1-251 | Leaf specific |
| 11 | — | 1-248 | Leaf specific |
| 12 | — | 1-654 | O-methyl transferase |
| 13 | — | 1-396 | Root specific |
| 14 | — | 1-763 | Root specific |
| 22 | 63 | 1-406 | Pollen coat protein |
| 23 | — | 1-350 | Pollen allergen |
| 24 | — | 1-49 | Pollen allergen |
| 25 | 64 | 1-284 | Pollen allergen |
| 26 | 65 | 1-77 | Auxin-induced protein |
| 27 | — | 1-74 | Auxin-induced protein |
| 28 | 66 | 1-99 | Auxin-induced protein |
| 29 | — | 1-927 | Flower specific |
| 30 | — | 1-411 | Flower specific |
| 31 | — | 1-178 | Flower specific |
| 32 | — | 1-178 | Flower specific |
| 33 | — | 1-178 | Flower specific |
| 34 | 67 | 1-805 | Ubiquitin |
| 35 | 68 | 1-81 | Glyceraldehyde-3-phosphate dehydrogenase |
| 36 | 69 | 1-694 | Carbonic anhydrase |
| 37 | — | 1-648 | Isoflavone reductase |
| 38 | — | 1-288 | Isoflavone reductase |
| 39 | — | 1-382 | Glyceraldehyde-3-phosphate dehydrogenase |
| 40 | 70 | 1-343 | Bud specific |
| 41 | — | 1-313 | Xylem-specific |
| 42 | — | 1-713 | Xylem-specific |
| 43 | — | 1-28 | Xylem-specific |

TABLE 1-continued

| Polynucleotide SEQ ID NO: | Polypeptide SEQ ID NO: | 5' UTR | IDENTITY |
|---|---|---|---|
| 44 | — | 1-35 | Xylem-specific |
| 45 | 71 | 1-180 | Meristem-specific |
| 46 | 72 | 1-238 | Senescence-like protein |
| 47 | — | 1-91 | Senescence-like protein |
| 48 | — | 1-91 | Senescence-like protein |
| 49 | — | 1-809 | Pollen-specific |
| 50 | — | 1-428 | Pollen-specific |
| 51 | 73 | 1-55 | Pollen-specific |
| 52 | 74 | 1-575 | Pollen-specific |
| 53 | 75 | 1-35 | Pollen-specific |
| 54 | — | 1-335 | Nodulin homolog pollen specific |
| 55 | — | 1-336 | Nodulin homolog pollen specific |
| 56 | 76 | 1-157 | Sucrose synthase |
| 57 | 77 | 1-446 | Sucrose synthase |
| 58 | — | 1-326 | Sucrose synthase |
| 59 | — | 1-311 | Flower specific |
| 60 | 78 | 1-694 | O-methyl transferase |
| 61 | 79 | 1-112 | Elongation factor A |
| 62 | — | 1-420 | Elongation factor A |
| 81 | — | — | MIF homologue |
| 82 | — | — | MIF homologue |
| 83 | — | — | MIF homologue |
| 84 | — | — | MIF homologue |
| 85 | — | — | MIF homologue |
| 86 | 87 | 1-87 | MIF homologue |
| 88 | — | 1-1156 | Chalcone synthase |
| 89 | — | 1-2590 | Unknown flower specific |
| 90 | — | 1-1172 | Unknown flower specific |
| 91 | — | 1-446 | Sucrose synthase |
| 92 | — | 1-2119 | Unknown xylem specific |
| 93 | — | 1-2571 | Glyceraldehyde-3-Phosphate dehydrogenase |
| 94 | — | 1-1406 | Unknown pollen specific |
| 95 | — | 1-2546 | *Pinus radiata* male-specific protein (PrMALE1) |
| 96 | — | 1-4726 | *Pinus radiata* male-specific protein (PrMALE1) |
| 97 | — | 1-635 | UDP glucose glycosyltransferase |
| 98 | — | 1-468 | Elongation Factor A1 |
| 99 | — | 1-222 | Elongation Factor A1 |
| 100 | — | 1-410 | S-adenosylmethionine synthetase |
| 101 | — | 1-482 | S-adenosylmethionine synthetase |
| 102 | — | 1-230 | S-adenosylmethionine synthetase |
| 103 | — | 1-596 | UDP glucose 6 dehydrogenase |
| 104 | — | 1-653 | Hypothetical protein |
| 105 | — | 1-342 | Laccase 1 |
| 106 | — | 1-342 | Laccase 1 |
| 106 | — | 1-948 | Arabinogalactan-like 1 |
| 108 | — | I-362 | Arabinogalactan-like 2 |
| 109 | — | 1-326 | Arabinogaiactan like-2 |
| 110 | — | 1-296 | Root Receptor-like kinase |
| 111 | — | 1-723 | Root Receptor-Iike kinase |
| 112 | — | 1-1301 | *Pinus radiata* Lipid Transfer Protein 2 (PrLTP2) |
| 113 | — | 1-1668 | Caffeic acid O-methyltransferase |
| 114 | — | 1-850 | UDP glucose glycosyltransferase |
| 115 | — | 1-986 | UDP glucose 6 dehydrogenase |
| 116 | — | 1-947 | Laccase 1 |
| 117 | — | 1-1766 | Arabinogalactan like-1 |
| 118 | — | 1-1614 | Constans |
| 119 | — | 1-602 | Flowering Promoting Factor 1 (FPF1) |
| 120 | — | 1-901 | Agamous |

In one embodiment, the present invention provides polynucleotide sequences isolated from *Pinus radiata* and *Eucalyptus grandis* that encode a ubiquitin polypeptide. The full-length sequence of the ubiquitin polynucleotide isolated from *Pinus radiata* is provided in SEQ ID NO: 1, with the sequence of the promoter region including an intron being provided in SEQ ID NO: 2 and the sequence of the promoter region excluding the intron being provided in SEQ ID NO: 3. The sequence of the ubiquitin polynucleotide isolated from *Eucalyptus grandis* is provided in SEQ ID NO: 34. In a related embodiment the present invention provides isolated polypeptides encoded by the isolated polynucleotides of SEQ ID NO: 1 and 34, including polypeptides comprising the sequences of SEQ ID NO: 80 and 67.

The term "polynucleotide(s)," as used herein, means a single or double-stranded polymer of deoxyribonucleotide or ribonucleotide bases and includes DNA and corresponding RNA molecules, including HnRNA and mRNA molecules, both sense and anti-sense strands, and comprehends cDNA, genomic DNA and recombinant DNA, as well as wholly or partially synthesized polynucleotides. An HnRNA molecule contains introris and corresponds to a DNA molecule in a generally one-to-one manner. An mRNA molecule corresponds to an HnRNA and DNA molecule from which the introns have been excised. A polynucleotide may consist of an entire gene, or any portion thereof. Operable anti-sense polynucleotides may comprise a fragment of the corresponding polynucleotide, and the definition of "polynucleotide" therefore includes all such operable anti-sense fragments. Anti-sense polynucleotides and techniques involving anti-sense polynucleotides are well known in the art and are described, for example, in Robinson-Benion et al. "Antisense techniques," *Methods in Enzymol.* 254(23):363–375, 1995; and Kawasaki et al., in *Artific. Organs* 20(8):836–848, 1996.

All of the polynucleotides and polypeptides described herein are isolated and purified, as those terms are commonly used in the art. Preferably, the polypeptides and polynucleotides are at least about 80% pure, more preferably at least about 90% pure, and most preferably at least about 99% pure.

The definition of the terms "complement", "reverse complement" and "reverse sequence", as used herein, is best illustrated by the following example. For the sequence 5' AGGACC 3', the complement, reverse complement and reverse sequence are as follows:

| Complement | 3' TCCTGG 5' |
| Reverse complement | 3' GGTCCT 5' |
| Reverse sequence | 5' CCAGGA 3' |

Some of the polynucleotides of the present invention are "partial" sequences, in that they do not represent a full-length gene encoding a full-length polypeptide. Such partial sequences may be extended by analyzing and sequencing various DNA libraries using primers and/or probes and well known hybridization and/or PCR techniques. Partial sequences may be extended until an open reading frame encoding a polypeptide, a full-length polynucleotide and/or gene capable of expressing a polypeptide, or another useful portion of the genome is identified. Such extended sequences, including full-length polynucleotides and genes, are described as "corresponding to" a sequence identified as one of the sequences of SEQ ID NO: 1–14, 20, 22–62, 81–86 and 88–120, or a variant thereof, or a portion of one of the sequences of SEQ ID NO: 1–14, 20, 22–62, 81–86 and 88–120, or a variant thereof, when the extended polynucleotide comprises an identified sequence or its variant, or an identified contiguous portion (x-mer) of one of the sequences of SEQ ID NO: 1–14, 20, 22–62, 81–86 and 88–120, or a variant thereof. Such extended polynucleotides may have a length of from about 50 to about 4,000 nucleic acids or base pairs, and preferably have a length of less than about 4,000 nucleic acids or base pairs, more preferably yet a length of less than about 3,000 nucleic acids or base pairs, more preferably yet a length of less than about 2,000 nucleic acids or base pairs. Under some circumstances, extended polynucleotides of the present invention may have a length of less than about 1,800 nucleic acids or base pairs, preferably less than about 1,600 nucleic acids or base pairs, more preferably less than about 1,400 nucleic acids or base pairs, more preferably yet less than about 1,200 nucleic acids or base pairs, and most preferably less than about 1,000 nucleic acids or base pairs.

Similarly, RNA sequences, reverse sequences, complementary sequences, antisense sequences, and the like, corresponding to the polynucleotides of the present invention, may be routinely ascertained and obtained using the cDNA sequences identified as SEQ ID NO: 1–14, 20, 22–62, 81–86 and 88–120.

The polynucleotides identified as SEQ ID NO. 1–14, 20, 22–62, 81–86 and 88–120, may contain open reading frames ("ORFs") or partial open reading frames encoding polypeptides. Additionally, open reading frames encoding polypeptides may be identified in extended or full length sequences corresponding to the sequences set out as SEQ ID NO: 1–14, 20, 22–62, 81–86 and 88–120. Open reading frames may be identified using techniques that are well known in the art. These techniques include, for example, analysis for the location of known start and stop codons, most likely reading frame identification based on codon frequencies, etc. Suitable tools and software for ORF analysis include, for example, "GeneWise", available from The Sanger Center, Wellcome Trust Genome Campus, Hinxton, Cambridge, CB10 1SA, United Kingdom; "Diogenes", available from Computational Biology Centers, University of Minnesota, Academic Health Center, UMHG Box 43, Minneapolis Minn. 55455 and "GRAL", available from the Informatics Group, Oak Ridge National Laboratories, Oak Ridge, Tenn. Open reading frames and portions of open reading frames may be identified in the polynucleotides of the present invention. Once a partial open reading frame is identified, the polynucleotide may be extended in the area of the partial open reading frame using techniques that are well known in the art until the polynucleotide for the full open reading frame is identified. Thus, open reading frames encoding polypeptides may be identified using the polynucleotides of the present invention.

Once open reading frames are identified in the polynucleotides of the present invention, the open reading frames may be isolated and/or synthesized. Expressible genetic constructs comprising the open reading frames and suitable promoters, initiators, terminators, etc., which are well known in the art, may then be constructed. Such genetic constructs may be introduced into a host cell to express the polypeptide encoded by the open reading frame. Suitable host cells may include various prokaryotic and eukaryotic cells, including plant cells, mammalian cells, bacterial cells, algae and the like.

Polypeptides encoded by the polynucleotides of the present invention may be expressed and used in various assays to determine their biological activity. Such polypeptides may be used to raise antibodies, to isolate corresponding interacting proteins or other compounds, and to quantitatively determine levels of interacting proteins or other compounds.

The term "polypeptide", as used herein, encompasses amino acid chains of any length including full length proteins, wherein amino acid residues are linked by covalent peptide bonds. Polypeptides of the present invention may be isolated and purified natural products, or may be produced partially or wholly using recombinant techniques. The term "polypeptide encoded by a polynucleotide" as used herein, includes polypeptides encoded by a nucleotide sequence which includes the partial isolated DNA sequences of the present invention.

In a related aspect, polypeptides are provided that comprise at least a functional portion of a polypeptide having a sequence selected from the group consisting of sequences provided in SEQ ID NO: 63–80 and 87, and variants thereof. As used herein, the "functional portion" of a polypeptide is that portion which contains the active site essential for affecting the function of the polypeptide, for example, the portion of the molecule that is capable of binding one or more reactants. The active site may be made up of separate portions present on one or more polypeptide chains and will generally exhibit high binding affinity. Functional portions of a polypeptide may be identified by first preparing fragments of the polypeptide by either chemical or enzymatic digestion of the polypeptide, or by mutation analysis of the polynucleotide that encodes the polypeptide and subsequent expression of the resulting mutant polypeptides. The polypeptide fragments or mutant polypeptides are then tested to determine which portions retain biological activity, using, for example, the representative assays provided below. A functional portion comprising an active site may be made up of separate portions present on one or more polypeptide chains and generally exhibits high substrate specificity.

Portions and other variants of the inventive polypeptides may be generated by synthetic or recombinant means. Synthetic polypeptides having fewer than about 100 amino acids, and generally fewer than about 50 amino acids, may be generated using techniques well known to those of ordinary skill in the art. For example, such polypeptides may be synthesized using any of the commercially available solid-phase techniques, such as the Merrifield solid-phase synthesis method, wherein amino acids are sequentially added to a growing amino acid chain. (Merrifield, *J. Am. Chem. Soc.* 85: 2149–2154, 1963). Equipment for automated synthesis of polypeptides is commercially available from suppliers such as Perkin Elmer/Applied Biosystems, Inc. (Foster City, Calif.), and may be operated according to the manufacturer's instructions. Variants of a native polypeptide may be prepared using standard mutagenesis techniques, such as oligonucleotide-directed site-specific mutagensis (Kunkel, *Proc. Natl. Acad. Sci.* USA 82: 488–492, 1985). Sections of DNA sequences may also be removed using standard techniques to permit preparation of truncated polypeptides.

As used herein, the term "variant" comprehends nucleotide or amino acid sequences different from the specifically identified sequences, wherein one or more nucleotides or amino acid residues is deleted, substituted, or added. Variants may be naturally occurring allelic variants, or non-naturally occurring variants. Variant sequences (polynucleotide or polypeptide) preferably exhibit at least 50%, more preferably at least 75%, and most preferably at least 90% identity to a sequence of the present invention. The percentage identity is determined by aligning the two sequences to be compared as described below, determining the number of identical residues in the aligned portion, dividing that number by the total number of residues in the inventive (queried) sequence, and multiplying the result by 100.

Polynucleotide and polypeptide sequences may be aligned, and percentage of identical residues in a specified region may be determined against another polynucleotide and polypeptide sequences, using computer algorithms that are publicly available. Two exemplary algorithms for aligning and identifying the similarity of polynucleotide sequences are the BLASTN and FASTA algorithms. Polynucleotides may also be analyzed using the BLASTX algorithm, which compares the six-frame conceptual translation products of a nucleotide query sequence (both strands) against a protein sequence database. The similarity of polypeptide sequences may be examined using the BLASTP algorithm. The BLASTN algorithm version 2.0.4 [Feb. 24, 1998] and version 2.0.6 [Sep. 16, 1998], set to the default parameters described in the documentation and distributed with the algorithm, are preferred for use in the determination of polynucleotide variants according to the present invention. The BLASTP algorithm, is preferred for use in the determination of polypeptide variants according to the present invention. The use of the BLAST family of algorithms, including BLASTN, BLASTP, and BLASTX, is described in the publication of Altschul, et al., "Gapped BLAST and PSI-BLAST: a new generation of protein database search programs," *Nucleic Acids Res.* 25: 3389–3402, 1997.

The FASTA software package is available from the University of Virginia (University of Virginia, PO Box 9025, Charlottesville, Va. 22906-9025). Version 2.0u4, February 1996, set to the default parameters described in the documentation and distributed with the algorithm, may be used in the determination of variants according to the present invention. The use of the FASTA algorithm is described in Pearson and Lipman, "Improved Tools for Biological Sequence Analysis," *Proc. Natl. Acad. Sci.* USA 85: 2444–2448, 1988; and Pearson, "Rapid and Sensitive Sequence Comparison with FASTP and FASTA," *Methods in Enzymol.* 183: 63–98, 1990.

The following running parameters are preferred for determination of alignments and similarities using BLASTN that contribute to the E values and percentage identity for polynucleotide sequences: Unix running command: blastall -p blastn -d embldb -e 10 -G0 -E0 -r 1 -v 30 -b 30 -i, queryseq -o results; the parameters are: -p Program Name [String]; -d Database [String]; -e Expectation value (E) [Real]; -G Cost to open a gap (zero invokes default behavior) [Integer]; -E Cost to extend a gap (zero invokes default behavior) [Integer]; -r Reward for a nucleotide match (BLASTN only) [Integer]; -v Number of one-line descriptions (V) [Integer]; -b Number of alignments to show (B) [Integer]; -i Query File [File In]; and -o BLAST report Output File [File Out] Optional.

The following running parameters are preferred for determination of alignments and similarities using BLASTP that contribute to the E values and percentage identity of polypeptide sequences: blastall -p blastp -d swissprotdb -e 10 -G 0 -E 0 -v 30 -b 30 -i queryseq -o results; the parameters are: -p Program Name [String]; -d Database [String]; -e Expectation value (E) [Real]; -G Cost to open a gap (zero invokes default behavior) [Integer]; -E Cost to extend a gap (zero invokes default behavior) [Integer]; -v Number of one-line descriptions (v) [Integer]; -b Number of alignments to show (b) [Integer]; -I Query File [File In]; -o BLAST report Output File [File Out] Optional.

The "hits" to one or more database sequences by a queried sequence produced by BLASTN, FASTA, BLASTP or a similar algorithm, align and identify similar portions of sequences. The hits are arranged in order of the degree of similarity and the length of sequence overlap. Hits to a database sequence generally represent an overlap over only a fraction of the sequence length of the queried sequence.

The BLASTN, FASTA and BLASTP algorithms also produce "Expect" values for alignments. The Expect value (E) indicates the number of hits one can "expect" to see over a certain number of contiguous sequences by chance when searching a database of a certain size. The Expect value is used as a significance threshold for determining whether the hit to a database, such as the preferred EMBL database, indicates true similarity. For example, an E value of 0.1 assigned to a polynucleotide hit is interpreted as meaning that in a database of the size of the EMBL database, one might expect to see 0.1 matches over the aligned portion of the sequence with a similar score simply by chance. By this criterion, the aligned and matched portions of the polynucleotide sequences then have a probability of 90% of being the same. For sequences having an E value of 0.01 or less over aligned and matched portions, the probability of finding a match by chance in the EMBL database is 1% or less using the BLASTN or FASTA algorithm.

According to one embodiment, "variant" polynucleotides and polypeptides, with reference to each of the polynucleotides and polypeptides of the present invention, preferably comprise sequences having the same number or fewer nucleic or amino acids than each of the polynucleotides or polypeptides of the present invention and producing an E value of 0.01 or less when compared to the polynucleotide or polypeptide of the present invention. That is, a variant polynucleotide or polypeptide is any sequence that has at least a 99% probability of being the same as the polynucleotide or polypeptide of the present invention, measured as having an E value of 0.01 or less using the BLASTN, FASTA, or BLASTP algorithms set at parameters described above. According to a preferred embodiment, a variant polynucleotide is a sequence having the same number or fewer nucleic acids than a polynucleotide of the present invention that has at least a 99% probability of being the same as the polynucleotide of the present invention, measured as having an E value of 0.01 or less using the BLASTN or FASTA algorithms set at parameters described above. Similarly, according to a preferred embodiment, a variant polypeptide is a sequence having the same number or fewer amino acids than a polypeptide of the present invention that has at least a 99% probability of being the same as a polypeptide of the present invention, measured as having an E value of 0.01 or less using the BLASTP algorithm set at the parameters described above.

Alternatively, variant polynucleotides of the present invention hybridize to the polynucleotide sequences recited in SEQ ID NO: 1–14, 20, 22–62, 81–86 and 88–120, or complements, reverse sequences, or reverse complements of those sequences under stringent conditions. As used herein, "stringent conditions" refers to prewashing in a solution of 6×SSC, 0.2% SDS; hybridizing at 65° C., 6×SSC, 0.2% SDS overnight; followed by two washes of 30 minutes each in 1×SSC, 0.1% SDS at 65° C. and two washes of 30 minutes: each in 0.2×SSC, 0.1% SDS at 65° C.

The present invention also encompasses polynucleotides that differ from the disclosed sequences but that, as a consequence of the discrepancy of the genetic code, encode a polypeptide having similar activity to a polypeptide encoded by a polynucleotide of the present invention. Thus, polynucleotides comprising sequences that differ from the polynucleotide sequences recited in SEQ ID NO: 1–14, 20, 22–62, 81–86 and 88–120, or complements, reverse sequences, or reverse complements thereof, as a result of conservative substitutions are contemplated by and encompassed within the present invention. Additionally, polynucleotides comprising sequences that differ from the polynucleotide sequences recited in SEQ ID NO: 1–14, 20, 22–62, 81–86 and 88–120, or complements, reverse complements or reverse sequences thereof, as a result of deletions and/or insertions totaling less than 10% of the total sequence length are also contemplated by and encompassed within the present invention. Similarly, polypeptides comprising sequences that differ from the polypeptide sequences recited in SEQ ID NO: 63–80 and 87, as a result of amino acid substitutions, insertions, and/or deletions totaling less than 10% of the total sequence length are contemplated by an encompassed within the present invention. In certain embodiments, variants of the inventive polypeptides and polynucleotides possess biological activities that are the same or similar to those of the inventive polypeptides or polynucleotides. Such variant polynucleotides function as promoter sequences and are thus capable of modifying gene expression in a plant.

The polynucleotides of the present invention may be isolated from various libraries, or may be synthesized using techniques that are well known in the art. The polynucleotides may be synthesized, for example, using automated oligonucleotide synthesizers (e.g., Beckman Oligo 1000M DNA Synthesizer) to obtain polynucleotide segments of up to 50 or more nucleic acids. A plurality of such polynucleotide segments may then be ligated using standard DNA manipulation techniques that are well known in the art of molecular biology. One conventional and exemplary polynucleotide synthesis technique involves synthesis of a single stranded polynucleotide segment having, for example, 80 nucleic acids, and hybridizing that segment to a synthesized complementary 85 nucleic acid segment to produce a 5 nucleotide overhang. The next segment may then be synthesized in a similar fashion, with, a 5 nucleotide overhang on the opposite strand. The "sticky" ends ensure proper ligation when the two portions are hybridized. In this way, a complete polynucleotide of the present invention may be synthesized entirely in vitro.

Polynucleotides of the present invention also comprehend polynucleotides comprising at least a specified number of contiguous residues (x-mers) of any of the polynucleotides identified as SEQ ID NO: 1–14, 20, 22–62, 81–86 and 88–120, complements, reverse sequences, and reverse complements of such sequences, and their variants. Similarly, polypeptides of the present invention comprehend polypeptides comprising at least a specified number of contiguous residues (x-mers) of any of the polypeptides identified as SEQ ID NO: 63–80 and 87, and their variants. As used herein, the term "x-mer," with reference to a specific value of "x," refers to a sequence comprising at least a specified number ("x") of contiguous residues of any of the polynucleotides identified as SEQ ID NO: 1–14, 20, 22–62, 81–86 and 88–120, or the polypeptides identified as SEQ ID NO: 63–80 and 87. According to preferred embodiments, the value of x is preferably at least 20, more preferably at least 40, more preferably yet at least 60, and most preferably at least 80. Thus, polynucleotides and polypeptides of the present invention comprise a 20-mer, a 40-mer, a 60-mer, an 80-mer, a 100-mer, a 120-mer, a 150-mer, a 180-mer, a 220-mer, a 250-mer, a 300-mer, 400-mer, 500-mer or 600-mer of a polynucleotide or polypeptide identified as SEQ ID NO: 1–14, 20, 22–62, 81–86 and 88–120, and variants thereof.

As noted above, the inventive polynucleotide promoter sequences may be employed in genetic constructs to drive transcription and/or expression of a polynucleotide of interest. The polynucleotide of interest may be either endogenous or heterologous to an organism, for example a plant, to be transformed. The inventive genetic constructs may thus be employed to modulate levels of transcription and/or expression of a polynucleotide, for example gene, that is present in the wild-type plant, or may be employed to provide transcription and/or expression of a DNA sequence that is not found in the wild-type plant.

In certain embodiments, the polynucleotide of interest comprises an open reading frame that encodes a target polypeptide. The open reading frame is inserted in the genetic construct in either a sense or antisense orientation, such that transformation of a target plant with the genetic construct will lead to a change in the amount of polypeptide compared to the wild-type plant. Transformation with a genetic construct comprising an open reading frame in a sense orientation will generally result in over-expression of the selected polypeptide, while transformation with a genetic construct comprising an open reading frame in an antisense orientation will generally result in reduced expression of the selected polypeptide. A population of plants transformed with a genetic construct comprising an open reading frame in either a sense or antisense orientation may be screened for increased or reduced expression of the polypeptide in question using techniques well known to those of skill in the art, and plants having the desired phenotypes may thus be isolated.

Alternatively, expression of a target polypeptide may be inhibited by inserting a portion of the open reading frame, in either sense or antisense orientation, in the genetic construct. Such portions need not be full-length but preferably comprise at least 25 and more preferably at least 50 residues of the open reading frame. A much longer portion or even the full length DNA corresponding to the complete open reading frame may be employed. The portion of the open reading frame does not need to be precisely the same as the endogenous sequence, provided that there is sufficient sequence similarity to achieve inhibition of the target gene. Thus a sequence derived from one species may be used to inhibit expression of a gene in a different species.

In further embodiments, the inventive genetic constructs comprise a polynucleotide including an untranslated, or non-coding, region of a gene coding for a target polypeptide, or a polynucleotide complementary to such an untranslated region. Examples of untranslated regions which may be usefully employed in such constructs include introns and 5'-untranslated leader sequences. Transformation of a target plant with such a genetic construct may lead to a reduction in the amount of the polypeptide expressed in the plant by the process of cosuppression, in a manner similar to that discussed, for example, by Napoli et al., *Plant Cell* 2:279–290, 1990 and de Carvalho Niebel et al., *Plant Cell* 7:347–358, 1995.

Alternatively, regulation of polypeptide expression can be achieved by inserting appropriate sequences or subsequences (e.g. DNA or RNA) in ribozyme constructs (McIntyre and Manners, *Transgenic Res.* 5(4):257–262, 1996). Ribozymes are synthetic RNA molecules that comprise a hybridizing region complementary to two regions, each of which comprises at least 5 contiguous nucleotides in a mRNA molecule encoded by one of the inventive polynucleotides. Ribozymes possess highly specific endonuclease activity, which autocatalytically cleaves the mRNA.

The polynucleotide of interest, such as a coding sequence, is operably linked to a polynucleotide promoter sequence of the present invention such that a host cell is able to transcribe an RNA from the promoter sequence linked to the polynucleotide of interest. The polynucleotide promoter sequence is generally positioned at the 5' end of the polynucleotide to be transcribed. Use of a constitutive promoter, such as the *Pinus radiata* ubiquitin polynucleotide promoter sequence of SEQ ID NO: 2 and 3 or the *Eucalyptus grandis* ubiquitin polynucleotide promoter sequence contained within SEQ ID NO: 34, will affect transcription of the polynucleotide of interest in all parts of the transformed plant. Use of a tissue specific promoter, such as the leaf-specific promoters of SEQ ID NO: 9–11, the root-specific promoters of SEQ ID NO: 13 and 14, the flower-specific promoters of SEQ ID NO: 29–33, 59 and 89–90, the pollen-specific promoters of SEQ ID NO: 49–55 and 94, the bud-specific promoter of SEQ ID NO: 40 or the meristem-specific promoter of SEQ ID NO: 45, will result in production of the desired sense or antisense RNA only in the tissue of interest. Temporally regulated promoters, such as the xylogenesis-specific promoter of SEQ ID NO: 5, 41–44 and 92, can be employed to effect modulation of the rate of DNA transcription at a specific time during development of a transformed plant. With genetic constructs employing inducible gene promoter sequences, the rate of DNA transcription can be modulated by external stimuli, such as light, heat, anaerobic stress, alteration in nutrient conditions and the like.

The inventive genetic constructs further comprise a gene termination sequence which is located 3' to the polynucleotide of interest. A variety of gene termination sequences which may be usefully employed in the genetic constructs of the present invention are well known in the art. One example of such a gene termination sequence is the 3' end of the *Agrobacterium tumefaciens* nopaline synthase gene. The gene termination sequence may be endogenous to the target plant or may be exogenous, provided the promoter is functional in the target plant. For example, the termination sequence may be from other plant species, plant viruses, bacterial plasmids and the like.

The genetic constructs of the present invention may also contain a selection marker that is effective in cells of the target organism, such as a plant, to allow for the detection of transformed cells containing the inventive construct. Such markers, which are well known in the art, typically confer resistance to one or more toxins. One example of such a marker is the NPTII gene whose expression results in resistance to kanamycin or hygromycin, antibiotics which are usually toxic to plant cells at a moderate concentration (Rogers et al., in Weissbach A and H, eds. *Methods for Plant Molecular Biology*, Academic Press Inc.: San Diego, Calif., 1988). Transformed cells can thus be identified by their ability to grow in media containing the antibiotic in question. Alternatively, the presence of the desired construct in transformed cells can be determined by means of other techniques well known in the art, such as Southern and Western blots.

Techniques for operatively linking the components of the inventive genetic constructs are well known in the art and include the use of synthetic linkers containing one or more restriction endonuclease sites as described, for example, by Sambrook et al., (*Molecular cloning: a laboratory manual*, CSHL Press: Cold Spring Harbor, N.Y., 1989). The genetic construct of the present invention may be linked to a vector having at least one replication system, for example *E. coli*, whereby after each manipulation, the resulting construct can be cloned and sequenced and the correctness of the manipulation determined.

The genetic constructs of the present invention may be used to transform a variety of target organisms including, but not limited to, plants. Plants which may be transformed using the inventive constructs include both monocotyledonous angiosperms (e.g., grasses, corn, grains, oat, wheat and barley) and dicotyledonous angiosperms (e.g., Arabidopsis, tobacco, legumes, alfalfa, oaks, eucalyptus, maple), and Gymnosperms (e.g., Scots pine; see Aronen, *Finnish Forest Res. Papers*, Vol. 595, 1996), white spruce (Ellis et al., *Biotechnology* 11:84–89, 1993), and larch (Huang et al., *In Vitro Cell* 27:201–207, 1991). In a preferred embodiment, the inventive genetic constructs are employed to transform woody plants, herein defined as a tree or shrub whose stem lives for a number of years and increases in diameter each year by the addition of woody tissue. Preferably the target plant is selected from the group consisting of eucalyptus and pine species, most preferably from the group consisting of *Eucalyptus grandis* and *Pinus radiata*. Other species which may be usefully transformed with the genetic constructs of the present invention include, but are not limited to: pines such as *Pinus banksiana, Pinus brutia, Pinus caribaea, Pinus clausa, Pinus contorta, Pinus coulteri, Pinus echinata, Pinus eldarica, Pinus ellioti, Pinus jeffreyi, Pinus lambertiana, Pinus monticola, Pinus nigra, Pinus palustrus, Pinus pinaster, Pinus ponderosa, Pinus resinosa, Pinus rigida, Pinus serotina, Pinus strobus, Pinus sylvestris, Pinus taeda, Pinus virginiana*; other gymnosperrns, such as *Abies amabilis, Abies balsamea, Abies concolor, Abies grandis, Abies lasiocarpa, Abies magnifica, Abies procera, Chamaecyparis lawsoniona, Chamaecyparis nootkatensis, Chamaecyparis thyoides, Huniperus virginiana, Larix decidua, Larix laricina, Larix leptolepis, Larix occidentalis, Larix siberica, Libocedrus decurrens, Picea abies, Picea engelmanni, Picea glauca, Picea mariana, Picea punggens, Picea rubens, Picea sitchensis, Pseudotsuga menziesii, Sequoia gigantea, Sequoia sempervirens, Taxodium distichum, Tsuga canadensis, Tsuga heterophylla, Tsuga mertensiana, Thuja occidentalis, Thuja plicata*; and Eucalypts, such as *Eucalyptus alba, Eucalyptus bancroftii, Eucalyptus botyroides, Eucalyptus bridgesiana, Eucalyptus calophylla, Eucalyptus camaldulensis, Eucalyptus citriodora, Eucalyptus cladocalyx, Eucalyptus coccifera, Eucalyptus curtisii, Eucalyptus dalrympleana, Eucalyptus deglupta, Eucalyptus delagatensis, Eucalyptus diversicolor, Eucalyptus dunnii, Eucalyptus ficifolia, Eucalyptus globulus, Eucalyptus gomphocephala, Eucalyptus gunnii, Eucalyptus henryi, Eucalyptus laevopinea, Eucalyptus macarthurii, Eucalyptus macrorhyncha, Eucalyptus maculata, Eucalyptus marginata, Eucalyptus megacarpa, Eucalyptus melliodora, Eucalyptus nicholii, Eucalyptus nitens, Eucalyptus nova-anglica, Eucalyptus obliqua, Eucalyptus obtusiflora, Eucalyptus oreades, Eucalyptus pauciflora, Eucalyptus polybractea, Eucalyptus regnans, Eucalyptus resinifera, Eucalyptus robusta, Eucalyptus rudis, Eucalyptus saligna, Eucalyptus sideroxylon, Eucalyptus stuartiana, Eucalyptus tereticornis, Eucalyptus torelliana, Eucalyptus urnigera, Eucalyptus urophylla, Eucalyptus viminalis, Eucalyptus viridis, Eucalyptus wandoo* and *Eucalyptus youmanni*; and hybrids of any of these species.

Techniques for stably incorporating genetic constructs into the genome of target plants are well known in the art and include *Agrobacterium tumefaciens* mediated introduction, electroporation, protoplast fusion, injection into reproductive organs, injection into immature embryos, high velocity projectile introduction and the like. The choice of technique will depend upon the target plant to be transformed. For example, dicotyledonous plants and certain monocots and gymnosperms may be transformed by Agrobacterium Ti plasmid technology, as described, for example by Bevan, *Nucleic Acids Res.* 12:8711–8721, 1984. Targets for the introduction of the genetic constructs of the present invention include tissues, such as leaf tissue, dissociated cells, protoplasts, seeds, embryos, meristematic regions; cotyledons, hypocotyls, and the like. The preferred method for transforming eucalyptus and pine is a biolistic method using pollen (see, for exanple, Aronen, *Finnish Forest Res. Papers*, Vol. 595, 53pp, 1996) or easily regenerable embryonic tissues.

Once the cells are transformed, cells having the inventive genetic construct incorporated in their genome may be selected by means of a marker, such as the kanamycin resistance marker discussed above. Transgenic cells may then be cultured in an appropriate medium to regenerate whole plants, using techniques well known in the art. In the case of protoplasts, the cell wall is allowed to reform under appropriate osmotic conditions. In the case of seeds or embryos, an appropriate germination or callus initiation medium is employed. For explants, an appropriate regeneration medium is used. Regeneration of plants is well established for many species. For a review of regeneration of forest trees see Dunstan et al., "Somatic embryogenesis in woody plants," in Thorpe T A, ed., *In Vitro Embryogenesis of Plants* (*Current Plant Science and Biotechnology in Agriculture* Vol. 20), Chapter 12, pp. 471–540, 1995. Specific protocols for the regeneration of spruce are discussed by Roberts et al., "Somatic embryogenesis of spruce," in Redenbaugh K, ed., *Synseed: applications of synthetic seed to crop improvement*, CRC Press: Chapter 23, pp. 427–449, 1993). Transformed plants having the desired phenotype may be selected using techniques well known in the art. The resulting transformed plants may be reproduced sexually or asexually, using methods well known in the art, to give successive generations of transgenic plants.

As discussed above, the production of RNA in target cells can be controlled by choice of the promoter sequence, or by selecting the number of functional copies or the site of integration of the polynucleotides incorporated into the genome of the target host. A target organism may be transformed with more than one genetic construct of the present invention, thereby modulating the activity of more than gene. Similarly, a genetic construct may be assembled containing more than one open reading frame coding for a polypeptide of interest or more than one untranslated region of a gene coding for such a polypeptide.

The isolated polynucleotides of the present invention also have utility in genome mapping, in physical mapping, and in positional cloning of genes. As detailed below, the polynucleotide sequences identified as SEQ ID NO: 1–14, 20, 22–62, 81–86 and 88–120, and their variants, may be used to design oligonucleotide probes and primers. Oligonucleotide probes designed using the polynucleotides of the present invention may be used to detect the presence and examine the expression patterns of genes in any organism having sufficiently similar DNA and RNA sequences in their cells using techniques that are well known in the art, such as slot blot DNA hybridization techniques. Oligonucleotide primers designed using the polynucleotides of the present invention may be used for PCR amplifications. Oligonucleotide probes and primers designed using the polynucleotides of the present invention may also be used in connection with various microarray technologies, including the microarray technology of Synteni (Palo Alto, Calif.).

As used herein, the term "oligonucleotide" refers to a relatively short segment of a polynucleotide sequence, generally comprising between 6 and 60 nucleotides, and comprehends both probes for use in hybridization assays and primers for use in the amplification of DNA by polymerase chain reaction.

An oligonucleotide probe or primer is described as "corresponding to" a polynucleotide of the present invention, including one of the sequences set out as SEQ ID NO: 1–14, 20, 22–62, 81–86 and 88–120, or a variant, if the oligonucleotide probe or primer, or its complement, is contained within one of the sequences set out as SEQ ID NO: 1–14, 20, 22–62, 81–86 and 88–120, or a variant of one of the specified sequences. Oligonucleotide probes and primers of the present invention are substantially complementary to a polynucleotide disclosed herein.

Two single stranded sequences are said to be substantially complementary when the nucleotides of one strand, optimally aligned and compared, with the appropriate nucleotide insertions and/or deletions, pair with at least 80%, preferably at least 90% to 95% and more preferably at least 98% to 100% of the nucleotides of the other strand. Alternatively, substantial complementarity exists when a first DNA strand will selectively hybridize to a second DNA strand under stringent hybridization conditions. Stringent hybridization conditions for determining complementarity include salt conditions of less than about 1 M, more usually less than about 500 mM, and preferably less than about 200 mM. Hybridization temperatures can be as low as 5° C., but are generally greater than about 22° C., more preferably greater than about 30° C., and most preferably greater than about 37° C. Longer DNA fragments may require higher hybridization temperatures for specific hybridization. Since the stringency of hybridization may be affected by other factors such as probe composition, presence of organic solvents and extent of base mismatching, the combination of parameters is more important than the absolute measure of any one alone.

In specific embodiments, the oligonucleotide probes and/or primers comprise at least about 6 contiguous residues, more preferably at least about 10 contiguous residues, and most preferably at least about 20 contiguous residues complementary to a polynucleotide sequence of the present invention. Probes and primers of the present invention may be from about 8 to 100 base pairs in length or, preferably from about 10 to 50 base pairs in length or, more preferably from about 15 to 40 base pairs in length. The probes can be easily selected using procedures well known in the art, taking into account DNA-DNA hybridization stringencies, annealing and melting temperatures, and potential for formation of loops and other factors, which are well known in the art. Preferred techniques for designing PCR primers are disclosed in Dieffenbach, C W and Dyksler, G S. PCR *Primer: a laboratory manual*, CSHL Press: Cold Spring Harbor, N.Y., 1995. A software program suitable for designing probes, and especially for designing PCR primers, is available from Premier Biosoft International, 3786 Corina Way, Palo Alto, Calif. 94303-4504.

A plurality of oligonucleotide probes or primers corresponding to a polynucleotide of the present invention may be provided in a kit form. Such kits generally comprise multiple DNA or oligonucleotide probes, each probe being specific for a polynucleotide sequence. Kits of the present invention may comprise one or more probes or primers corresponding to a polynucleotide of the present invention, including a polynucleotide sequence identified in SEQ ID NO: 1–14, 20, 22–62, 81–86 and 88–120.

In one embodiment useful for high-throughput assays, the oligonucleotide probe kits of the present invention comprise multiple probes in an array format, wherein each probe is immobilized at a predefined, spatially addressable location on the surface of a solid substrate. Array formats which may be usefully employed in the present invention are disclosed, for example, in U.S. Pat. Nos. 5,412,087 and 5,545,451; and PCT Publication No. WO 95/00450, the disclosures of which are hereby incorporated by reference.

The polynucleotides of the present invention may also be used to tag or identify an organism or reproductive material therefrom. Such tagging may be accomplished, for example, by stably introducing a non-disruptive non-functional heterologous polynucleotide identifier into an organism, the polynucleotide comprising one of the polynucleotides of the present invention.

The following examples are offered by way of illustration and not by way of limitation.

EXAMPLE 1

Isolation and Characterization of a Ubiquitin Gene Promoter from *Pinus radiata*

*Pinus radiata* cDNA expression libraries were constructed and screened as follows. mRNA was extracted from plant tissue using the protocol of Chang et al., *Plant Molecular Biology Reporter* 11:113–116, 1993 with minor modifications. Specifically, samples were dissolved in CPC-RNAXB (100 mM Tris-Cl, pH 8,0; 25 mM EDTA; 2.0 M NaCl; 2% CTAB; 2% PVP and 0.05% Spernidine*3HCl) and extracted with chloroform:isoamyl alcohol, 24:1. mRNA was precipitated with ethanol and the total RNA preparate was purified using a Poly(A) Quik mRNA Isolation Kit (Stratagene, La Jolla, Calif.). A cDNA expression library was constructed from the purified mRNA by reverse transcriptase synthesis followed by insertion of the resulting cDNA clones in Lambda ZAP using a ZAP Express cDNA Synthesis Kit (Stratagene), according to the manufacturer's protocol. The resulting cDNAs were packaged using a Gigapack II Packaging Extract (Stratagene) employing 1 µl of sample DNA from the 5 µl ligation mix. Mass excision of the library was done using XL1-Blue MRF' cells and XLOLR cells (Stratagene) with ExAssist helper phage (Stratagene). The excised phagemids were diluted with NZY broth (Gibco BRL, Gaithersburg, Md.) and plated out onto LB-kanamycin agar plates containing X-gal and isopropylthio-beta-galactoside (IPTG).

Of the colonies plated and picked for DNA miniprep, 99% contained an insert suitable for sequencing. Positive colonies were cultured in NZY broth with kanamycin and cDNA was purified by means of alkaline lysis and polyethylene glycol (PEG) precipitation. Agarose gel at 1% was used to screen sequencing templates for chromosomal contamination. Dye primer sequences were prepared using a Turbo Catalyst 800 machine (Perkin Elmer/Applied Biosystems Division, Foster City, Calif.) according to the manufacturer's protocol.

DNA sequence for positive clones was obtained using a Perkin Elmer/Applied Biosystems Division Prism 377 sequencer. cDNA clones were sequenced first from the 5' end and, in some cases, also from the 3' end. For some clones, internal sequence was obtained using subcloned fragments. Subcloning was performed using standard procedures of restriction mapping and subcloning to pBluescript II SK+vector.

As described below, one of the most abundant sequences identified was a ubiquitin gene, hereinafter referred to as the "Super-Ubiquitin" gene.

Isolation of cDNA Clones Containing the Ubiquitin Gene

Sequences of cDNA clones with homology to the ubiquitin gene were obtained from high-throughput cDNA sequencing as described above. Sequences from several independent clones were assembled in a contig and a consensus sequence was generated from overlapping clones. The determined nucleotide sequence of the isolated Super Ubiquitin clone, comprising the promoter region (including an intron), coding region and 3' untranslated region (UTR) is provided in SEQ ID NO: 1. The 5' UTR is represented by residues 1 to 2064, the intron by residues 1196 to 2033, and the coding region of the gene, which contains three direct repeats, by residues 2065 to 2751. The 3' UTR is 328 residues long (residues 2755 to 3083). The nucleotide sequence of the Super Ubiquitin promoter region only, including the intron, is given in SEQ ID NO: 2. The nucleotide sequence of the Super Ubiquitin promoter region only, excluding the intron, is given in SEQ ID NO: 3. The predicted amino acid sequence for the *Pinus radiata* Super Ubiquitin is provided in SEQ ID NO: 80.

Ubiquitin proteins function as part of a protein degradation pathway, in which they covalently attach to proteins, thereby targeting them for degradation (for a review, see Belknap and Garbarino, *Trends in Plant Sciences* 1:331–335, 1996). The protein is produced from a precursor polypeptide, encoded by a single mRNA. The Super Ubiquitin mRNA contains three copies of the ubiquitin monomer.

Cloning of the Super Ubiquitin Promoter

Fragments of the Super Ubiquitin promoter were cloned by two different PCR-based approaches.

Method 1: Long Distance Gene Walking PCR

Using "Long Distance Gene Walking" PCR (Min and Powell, *Biotechniques* 24:398–400, 1998), a 2 kb fragment was obtained that contained the entire coding region of the ubiquitin gene, a 900 bp intron in the 5' UTR and approximately 100 bp of the promoter.

To generate this fragment, 2 nested primers were designed from the 3' UTR of the Super Ubiquitin cDNA sequence isolated from pine. Generally, the 5' UTR is used for primer design to amplify upstream sequence. However, the available 5' UTR of Super Ubiquitin was very short, and two initial primers derived from this region failed to amplify any fragments. Therefore, the primers of SEQ ID NO: 15 and 16 were designed from the 3' UTR.

The method involved an initial, linear PCR step with pine genomic DNA as template using the primer of SEQ ID NO: 15, and subsequent C-tailing of the single stranded DNA product using terminal transferase. The second PCR-step used these fragments as template for amplification with the primer of SEQ ID NO: 16 and primer AP of SEQ ID NO: 17. The AP primer was designed to bind to the polyC tail generated by the terminal transferase. Both primers (SEQ ID NO: 16 and 17) contained a 5'-NotI restriction site for the cloning of products into the NotI site of a suitable vector. The final PCR product contained fragments of different sizes. These fragments were separated by electrophoresis and the largest were purified from the gel, digested with restriction endonuclease NotI and cloned in the NotI site of expression vector pBK-CMV (Stratagene, La Jolla, Calif.). The largest of these clones contained the complete coding region of the gene. (no introns were found in the coding sequence) and a 5' UTR which contained a 900 bp intron.

Method 2: "Genome Walker" Kit

The Super Ubiquitin gene promoter was cloned using a "Genome Walker" kit (Clontech, Palo Alto, Calif.). This is also a PCR-based method, which requires 2 PCR primers to be constructed, one of which must be gene-specific. Although the ubiquitin coding region is highly conserved, the 5' UTR from different ubiquitin genes is not conserved and could therefore be used to design a gene-specific primer. A 2.2 kb fragment was amplified and subcloned in pGEM-T-easy (Promega, Madison, Wis.). Analysis by PCR and DNA sequencing showed that the clone contained 5' UTR sequence of the Super Ubiquitin gene, including the 900 bp intron and approximately 1 kb of putative promoter region. An intron in the 5' UTR is a common feature of plant polyubiquitin genes and may be involved in determining gene expression levels.

The gene specific primers used for these PCR reactions are provided in SEQ ID NO: 18 and 19.

Expression of Super Ubiquitin

Using primers derived from the gene-specific 5' and 3' UTR sequences, expression levels of Super Ubiquitin in different plant tissues was examined by means of RT-PCR. Super Ubiquitin was found to be expressed in all plant tissues examined, including branch phloem and xylem, feeder roots, fertilized cones, needles, one year old cones, pollen sacs, pollinated cones, root xylem, shoot buds, structural roots, trunk phloem and trunk. Expression of Super Ubiquitin in plant tissues was also demonstrated in a Northern blot assay using a PCR probe prepared from the 5' UTR.

Functional Analysis of the Super Ubiquitin Promoter

To test the function of the Super Ubiquitin promoter in plants, *Arabidopsis thaliana* was transformed with constructs containing the reporter gene for Green Fluorescent Protein (GFP) operably linked to either the Super Ubiquitin promoter of SEQ ID NO: 2 or SEQ ID NO: 3 (i.e., either with or without the infron). Constructs lacking a promoter were used as a negative control, with a plant T-DNA vector carrying a CaMV 35S promoter cloned in front of GFP being used as a positive control. The constructs were introduced into Arabidopsis via Agrobacterium-mediated transformation.

All the plant culture media were according to the protocol of Valvekens and Van Montagu, *Proc. Natl. Acad. Sci.* USA 85:5536–5540, 1988 with minor modifications. For root transformation, sterilized seeds were placed in a line on the surface of germination medium, the plates were placed on their sides to facilitate root harvesting, and the seeds were grown for two weeks at 24° C. with a 16 h photoperiod.

Expression of the constructs was measured by determining expression levels of the reporter gene for Green Fluorescent Protein (GFP). Preliminary GFP expression (transient) was detected in early transgenic roots during T-DNA transfer. Transgenic roots that developed green callus, growing on shoot-inducing medium containing 50 µg/ml Kanamycin and 100 µg/ml Timentin, were further tested for GFP expression. After several weeks of stringent selection on Kanamycin medium, several independent transgenic Arabidopsis lines were engineered and tested for GFP expression.

Expression was seen both with the Super Ubiquitin promoter including intron and the Super Ubiquitin promoter without the intron. However, preliminary results indicated that the levels of expression obtained with the Super Ubiquitin intron-less promoter construct were significantly higher than those seen with the promoter including intron, suggesting that the intron may contain a repressor. The sequence of the intron is provided in SEQ ID NO: 21.

EXAMPLE 2

Isolation of a CDC Promoter from *Pinus radiata*

Plant EST sequences homologous to the Cell Division Control (CDC) protein gene were isolated from a *Pinus radiata* cDNA expression library as described in Example 1. Using the "Genome Walker" protocol described above and gene specific primers designed from these plant EST sequences, 5' UTR sequence containing the putative promoter of the *P. radiata* CDC gene was isolated from genomic DNA. The determined nucleotide sequence is given in SEQ ID NO: 4.

EXAMPLE 3

Isolation of a Xylogenesis-Specific Promoter from *Pinus radiata*

Plant EST sequences specific for plant xylogenesis were isolated from *Pinus radiata* cDNA expression libraries prepared from xylem, essentially as described in Example 1. Using the "Genome Walker" protocol described above and gene specific primers designed from these plant EST sequences, sequences containing putative *Pinus radiata* xylogenesis-specific promoters were isolated from genomic DNA. The determined nucleotide sequences are provided in SEQ ID NO: 5 and 41–44. An extended cDNA sequence for the clone of SEQ ID NO: 41–44 is provided in SEQ ID NO: 92.

EXAMPLE 4

Isolation of a 4-Coumarate-CoA Ligase Promoter from *Pinus radiata*

Plant EST sequences homologous to the 4-Coumarate-CoA Ligase (4CL) gene were isolated from a *Pinus radiata* cDNA expression library as described in Example 1. Using the "Genome Walker" protocol described above and gene specific primers designed from these plant EST sequences, sequences containing the putative promoter of the *P. radiata* 4CL gene was isolated from genomic DNA. The determined nucleotide'sequence is given in SEQ ID NO: 6.

Genetic constructs comprising the reporter gene for Green Fluorescent Protein (GFP) or GUS reporter genes operably linked to the promoter of SEQ ID NO: 6 were prepared and used to transform *Arabidopsis thaliana* plants.

EXAMPLE 5

Isolation of a Cellulose Synthase Promoter from *Eucalyptus grandis*

Plant EST sequences homologous to the cellulose synthase gene were isolated from a *Eucalyptus grandis* cDNA expression library essentially as described in Example 1. Using the "Genome Walker" protocol described above and gene specific primers designed from these plant EST sequences, 5' UTR sequences containing the putative promoter of the *E. grandis* cellulose synthase gene were isolated from genomic DNA. Independent PCR experiments using different DNA bands as templates yielded two sequences which contained a number of base differences. One band was 750 bp in length and the nucleotide sequence of this band is given in SEQ ID NO: 7. The other band was 3 kb in length. The sequence of the 3' end of this band corresponded to the sequence given in SEQ ID NO: 7, with a number of base pair differences. The sequence of this 3' end is given in SEQ ID NO: 8. The sequence of the 5' end of this band is given in SEQ ID NO: 20.

EXAMPLE 6

Isolation of a Leaf-Specific Promoter from *Eucalyptus grandis*

Plant EST sequences specific for leaf were isolated from *Eucalyptus grandis* cDNA expression libraries prepared from leaf tissue, essentially as described in Example 1. Using the "Genome Walker" protocol described above and gene specific primers designed from these plant EST sequences, 5' UTR sequence containing a leaf-specific promoter of a novel *E. grandis* gene (of unknown function) was isolated from genomic DNA. Independent PCR experiments using different DNA bands as templates yielded three sequences which contained a number of base differences and deletions. The determined nucleotide sequences of the three PCR fragments are given in SEQ ID NO: 9–11.

EXAMPLE 7

Isolation of an O-Methyl Transferase Promoter from *Eucalyptus grandis*

Plant EST sequences homologous to an O-methyl transferase (OMT) gene were isolated from a *Eucalyptus grandis* cDNA expression library essentially as described in Example 1. Using the "Genome Walker" protocol described above and gene specific primers designed from these plant EST sequences, 5'UTR sequences containing the putative promoter of the *E. grandis* OMT gene was isolated from genomic DNA. The determined nucleotide sequence is given in SEQ ID NO: 12. This promoter sequence was extended by further sequencing. The extended cDNA sequences are given in SEQ ID NO: 60 and 113.

Genetic constructs comprising the reporter gene for Green Fluorescent Protein (GFP) operably linked to the promoter of SEQ ID NO: 12 were prepared and used to transform *Arabidopsis thaliana*.

EXAMPLE 8

Isolation of Root-Specific Promoters from *Pinus radiata*

Plant EST sequences homologous to the root-specific receptor-like kinase gene were isolated from a *Pinus radiata* cDNA expression library as described in Example 1. Using the "Genome Walker" protocol described above and gene specific primers designed from these plant EST sequences, 5'UTR sequence containing a putative *P. radiata* root-specific promoter was isolated from genomic DNA. Two independent PCR experiments yielded sequences that contained a number of base differences. The determined nucleotide sequences from the two experiments are given in SEQ ID NO: 13, 14, 110 and 111.

EXAMPLE 9

Isolation of an EF1-alpha Promoter from *Eucalyptus Grandis*

Plant EST sequences homologous to the Eucalyptus Elongation Factor-alpha (EF1-alpha) gene were isolated from a *Eucalyptus grandis* cDNA expression library and used to screen a *Eucalyptus grandis* genomic DNA library as follows.

The *Eucalyptus grandis* genomic DNA library was constructed using genomic DNA extracted from *Eucalyptus nitens x grandis* plant tissue, according to the protocol of Doyle and Doyle, Focus 12:13–15, 1990, with minor modifications. Specifically, plant tissue was ground under liquid nitrogen and dissolved in 2×CTAB extraction buffer (2% CTAB, hexadecyltrimethylammonium bromide; 1.4 M NaCl, 20 mM EDTA pH 8.0, 100 mM Tris.HCl pH 8.0, 1% polyvinylpyrollidone). After extraction with chloroform:isoamylalcohol (24:1), 10% CTAB was added to the aqueous layer and the chloroform:isoamylalcohol extraction repeated. Genomic DNA was precipitated with isopropanol.

The resulting DNA was digested with restriction endonuclease Sau3Al following standard procedures, extracted once with phenol:chloroform:isoamylalcohol (25:24:1) and ethanol precipitated. The digested fragments were separated on a sucrose density gradient using ultracentrifugation. Fractions containing fragments of 9–23 kb were pooled and ethanol precipitated. The resulting fragments were cloned into the lambda DASH II/BamHI vector (Stratagene, La Jolla, Calif.) following the manufacturer's protocol and packaged using a Gigapack II Packaging Extract (Stratagene). The library was amplified once.

The library was screened with radio-labeled EST fragments isolated from a *Eucalyptus grandis* library (as, described in Example 1), that showed homology to the Eucalyptus EF1-alpha gene. Phage lysates were prepared from positive plaques and genomic DNA was extracted.

From this genomic DNA, the 5'UTR region containing the putative promoter of the Eucalyptus EF1-alpha gene was obtained using the ELONGASE Amplification System (Gibco BRL). A 10 kb fragment was amplified and restriction mapped. The putative promoter region of the Eucalyptus elongation factor A (EF1-alpha) gene was identified on a 4 kb fragment, which was subcloned into a pUC19 vector (Gibco BRL) containing an engineered NotI-site. The determined genomic DNA sequences of the isolated fragment containing the promoter region are provided in SEQ ID NO: 61 and 62, with the predicted amino acid encoded by SEQ ID NO: 61 being provided in SEQ ID NO: 79.

EXAMPLE 10

Isolation of Flower-Specific Promoters from *Eucalyptus grandis*

Plant EST sequences specific for flower-derived tissue were isolated from *Eucalyptus grandis* cDNA expression libraries prepared from flower tissue, essentially as described in Example 1. Using the "Genome Walker" protocol described above and gene specific primers designed from these plant EST sequences, several sequences, each containing a putative *Eucalyptus grandis* flower-specific promoter, were isolated from genomic DNA. The determined nucleotide sequences are given in SEQ ID NO: 29–33 and 59. An extended cDNA sequence of the clone of SEQ ID NO: 30–33 is provided in SEQ ID NO: 89. An extended cDNA sequence of the clone of SEQ ID NO: 29 is provided in SEQ ID NO: 90.

EXAMPLE 11

Isolation of Pollen-Specific Promoters from *Eucalyptus grandis* and *Pinus radiata*

Plant EST sequences specific for pollen were isolated from *Eucalyptus grandis* and *Pinus radiata* cDNA expression libraries prepared from pollen, essentially as described in Example 1. Using the "Genome Walker" protocol described above and gene specific primers designed from these plant EST sequences, several sequences, each containing a putative pollen-specific promoter, were isolated from genomic DNA. The determined nucleotide sequences isolated from *Pinus radiata* are given in SEQ ID NO: 49–53, with the predicted amino acid sequences encoded by SEQ ID NO: 51–53 being provided in SEQ ID NO: 73–75, respectively. An extended cDNA sequence for the clone of SEQ ID NO: 49 is provided in SEQ ID NO: 94.

EXAMPLE 12

Isolation of Bud-Specific and Meristem-Specific Promoter from *Pinus radiata*

Plant EST sequences specific for bud and meristem were isolated from *Pinus radiata* cDNA expression libraries prepared from bud and meristem, essentially as described in Example 1. Using the "Genome Walker" protocol described above and gene specific primers designed from these plant EST sequences, two sequences, one containing a putative bud-specific promoter and the other containing a putative meristem-specific promoter, were isolated from genomic DNA. The determined nucleotide sequences for these two promoters are given in SEQ ID NO: 40 and 45, respectively. The predicted amino acid sequences encoded by the DNA sequences of SEQ ID NO: 40 and 45 are provided in SEQ ID NO: 70 and 71, respectively.

EXAMPLE 13

Isolation of Promoters from *Eucalyptus grandis*

Plant EST sequences showing some homology to various known genes were isolated from *Eucalyptus grandis* cDNA expression libraries essentially as described in Example 1. Using the "Genome Walker" protocol described above and gene specific primers designed from these plant EST sequences, sequences containing the putative promoters for the following *E. grandis* genes were isolated from genomic DNA: auxin induced protein (SEQ ID NO: 26–28); carbonic anhydrase (SEQ ID NO: 36); isoflavone reductase (SEQ ID NO: 37 and 38); pollen allergen (SEQ ID NO: 23–25); pollen coat protein (SEQ ID NO: 22), sucrose synthase (SEQ ID NO: 56–58); ubiquitin (SEQ ID NO: 34); glyceraldehyde-3-phosphate dehydrogenase (SEQ ID NO: 35 and 39); O-methyl transferase (OMT; SEQ ID NO: 60); macrophage migration inhibition factor from mammals (MIF; SEQ ID NO: 81–86); UDP glucose 6-dehydrogenase (SEQ ID NO: 103); laccase 1 (SEQ ID: NO: 105, 106 and 116); arabinogalactan-like 1 (SEQ ID NO: 107); arabinogalactan-like 2 (SEQ. ID NO: 108, 109), a hypothetical protein (SEQ ID NO: 104), constans (SEQ ID NO: 118) and Flowering Promoting Factor 1 (FPF1; SEQ ID NO: 119). The predicted amino acid sequences encoded by the DNA sequences of SEQ ID NO: 22, 25, 26, 28, 34, 35, 36, 56, 57, 60 and 86 are provided in SEQ ID NO: 63, 64, 65, 66, 67, 68, 69, 76, 77, 78 and 87 respectively. Extended cDNA sequences for the clones of SEQ ID NO: 58, 35, 60, 103, 106 and 107 are provided in SEQ ID NO: 91, 93, 113, 115–117 respectively.

EXAMPLE 14

Isolation of Promoters from *Pinus radiata*

Plant EST sequences showing some homology to various known genes were isolated from *Pinus radiata* cDNA expression libraries essentially as described in Example 1. Using the "Genome Walker" protocol described above and gene specific primers designed from these plant EST sequences, sequences containing the putative promoters for the following *Pinus radiata* genes were isolated from genomic DNA: senescence-like protein (SEQ ID NO: 46–48); nodulin homolog pollen specific (SEQ ID NO: 54 and 55); chalcone synthase (SEQ ID NO: 88); PrMALE1 (SEQ ID NO: 95, 96); UDP glucose glycosyltransferase (SEQ ID NO: 97); elogation factor 1 alpha (SEQ ID NO: 98, 99); S-adenosylmethionine synthase (SEQ ID NO: 100–102); *Pinus radiata* lipid transfer protein 2 (PrLTP2; SEQ ID NO: 112) and *Pinus radiata* agamous protein (SEQ ID NO: 120). The predicted amino acid sequence encoded by the sequence of SEQ ID NO: 46 is provided in SEQ ID NO: 72. An extended cDNA sequence for the clone of SEQ ID NO: 97 is provided in SEQ ID NO: 114.

EXAMPLE 15

Polynucleotide and Amino Acid Analysis

The determined cDNA sequences described above were compared to and aligned with known sequences in the EMBL database (as updated to April 2000). Specifically, the polynucleotides identified in SEQ ID NO: 22–62 and 88–120 were compared to polynucleotides in the EMBL database using the BLASTN algorithm Version 2.0.6 [Sep. 16, 1998] set to the following running parameters: Unix running command: blastall -p blastn -d embldb -e 10 -G0 -E0 -r1 -v30 -b3.0 -i queryseq -o results. Multiple alignments of redundant sequences were used to build up reliable consensus sequences. Based on similarity to known sequences from other plant or non-plant species, the isolated polynucleotides of the present invention identified as SEQ ID NO: 22–62 and 88–120 were putatively identified as having the functions shown in Table 1, above.

The cDNA sequences of SEQ ID NO: 1–22, 23, 25–42, 45–49, 57–59, 62, 88–99, 101–112 and 114–120 were determined to have less than 40% identity to sequences in the EMBL database using the computer algorithm BLASTN, as described above. The cDNA sequences of SEQ ID NO: 56 and 113 was determined to have less than 60% identity to sequences in the EMBL database using BLASTN, as described above. The cDNA sequences of SEQ ID NO: 43, 52, 60 and 61 were determined to have less than 75% identity to sequences in the EMBL database using BLASTN, as described above. The cDNA sequences of SEQ ID NO: 24, 51 and 100 were determined to have less than 90% identity to sequences in the EMBL database using BLASTN, as described above.

EXAMPLE 16

Modification of a Reporter Gene under Control of the Superubiquitin Promoter

Six independent *Arabidopsis thaliana* transgenic lines were transformed with *Pinus radiata* superubiquitin promoter constructs to demonstrate the relative expression of a GUS reporter gene under control of different superubiquitin promoter constructs. The reporter constructs in the plasmid pBI-101 contained the GUS (β-D-glucuronidase) reporter gene in frame with the superubiquitin promoter with the intron (SEQ ID NO: 2), the superubiquitin promoter without the intron (SEQ ID NO: 3), and the CaMV 35S promoter. A reporter gene construct without a promoter sequence was used as control.

Groups of six *Arabidopsis thaliana* plants were transformed with the reporter constructs described above, using *Agrobacterium tumefaciens* transformation protocols. *A. tumefaciens* was transformed with 100 ng of the plasmid DNA according to standard techniques, as described, for example, by Bevan (*Nucleic Acids Res.* 12:8711–8721, 1984). Fresh plant material was collected from each plant, protein extracted from the whole plant, and the protein concentration determined (Bradford, *Anal. Biochem.* 72:248–254, 1976). The protein samples were diluted with carrier bovine serum albumin to 100 ng protein to maintain readings on the fluorimeter in the linear part of the standard curve using 4-methyl-umbelliferone (MU). GUS activity was quantified by fluorimetric analysis, using a Victor 1420 multi-label counter (Wallac, Turku, Finland) as described by Jefferson (*Plant Mol. Biol. Rep.* 5:387–405, 1987). As shown in FIG. 1, the construct containing the superubiquitin promoter without the intron showed seven times more GUS activity than the CaMV 35S promoter and the construct containing the superubiquitin promoter with the intron showed sixty two times more GUS activity than the CaMV 35S promoter. No activity was detected for the promoter-less control construct.

EXAMPLE 17

Determination of the Activity of Superubiquitin Promoter Constructs in Tobacco Plant Protoplasts Isolation of Protoplasts Protoplasts were isolated from sterile tobacco (*Nicotiana tabacum*) leaf tissue and transformed with superubiquitin promoter constructs. Mesophyll protoplasts were prepared according to the method of Bilang et al., *Plant Molecular Biology Manual* A1:1–16, 1994. A number of fully expanded leaves were removed from sterile wild type tobacco plants, sliced perpendicular to the midrib and submerged in a digestion enzyme solution containing 1.2% cellulase and 0.4% pectinase (Sigma, St. Louis Mo.). The leaves were left to incubate in the dark without agitation at 26° C. for approximately 18 hours. The leaf strips were then gently agitated for 30 min to release the protoplasts. Protoplasts were further purified by filtration through 100 μm nylon mesh. One ml of W5 solution (154 mM $MgCl_2$, 125 mM $CaCl_2$, 5 mM KCl, 5 mM glucose, pH 5.8–6) was carefully layered on top of the filtrate and centrifuged at 80×g for 10 min. The live protoplast layer was removed with a wide bore pipette, washed twice with 10 ml W5 solution using centrifugation at 70×g for 5 min, with final resuspension in 5 ml W5 solution. Protoplasts were counted in a hemocytometer and viability was determined under the microscope after staining with 5 mg/ml fluoroscein diacetate (FDA) in 100% acetone.

Transformation with Promoter Constructs

The isolated protoplasts were transformed with plasmid DNA using a polyethylene glycol protocol. After centrifugation of the purified protoplasts at 70×g for 5 min, they were resuspended in MMM solution (15 mM $MgCl_2$, 0.1% w/v 2[N-morpholino]ethanesulfonic acid (MES), 0.5 M mannitol pH 5.8) to a density of $2 \times 10^6$ protoplasts/ml. Aliquots containing $5 \times 10^5$ protoplasts/ml in 250 μl were distributed to 15 ml tubes and mixed with 20 μg plasmid DNA. 250 μl polyethylene glycol-4000 (40%) was gently added and incubated for 5 minutes at room temperature. Ten ml W5 solution was slowly added, the protoplasts centrifuged at 70×g for 5 min and finally resuspended in 2 ml K3 medium (Bilang et al., *Plant Molecular Biology Manual* A1:1–16, 1994). The transformed protoplasts were incubated in the dark at 26° C. for 24 hours before protein was extracted for reporter enzyme assays using 4-methyl-umbelliferyl-glucuronide (MUG).

Protein was extracted from the protoplasts using the following protocol. Transformed protoplast suspensions were centrifuged at 70×g for 10 min, resuspended in 50 μl extraction buffer (Jefferson, *Plant Mol. Biol. Rep.* 5:387–405, 1987) and vigorously mixed using a vortex. The homogenate was cleared by centrifugation at 4,300 rpm for 5 min, the supernatant removed and used for protein assays (Bradford, *Anal. Biochem.* 72:248–254, 1976).

Figure 2:
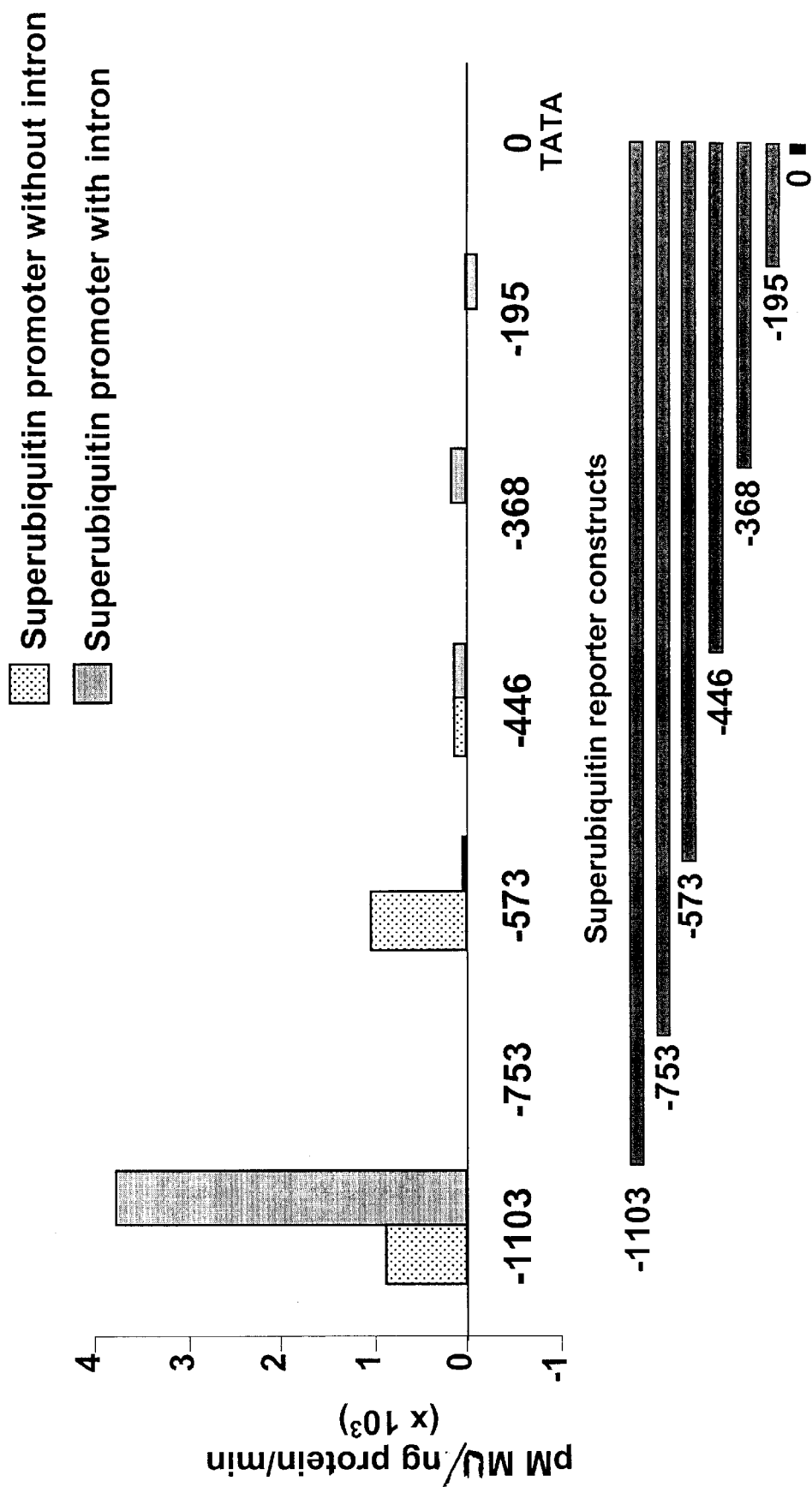
FIG. 2 shows the expression of the GUS gene in tobacco plant protoplasts by deletion constructs containing the superubiquitin promoter with or without the intron. The constructs contained 1,103; 753; 573; 446; 368; and 195 bp upstream of the TATA sequence (bp numbers 1,104–1,110 of SEQ ID NO: 2). The GUS expression was measured by fluorimetric determination of 4-methyl-umbelliferone (MU) in protein extracts from these protoplasts.

The results shown in FIG. 2 demonstrate the promoter activity of deletion constructs of the superubiquitin promoter without the intron (SEQ ID NO: 3) and the superubiquitin promoter with the intron (SEQ ID NO: 2) in tobacco plant protoplasts transformed as described above. The deletion constructs were made in plasmid pBI-101 that contained the GUS reporter gene, using Endonuclease III (Gibco BRL, Gaithersburg, Md.) according to the manufacturer's protocols. The deletion constructs contained 1,103; 753; 573; 446; 368 and 195 bp of superubiquitin promoter sequence, respectively, upstream of the TATA sequence (bp numbers 1,104–1,110 of SEQ ID NO: 2). A control construct containing no sequence upstream of the TATA sequence was also made. These results show that the construct containing the entire superubiquitin promoter with the intron had the highest MU activity in the protoplasts.

Figure 3:
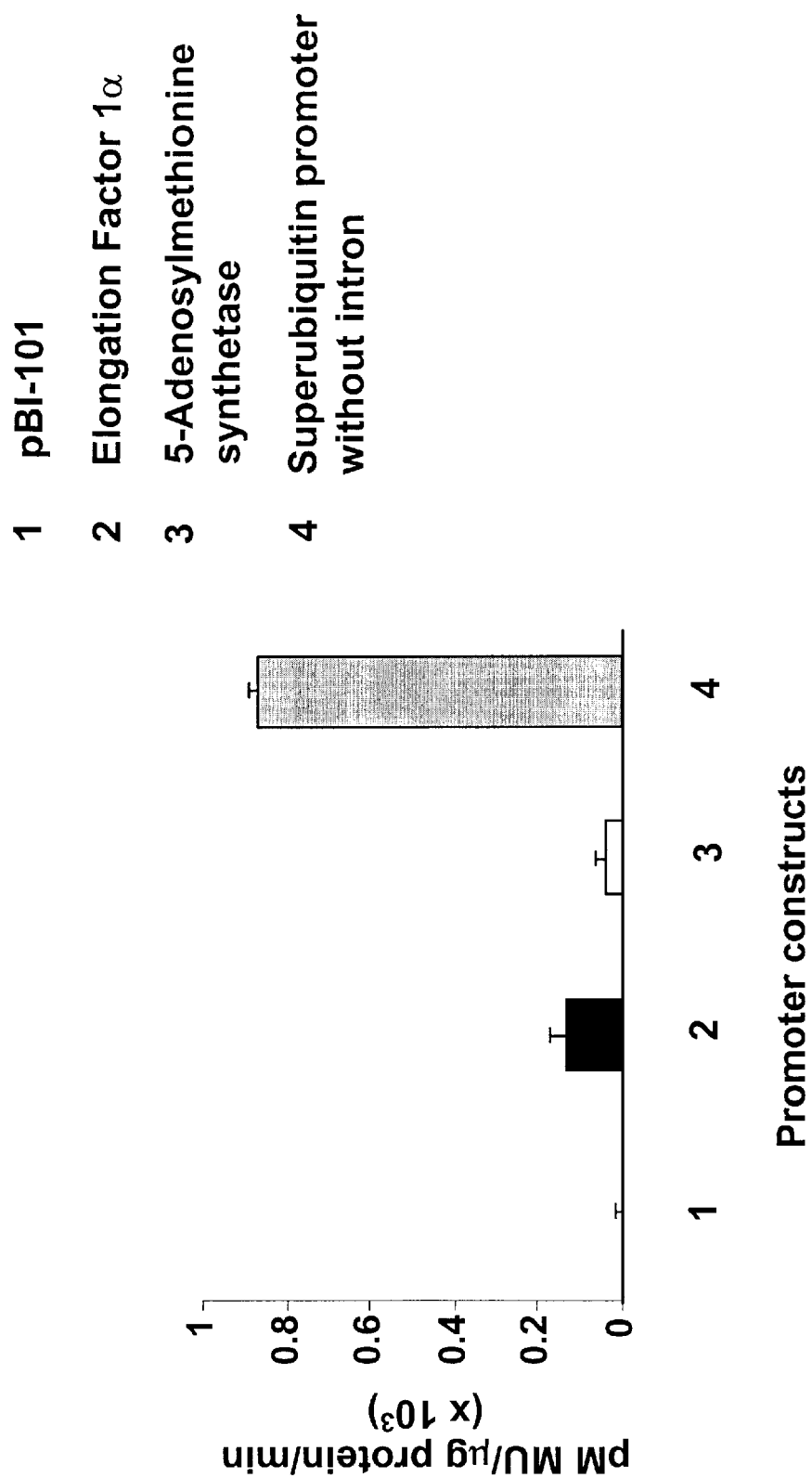
FIG. 3 shows the expression of the GUS gene in tobacco plant protoplasts by constructs containing *P. radiata* either the constitutive promoters Elongation factor-1 alpha, 5-adenosylmethionine synthetase or the superubiquitin promoter without the intron. The GUS expression was measured by fluorimetric determination of 4-methyl-umbelliferone (MU) in protein extracts from these protoplasts.

In FIG. 3, the tobacco protoplasts were transformed with four different promoter constructs in plasmid pBI-101 containing the GUS reporter gene. These included the superubiquitin promoter without the intron (SEQ ID NO: 3), an elongation factor 1ax promoter (SEQ ID NO: 99) and a 5-adenosylmethionine synthetase promoter (SEQ ID NO: 100). A promoterless control was included in the experiment, and is referred to in FIG. 3 as pBI-101.

What is claimed is:

1. An isolate polynucleotide comprising nucleotides 1–1063 of SEQ ID NO: 94.

2. A genetic construct comprising a polynucleotide according to claim 1.

3. A genetic construct comprising, in the 5'-3' direction:
   (a) a promoter sequence,
   (b) a DNA sequence of interest; and
   (c) a gene termination sequence,
   wherein the promoter sequence comprises an isolated polynucleotide according to claim 1.

4. The genetic construct of claim 3, wherein the DNA sequence of interest comprises an open reading frame encoding a polypeptide of interest.

5. The genetic construct of claim 3, wherein the DNA sequence of interest further comprises a noncoding region of a gene encoding a polypeptide of interest.

6. A transgenic cell comprising a genetic construct of any one of claims 2–5.

7. A plant, or a part or propagule or progeny thereof, comprising a genetic construct according to any one of claims 2–5.

8. A plant, or a part or propagule or progeny thereof, comprising a transgnic cell according to claim 6.

9. A method for modifying gene expression in a plant comprising stably incorporating into the genome of the plant a genetic construct according to any one of claims 2–5.

10. A method for producing a plant having modified gene expression comprising:
   (a) transforming a plant cell with a genetic construct to provide a transgenic cell, wherein the genetic construct comprises: (i) a promoter sequence comprising a sequence o f nucleotides 1–1063 of SEQ ID NO: 94; (ii) a DNA sequence of interest; and (iii) a gene termination sequence; and
   (b) cultivating the transgenic cell under conditions.conducive to regeneration and mature plant growth.

11. A method for modifying a phenotype of a plant, comprising stably incorporating into the genome of the plant a genetic construct comprising:
   (a) a promoter sequence comprising a sequence of nucleotides 1–1063 of SEQ ID NO: 94;
   (b) a DNA sequence of interest; and
   (c) a gene termination sequence.

12. A polynucleotide comprising a sequence of nucleotides 1–1063 of SEQ ID NO: 94 operably linked to a heterologous polynucleotide.

13. The polynucleotide of claim 12, wherein the heterologous polynucleotide comprises an open reading frame.

14. An isolated polynucleotide comprising a sequence selected from the group consisting of:
   (a) complements of a sequence of nucleotides 1–1063 of SEQ ID NO: 94;
   (b) reverse complements of a sequence of nucleotides 1–1063 of SEQ ID NO: 94, and
   (c) reverse sequences of a sequence of nucleotides 1–1063 of SEQ ID NO: 94.

* * * * *